United States Patent
Sjoeholm et al.

(10) Patent No.: US 9,109,211 B2
(45) Date of Patent: Aug. 18, 2015

(54) POLYPEPTIDES HAVING PHYTASE ACTIVITY AND POLYNUCLEOTIDES ENCODING SAME

(71) Applicant: Novozymes A/S, Bagsvaerd (DK)

(72) Inventors: Carsten Sjoeholm, Alleroed (DK); Soeren Flensted Lassen, Farum (DK); Lars Kobberoee Skov, Ballerup (DK); Leonardo De Maria, Frederiksberg (DK)

(73) Assignee: Novozymes A/S, Bagsvaerd (DK)

( * ) Notice: Subject to any disclaimer, the term of this patent is extended or adjusted under 35 U.S.C. 154(b) by 219 days.

(21) Appl. No.: 13/946,229

(22) Filed: Jul. 19, 2013

(65) Prior Publication Data

US 2013/0298267 A1 Nov. 7, 2013

Related U.S. Application Data

(62) Division of application No. 13/327,831, filed on Dec. 16, 2011, now Pat. No. 8,697,063, which is a division of application No. 12/022,221, filed on Jan. 30, 2008, now Pat. No. 8,101,391.

(60) Provisional application No. 60/887,242, filed on Jan. 30, 2007.

(30) Foreign Application Priority Data

Jan. 30, 2007 (EP) ..................... 07101395

(51) Int. Cl.
*C12N 9/16* (2006.01)
*C12N 15/82* (2006.01)
*A23L 1/305* (2006.01)
*C12P 7/06* (2006.01)

(52) U.S. Cl.
CPC .............. *C12N 9/16* (2013.01); *A23L 1/3053* (2013.01); *C12N 15/8243* (2013.01); *C12P 7/06* (2013.01); *Y02E 50/17* (2013.01)

(58) Field of Classification Search
CPC ... C12N 9/16; C12N 15/8243; C12N 15/8257
USPC ................ 435/41, 69.1, 196, 252.3
See application file for complete search history.

(56) References Cited

U.S. PATENT DOCUMENTS

| | | | |
|---|---|---|---|
| 8,101,391 B2 | 1/2012 | Sjoeholm et al. | |
| 8,697,063 B2 * | 4/2014 | Sjoeholm et al. | 435/196 |
| 2002/0006647 A1 | 1/2002 | Veit et al. | |
| 2008/0222740 A1 | 9/2008 | Sjoeholm et al. | |
| 2008/0263688 A1 | 10/2008 | Lassen et al. | |
| 2013/0298267 A1 | 11/2013 | Sjoeholm et al. | |

FOREIGN PATENT DOCUMENTS

| | | |
|---|---|---|
| WO | 2006/038128 A2 | 4/2006 |
| WO | 2006/043178 A2 | 4/2006 |

OTHER PUBLICATIONS

Harold Fox, Request for Certificate of Correction of U.S. Patent No. 8,053,221 filed on Jun. 24, 2013.
Certificate of Correction for U.S. Patent No. 8,053,221 granted on Aug. 13, 2013.
Pen et al., "Phytase-Containing Transgenic Seeds as a Novel Feed Additive for Improved Phosphorous Utilization", Biotechnology, vol. 11, pp. 811-814 (1993).
Zinin et al., "Gene Cloning Expression and Characterization of Novel Phytase from Obessumbacterium proteus", FEMS Microbiology Letters, vol. 236, pp. 283-290 (2004).
Zinin et al., GenBank Accession No. AY378096 (2005).
Zinin et al., UniProt Accession No. AAQ90419 (2005).

* cited by examiner

*Primary Examiner* — Kevin Hill
(74) *Attorney, Agent, or Firm* — Elias Lambiris

(57) ABSTRACT

The present invention relates to polypeptides having phytase activity. These polypeptides have an amino acid sequence which has at least 70% identity to either of three phytases derived from the bacterium *Buttiauxella*, and which comprises at least one of the following amino acids at the position indicated: 119N, 120L, and/or 121E. These phytases have an improved specific activity. Additional specific amino acid substitutions are also disclosed which characterize and distinguish additional phytases of the invention having improved properties such as temperature and/or pH stability, pH activity profile, temperature activity profile, substrate profile, improved performance in animal feed in vitro or in vivo. The invention also relates to isolated polynucleotides encoding the polypeptides, nucleic acid constructs, vectors, and host cells comprising the polynucleotides as well as methods for producing and using the polypeptides.

37 Claims, 9 Drawing Sheets

Fig. 1

```
Numbering                                      1         10        20
AEH25057    MTISAFNRKKLTLHPGLFVALSAIFSLGSTAYANDTPASGYQVEKVVILSRHGVRAPTKM
AEH25059    MTISAFNRKKLTLHPGLFVALSAIFSLGSTAYANDTPASGYQVEKVVILSRHGVRAPTKM
AEH25058    MTISAFNRKKLTLHPGLFVALSAIFSLGSTAYANDTPASGYQVEKVVILSRHGVRAPTKM
AEH25067    MTISAFNRKKLTLHPGLFVALSAIFSLGSTAYANDTPASGYQVEKVVILSRHGVRAPTKM
AEH25071    MTISAFNRKKLTLHPGLFVALSAIFSLGSTAYANDTPASGYQVEKVVILSRHGVRAPTKM
AEH25072    MTISAFNRKKLTLHPGLFVALSAIFSLGSTAYANDTPASGYQVEKVVILSRHGVRAPTKM
AEH25074    MTISAFNRKKLTLHPGLFVALSAIFSLGSTAYANDTPASGYQVEKVVILSRHGVRAPTKM
AEH25076    MTISAFNRKKLTLHPGLFVALSAIFSLGSTAYANDTPASGYQVEKVVILSRHGVRAPTKM
AEH25075    MTISAFNRKKLTLHPGLFVALSAIFSLGSTAYANDTPASGYQVEKVVILSRHGVRAPTKM
AEH25073    MTISAFNRKKLTLHPGLFVALSAIFSLGSTAYANDTPASGYQVEKVVILSRHGVRAPTKM
AEH25070    MTISAFNRKKLTLHPGLFVALSAIFSLGSTAYANDTPASGYQVEKVVILSRHGVRAPTKM
AEH25069    MTISAFNRKKLTLHPGLFVALSAIFSLGSTAYANDTPASGYQVEKVVILSRHGVRAPTKM
AEH25066    MTISAFNRKKLTLHPGLFVALSAIFSLGSTAYANDTPASGYQVEKVVILSRHGVRAPTKM
AEH25060    MTISAFNRKKLTLHPGLFVALSAIFSLGSTAYANDTPASGYQVEKVVILSRHGVRAPTKM
AEH25068    MTISAFNRKKLTLHPGLFVALSAIFSLGSTAYANDTPASGYQVEKVVILSRHGVRAPTKM
AEH25063    MTISAFNRKKLTLHPGLFVALSAIFSLGSTAYANDTPASGYQVEKVVILSRHGVRAPTKM
AEH25065    MTISAFNRKKLTLHPGLFVALSAIFSLGSTAYANDTPASGYQVEKVVILSRHGVRAPTKM
AEH25062    MTISAFNRKKLTLHPGLFVALSAIFSLGSTAYANDTPASGYQVEKVVILSRHGVRAPTKM
AEH25061    MTISAFNRKKLTLHPGLFVALSAIFSLGSTAYANDTPASGYQVEKVVILSRHGVRAPTKM
AEH25056    MTISAFNRKKLTLHPGLFVALSAIFSLGSTAYANDTPASGYQVEKVVILSRHGVRAPTEM
AEH25051    MTISAFNRKKLTLHPGLFVALSAIFSLGSTAYANDTPASGYQVEKVVILSRHGVRAPTKM
AEH25064    MTISAFNRKKLTLHPGLFVALSAIFSLGSTAYANDTPASGYQVEKVVILSRHGVRAPTKM
SEQ4        ---------------------FSLGLTAYASDTPASGYQIEKVVILSRHGVRAPTKM
SEQ6        MTFSAFNRKKLTLHPGLFVALSAIFSLGSTAYANDTPASGYQVEKVVILSRHGVRAPTKM
SEQ2        MTISAFNHKKLTLHPGLFVALSAIFSLGSTAYANDTPASGYQVEKVVILSRHGVRAPTKM
                             .*******.****************.*
```

Fig. 1 - continued

```
Numbering       30        40        50        60        70        80
AEH25057    TQTMRDVTPNTWPEWPVKLGYITPRGEHLISLMGGFYRQKFQQQGILSQGSCPTPNSIYV
AEH25059    TQTMRDVTPNTWPEWPVKLGYITPRGEHLISLMGGFYRQKFQQQGILSQGSCPTPNSIYV
AEH25058    TQTMRDVTPNTWPEWPVKLGYITPRGEHLISLMGGFYRQKFQQQGILSQGSCPTPNSIYV
AEH25067    TQTMRDVTPNTWPEWPVKLGYITPRGEHLISLMGGFYRQKFQQQGILSQGSCPTPNSIYV
AEH25071    TQTMRDVTPNTWPEWPVKLGYITPRGEHLISLMGGFYRQKFQQQGILSQGSCPTPNSIYV
AEH25072    TQTMRDVTPNTWPEWPVKLGYITPRGEHLISLMGGFYRQKFQQQGILSQGSCPTPNSIYV
AEH25074    TQTMRDVTPNTWPEWPVKLGYITPRGEHLISLMGGFYRQKFQQQGILSQGSCPTPNSIYV
AEH25076    TQTMRDVTPYTWPEWPVKLGYITPRGEHLISLMGGFYRQKFQQQGILSQGSCPTPNSIYV
AEH25075    TQTMRDVTPNTWPEWPVKLGYITPRGEHLISLMGGFYRQKFQQQGILSQGSCPTPNSIYV
AEH25073    TQTMRDVTPNTWPEWPVKLGYITPRGEHLISLMGGFYRQKFQQQGILSQGSCPTPNSIYV
AEH25070    TQTMRDVTPNTWPEWPVKLGYITPRGEHLISLMGGFYRQKFQQQGILSQGSCPTPNSIYV
AEH25069    TQTMRDVTPNTWPEWPVKLGYITPRGEHLISLMGGFYRQKFQQQGILSQGSCPTPNSIYV
AEH25066    TQTMRDVTPNTWPEWPVKLGYITPRGEHLISLMGGFYRQKFQQQGILSQGSCPTPNSIYV
AEH25060    TQTMRDVTPNTWPEWPVKLGYITPRGEHLISLMGGFYRQKFQQQGILSQGSCPTPNSIYV
AEH25068    TQTMRDVTPNTWPEWPVKLGYITPRGEHLISLMGGFYRQKFQQQGILSQGSCPTPNSIYV
AEH25063    TQTMRDVTPNTWPEWPVKLGYITPRGEHLISLMGGFYRQKFQQQGILSQGSCPTPNSIYV
AEH25065    TQTMRDVTPNTWPEWPVKLGYITPRGEHLISLMGGFYRQKFQQQGILSQGSCPTPNSIYV
AEH25062    TQTMRDVTPNTWPEWPVKLGYITPRGEHLISLMGGFYRQKFQQQGILSQGSCPTPNSIYV
AEH25061    TQTMRDVTPNTWPEWPVKLGYITPRGEHLISLMGGFYRQKFQQQGILSQGSCPTPNSIYV
AEH25056    TQTMRDVTPNTWPEWPVKLGYITPRGEHLISLMGGFYRQKFQQQGILSQGSCPTPNSIYV
AEH25051    TQTMRDVTPNTWPEWPVKLGYITPRGEHLISLMGGFYRQKFQQQGILSQGSCPTPNSIYV
AEH25064    TQTMRDVTPNTWPEWPVKLGYITPRGEHLISLMGGFYRQKFQQQGILSQGSCPTPNSIYV
SEQ4        TQTMRDVTPNSWPEWPVKLGYITPRGEHLISLMGGFYRQKFQQKGILSQGSCPTPNSIYV
SEQ6        TQTMRDVTPNTWPEWPVKLGYITPRGEHLISLMGGFYREKFQQQGILSQGSCPAPNSIYV
SEQ2        TQTMRDVTPNTWPEWPVKLGYITPRGEHLISLMGGFYREKFQQQGILSQGSCPTPNSIYV
            ********:***************************:****:**********:*****
```

Fig. 1 - continued

```
Numbering       90        100       110       120       130       140
AEH25057   WADVDQRTLKTGEAFLAGLAPECHLTIHHQQDIKKADPLFHPVKAGVCSMDKTQVQQAVE
AEH25059   WADVDQRTLKTGEAFLAGLAPECHLTIHHQQDIKKADPLFHPVKAGICSMDKTQVQQAVE
AEH25058   WADVDQRTLKTGEAFLAGLAPECHLTIHHQQDIKKADPLFHPVKAGTCSMDKTQVQQAVE
AEH25067   WADVDQRTLKTGEAFLAGLAPECHLTIHHQQDIKKADPLFHPVKAGICSMDKTQVQQAVE
AEH25071   WTDVDQRTLKTGEAFLAGLAPECHLTIHHQQDIKKADPLFHPVKAGICSMDKTQVQQAVE
AEH25072   WTDVDQRTLKTGEAFLAGLAPECHLTIHHQQDIKKADPLFHPVKAGICSMDKTQVQQAVE
AEH25074   WADVEQRTLKTGEAFLAGLAPECHLTIHHQQDIKKADPLFHPVKAGICSMDKTQVQQAVE
AEH25076   WADVEQRTLKTGEAFLAGLAPECHLTIHHQQDIKKADPLFHPVKAGICSMDKTQVQQAVE
AEH25075   WTDVDQRTLKTGEAFLAGLAPECHLTIHHQQDIKKADPLFHPVKAGICSMDKTQVQQAVE
AEH25073   WTDVEQRTLKTGEAFLAGLAPECHLTIHHQQDIKKADPLFHPVKAGTCSMDKTQVQQAVE
AEH25070   WADVDQRTLKTGEAFLAGLAPECHLTIHHQQDIKKADPLFHPVKAGICSMDKTQVQQAVE
AEH25069   WADVDQRTLKTGEAFLAGLAPECHLTIHHQQDIKKADPLFHPVKAGICSMDKTQVQQAVE
AEH25066   WADVDQRTLKTGEAFLAGLAPECHLTIHHQQDIKKADPLFHPVKAGTCSMDKTQVQQAVE
AEH25060   WADVDQRTLKTGEAFLAGLAPECHLTIHHQQDIKKADPLFHPVKAGTCSMDKTQVQQAVE
AEH25068   WADVDQRTLKTGEAFLAGLAPECHLTIHHQQDIKKADPLFHPVKAGTCSMDKTQVQQAVE
AEH25063   WADVDQRTLKTGEAFLAGLAPECHLTIHHQQDIKKADPLFHPVKAGTCSMDKTQVQQAVE
AEH25065   WADVDQRTLKTGEAFLAGLAPECHLTIHHQQDIKKADPLFHPVKAGTCSMDKTQVQQAVE
AEH25062   WADVDQRTLKTGEAFLAGLAPECHLTIHHQQDIKKADPLFHPVKAGTCSMDKTQVQQAVE
AEH25061   WADVDQRTLKTGEAFLAGLAPECHLTIHHQQDIKKADPLFHPVKAGTCSMDKTQVQQAVE
AEH25056   WADVDQRTLKTGEAFLAGLAPECHLTIHHQQDIKKADPLFHPVKAGTCSMDKTQVQQAVE
AEH25051   WADVDQRTLKTGEAFLAGLAPECHLTIHHQQDIKKADPLFHPVKAGTCSMDKTQVQQAVE
AEH25064   WADVDQRTLKTGEAFLAGLAPECHLTIHHQQDIKKADPLFHPVKAGTCSMDKTQVQQAVE
SEQ4       WADVDQRTLKTGEAFLAGLAPQCGLTIHHQQNLEKADPLFHPVKAGTCSMDKTQVQQAVE
SEQ6       WADVDQRTLKTGEAFLAGLAPQCGLTIHHQQNLEKADPLFHPVKAGTCSMDKTQVQQAVE
SEQ2       WADVDQRTLKTGEAFLAGLAPQCGLTIHHQQNLEKADPLFHPVKAGTCSMDKTRLQQAVE
           *:**:***************:* ******:::************ ******::*****
```

Fig. 1- continued

```
Numbering       150       160       170       180       190       200
AEH25057   KEAQTPIDNLNQHYIPFLALMNTTLNFSTSAWCQKHSADKSCDLGLSMPSKLSIKDNGNK
AEH25059   KEAQTPIDNLNQHYIPFLALMNTTLNFSTSAWCQKHSADKSCDLGLSMPSKLSIKDNGNK
AEH25058   KEAQTPIDNLNQHYIPFLALMNTTLNFSTSAWCQKHSADKSCDLGLSMPSKLSIKDNGNT
AEH25067   KEAQTPIDNLNQHYIPFLALMNTTLNFSTSAWCQKHSADKSCDLGLSMPSKLSIKDNGNT
AEH25071   KEAQTPIDNLNQHYIPSLALMNTTLNFSKSPWCQKHSADKSCDLGLSMPSKLSIKDNGNE
AEH25072   KEAQTPIDNLNQHYIPSLALMNTTLNFSKSPWCQKHSADKSCDLGLSMPSKLSIKDNGNE
AEH25074   KEAQTPIDNLNQRYIPSLALMNTILNFSKSPWCQKHSADKSCDLGLSMPSKLSIKDNGNE
AEH25076   KEAQTPIDNLNQRYIPSLALMNTILNFSKSPWCQKHSADKSCDLGLSMPSKLSIKDNGNE
AEH25075   KEAQTPIDNLNQRYIPSLALMNTILNFSKSPWCQKHSADKSCDLGLSMPSKLSIKDNGNE
AEH25073   KEAQTPIDNLNQRYIPSLALMNTTLNFSKSPWCQKHSADKNCDLALSMPSKLSIKDNGNE
AEH25070   KEAQTPIDNLNQHYIPFLALMNTTLNFSTSAWCQKHSADKSCDLGLSMPSKLSIKDNGNE
AEH25069   KEAQTPIDNLNQHYIPFLALMNTTLNFSTSAWCQKHSADKSCDLGLSMPSKLSIKDNGNT
AEH25066   KEAQTPIDNLNQHYIPFLALMNTTLNFSTSAWCQKHSADKSCDLGLSMPSKLSIKDNGNK
AEH25060   KEAQTPIDNLNQHYIPFLALMNTTLNFSTSAWCQKHSADKSCDLGLSMPSKLSIKDNGNE
AEH25068   KEAQTPIDNLNQHYIPFLALMNTTLNFSTSAWCQKHSADKSCELGLSMPSKLSIKDNGNE
AEH25063   KEAQTPIDNLNQHYIPFLALMNTTLNFSKSAWCQKHSADKSCDLGLSMPSKLSIKDNGNK
AEH25065   KEAQTPIDNLNQRYIPFLALMNTTLNFSTSAWCQKHSADKSCDLGLSMPSKLSIKDNGNK
AEH25062   KEAQTPIDNLNQHYIPFLALMNTTLNFSTSAWCQKHSADKSCDLGLSMPSKLSIKDNGNK
AEH25061   KEAQTPIDNLNQHYIPFLALMNTTLNFSTSAWCQKHSADKSCDLGLSMPSKLSIKDNGNK
AEH25056   KEAQTPIDNLNQHYIPFLALMNTTLNFSTSAWCQKHSADKSCDLGLSMPSKLSIKDNGNK
AEH25051   KEAQTPIDNLNQHYIPFLALMNTTLNFSTSAWCQKHSADKSCDLGLSMPSKLSIKDNGNK
AEH25064   KEAQTPIDNLNQHYIPSLALMNTTLNFSTSAWCQKHSADKSCDLGLSMPSKLSIKDNGNK
SEQ4       KEAQMPIENLNQHYIPSLALMNTTLNFSTSAWCQKHSADKSCDLAQSMPSKLSIKDNGNK
SEQ6       KEAQTPIDNLNQHYIPSLALMNTTLNFSTSAWCQKHSADKSCDLAQSMPSKLSIKDNGNK
SEQ2       KEAQTPIENLNQHYIPSLALMNTTLNFSTSAWCQKHSADKSCDLAQSMPSKLSIKDNGNK
           **** **:****:*** ****** ****.*.*********.*:*. ************
```

Fig. 1 - continued

```
Numbering      210       220       230       240       250       260
AEH25057   VALDGAIGLSSTLAEIFLLEYAQGMPQAAWGNIHSEQEWASLLKLHNVQFDLMARTPYIA
AEH25059   VALDGAIGLSSTLAEIFLLEYAQGMPQAAWGNIHSEQEWASLLKLHNVQFDLMARTPYIA
AEH25058   VALDGAIGLSSTLAEIFLLEYAQGMPQAAWGNIHSEQEWASLLKLHNVQFDLMARTPYIA
AEH25067   VALDGAIGLSSTLAEIFLLEYAQGMPQAAWGNIHSEQEWASLLKLHNVQFDLMARTPYIA
AEH25071   VALDGAIGLSSTLAEIFLLEYAQGMPQAAWGNIHSEQEWASLLKLHNVQFDLMERTPYIA
AEH25072   VSLDGAIGLSSTLAEIFLLEYAQGMPQAAWGNIHSEQEWALLLKLHNVYFDLMERTPYIA
AEH25074   VALDGAIGLSSTLAEIFLLEYAQGMPQVAWGNIHSEQEWASLLKLHNVHFDLMERTPYIA
AEH25076   VALDGAIGLSSTLAEIFLLEYAQGMPQVAWGNIHSEQEWASLLKLHNVHFDLMERTPYIA
AEH25075   VALDGAIGLSSTLAEIFLLEYAQGMPQVAWGNIHSEQEWASLLKLHNVHFDLMERTPYIA
AEH25073   VALDGAIGLSSTLAEIFLLEYAQGMPQAAWGNIHSEQEWASLLKLHNVQFDLMERTPYIA
AEH25070   VSLDGAIGLSSTLAEIFLLEYAQGMPQAAWGNIHSEQEWASLLKLHNVQFDLMERTPYIA
AEH25069   VALDGAIGLSSTLAEIFLLEYAQGMPQAAWGNIHSEQEWASLLKLHNVQFDLMERTPYIA
AEH25066   VALDGAIGLSSTLAEIFLLEYAQGMPQAAWGNIHSEQEWASLLKLHNVQFDLMERTPYIA
AEH25060   VALDGAIGLSSTLAEIFLLEYAQGMPQAAWGNIHSEQEWASLLKLHNVQFDLMARTPYIA
AEH25068   VALDGAIGLSSTLAEIFLLEYAQGMPQAAWGNIHSEQEWASLLKLHNVQFDLMARTPYIA
AEH25063   VALDGAIGLSSTLAEIFLLEYAQGMPQAAWGNIHSEQEWASLLKLHNVQFDLMARTPYIA
AEH25065   VALDGAIGLSSTLAEIFLLEYAQGMPQAAWGNIHSEQEWASLLKLHNVQFDLMARTPYIA
AEH25062   VALDGAIGLSSTLAEIFLLEYAQGMPQAAWGNIHSEQEWASLLKLHNVYFDLMARTPYIA
AEH25061   VALCGAIGLSSTLAEIFLLEYAQGMPQAAWGNIHSEQEWASLLKLHNVQFDLMARTPYIA
AEH25056   VALDGAIGLSSTLAEIFLLEYAQGMPQAAWGNIHSEQEWASLLKLHNVQFDLMARTPYIA
AEH25051   VALDGAIGLSSTLAEIFLLEYAQGMPQAAWGNIHSEQEWASLLKLHNVQFDLMARTPYIA
AEH25064   VALDGAIGLSSTLAEIFLLEYAQGMPQAAWGNIHSEQEWASLLKLHNVQFDLMARTPYIA
SEQ4       VALDGAIGLSSTLAEIFLLEYAQGMPQAAWGNIHSEQEWASLLKLHN*T*QFDLMARTPYIA
SEQ6       VALDGAIGLSSTLAEIFLLEYAQGMPQAAWGNIHSEQEWASLLKLHN*A*QFDLMARTPYIA
SEQ2       VALDGA*V*GLSSTLAEIFLLEYAQGMPQAAWG*K*IHSEQ*D*WA*E*LLKLHN*A*QFDLMARTPYIA
           *:* **:******************.***:*****:** ******. **** ******
```

Fig. 1- continued

```
Numbering      270        280        290        300        310        320
AEH25057   RHNGTPLLQAISNALNPNATESKLPDISPDNKILFIAGHDTNIANIAGMLNMRWTLPGQP
AEH25059   RHNGTPLLQAISNALNPNATESKLPDISPDNKILFIAGHDTNIANIAGMLNMRWTLPGQP
AEH25058   RHNGTPLLQAISNALNPNATESKLPDISPDNKILFIAGHDTNIANIAGMLNMRWTLPGQP
AEH25067   RHNGTPLLQAISNALNPNATESKLPDISPDNKILFIAGHDTNIANIAGMLNMRWTLPGQP
AEH25071   RHKGTPLLQAISNALNPNATESKLPDISPDNKILFIAGHDTNIANIAGMLNMRWTLPGQP
AEH25072   RHKGTPLLQAISNALNPNATESKLPDISPDNKILFIAGHDTNIANIAGMLNMRWTLPGQP
AEH25074   RHKGTPLLQAISNALNPNATESKLPDISPDNKILFIAGHDTNIANIAGMLNMRWTLPGQP
AEH25076   RHKGTPLLQAISNALNPNATESKLPDISPDNKILFIAGHDTNIANIAGMLNMRWTLPGQP
AEH25075   RHKGTPLLQAISNALNPNATESKLPDISPDNKILFFAGHDTNIANIAGMLNMRWTLPGQP
AEH25073   RHKGTPLLQAISNALNPNATESKLPDISPDNKILFIAGHDTNIANIAGMLNMRWTLPGQP
AEH25070   RHKGTPLLQAISNALNPNATESKLPDISPDNKILFIAGHDTNIANIAGMLNMRWTLPGQP
AEH25069   RHKGTPLLQAISNALNPNATESKLPDISPDNKILFIAGHDTNIANIAGMLNMRWTLPGQP
AEH25066   RHKGTPLLQAISNALNPNATESKLPDISPDNKILFIAGHDTNIANIAGMLNMRWTLPGQP
AEH25060   RHNGTPLLQAISNALNPNATESKLPDISPDNKILFIAGHDTNIANIAGMLNMRWTLPGQP
AEH25068   RHNGTPLLQAISNALNPNATESKLPDISPDNKILFIAGHDTNIANIAGMLDMRWTLPGQP
AEH25063   RHNGTPLLQAISNALNPNATESKLPDISPDNKILFIAGHDTNIANIAGMLNMRWTLPGQP
AEH25065   RHNGTPLLQAISNALNPNATESKLPDISPDNKILFIAGHDTNIANIAGMLNMRWTLPGQP
AEH25062   RHNGTPLLQAISNALNPNATESKLPDISPDNKILFIAGHDTNIANIAGMLNMRWTLPGQP
AEH25061   RHNGTPLLQAISNALNPNATESKLPDISPDNKILFIAGHDTNIANIAGMLNMRWTLPGQP
AEH25056   RHNGTPLLQAISNALNPNATESKLPDISPDNKILFIAGHDTNIANIAGMLNMRWTLPGQP
AEH25051   RHNGTPLLQAISNALNPNATESKLPDISPDNKILFIAGHDTNIANIAGMLNMRWTLPGQP
AEH25064   RHNGTPLLQAISNALNPNATESKLPDISPDNKILFIAGHDTNIANIAGMLNMRWTLPGQP
SEQ4       AHNGTPLLQTISNALEPKADVSKLPDISSDNKILFIAGHDTNIANIAGMLNMRWTLPGQP
SEQ6       THNGTPLLQTISNALEPKADVSKLPGISPDNKILFLAGHDTNIANIAGMLNMRWTLPGQP
SEQ2       RHNGTPLLQAISNALDPNATASKLPDISPDNKILFIAGHDTNIANISGMLNMRWTLPGQP
           *:******.*****:*:*  ****.**.*******:***********:***.********
```

Fig. 1- continued

```
Numbering    330        340        350        360        370        380
AEH25057    DNTPPGGALVFERLADKSGKQYVSVSMVYQTLEQLRSQTPLSLNQPAGSVQLKIPGCNDQ
AEH25059    DNTPPGGALVFERLADKSGKQYVSVSMVYQTLEQLRSQTPLSLNQPAGSVQLKIPGCNDQ
AEH25058    DNTPPGGALVFERLADKSGKQYVSVSMVYQTLEQLRSQTPLSLNQPAGSVQLKIPGCNDQ
AEH25067    DNTPPGGALVFERLADKSGKQYVSVSMVYQTLEQLRSQTPLSLNQPAGSVQLKIPGCNDQ
AEH25071    DNTPPGGALVFERLADKSGKQYVSVSMVYQTLEQLRSQTPLSLNQPAGSVQLKIPGCNDQ
AEH25072    DNTPPGGALVFERLADKSGKQYVSVSMVYQTLEQLRSQTPLSLNQPAGSVQLKIPGCNDQ
AEH25074    DNTPPGGALVFERLADKSGKQYVSVSMVYQTLEQLRSQTPLSLNQPAGSVQLKIPGCNDQ
AEH25076    DNTPPGGALVFERLADKSGKQYVSVSMVYQTLEQLRSQTPLSLNQPAGSVQLKIPGCNDQ
AEH25075    DNTPPGGALVFERLADKSGKQYVSVSMVYQTLEQLRSQTPLSLNQPAGSVQLKIPGCNDQ
AEH25073    DNTPPGGALVFERLADKSGKQYVSVSMVYQTLEQLRSQTPLSLNQPAGSVQLKIPGCNDQ
AEH25070    DNTPPGGALVFERLADKSGKQYVSVSMVYQTLEQLRSQTPLSLNQPAGSVQLKIPGCNDQ
AEH25069    DNTPPGGALVFERLADKSGKQYVSVSMVYQTLEQLRSQTPLSLNQPAGSVQLKIPGCNDQ
AEH25066    DNTPPGGALVFERLADKSGKQYVSVSMVYQTLEQLRSQTPLSLNQPAGSVQLKIPGCNDQ
AEH25060    DNTPPGGALVFERLADKSGKQYVSVSMVYQTLEQLRSQTPLSLNQPAGSVQLKIPGCNDQ
AEH25068    DNTPPGGALVFERLADKSGKQYVSVSMVYQTLEQLRSQTPLSLNQPAGSVQLKIPGCNDQ
AEH25063    DNTPPGGALVFERLADKSGKQYVSVSMVYQTLEQLRSQTPLSLNQPAGSVQLKIPGCNDQ
AEH25065    DNTPPGGALVFERLADKSGKQYVSVSMVYQTLEQLRSQTPLSLNQPAGSVQLKIPGCNDQ
AEH25062    DNTPPGGALVFERLADKSGKQYVSVSMVYQTLEQLRSQTPLSLNQPAGSVQLKIPGCNDQ
AEH25061    DNTPPGGALVFERLADKSGKQYVSVSMVYQTLEQLRSQTPLSLNQPAGSVQLKIPGCNDQ
AEH25056    DNTPPGGALVFERLADKSGKQYVSVSMVYQTLEQLRSQTPLSLNQPAGSVQLKIPGCNDQ
AEH25051    DNTPPGGALVFERLADKSGKQYVSVSMVYQTLEQLRSQTPLSLNQPAGSVQLKIPGCNDQ
AEH25064    DNTPPGGALVFERLADKSGKQYVSVSMVYQTLEQLRSQTPLSLNQPAGSVQLKIPGCNDQ
SEQ4        DNTPPGGALVFERLADKSGKQYISVSMVYQTLEQLRAQTPLSLNEPAGSVQLKIPGCNDQ
SEQ6        DNTPPGGALVFERLADKSGKQYVSVSMVYQTLEQLRSQTPLSLNQPAGSVQLKIPGCNDQ
SEQ2        DNTPPGGALIFERLADKAGKQYVSVSMVYQTLEQLRAQTPLSLKEPAGSVQLKIPGCNDQ
            ********* ******* *************** ****** : ****************
```

Fig. 1- continued

```
Numbering      390       400       410
AEH25057    TAEGYCPLSTFTRVVSQSVEPGCQLQ
AEH25059    TAEGYCPLSTFTRVVSQSVEPGCQLQ
AEH25058    TAEGYCPLSTFTRVVSQSVEPGCQLQ
AEH25067    TAEGYCPLSTFTRVVSQSVEPGCQLQ
AEH25071    TAEGYCPLSTFTRVVSQSVEPGCQLQ
AEH25072    TAEGYCPLSTFTRVVSQSVEPGCQLQ
AEH25074    TAEGYCPLSTFTRVVSQSVEPGCQLQ
AEH25076    TAEGYCPLSTFTRVVSQSVEPGCQLQ
AEH25075    TAEGYCPLSTFTRVVSQSVEPGCQLQ
AEH25073    TAEGYCPLSTFTRVVSQSVEPGCQLQ
AEH25070    TAEGYCPLSTFTRVVSQSVEPGCQLQ
AEH25069    TAEGYCPLSTFTRVVSQSVEPGCQLQ
AEH25066    TAEGYCPLSTFTRVVSQSVEPGCQLQ
AEH25060    TAEGYCPLSTFTRVVSQSVEPGCQLQ
AEH25068    TAEGYCPLSTFTRVVSQSVEPGCQLQ
AEH25063    TAEGYCPLSTFTRVVSQSVEPGCQLQ
AEH25065    TAEGYCPLSTFTRVVSQSVEPGCQLQ
AEH25062    TAEGYCPLSTFTRVVSQSVEPGCQLQ
AEH25061    TAEGYCPLSTFTRVVSQSVEPGCQLQ
AEH25056    TAEGYCPLSTFTRVVSQSVEPGCQLQ
AEH25051    TAEGYCPLSTFTRVVSQSVEPGCQLQ
AEH25064    TAEGYCPLSTFTRVVSQSVEPGCQLQ
SEQ4        TAEGYCPLSTFTRVVSQSVEPGCQL*P*
SEQ6        TAEGYCPLSTFTRVVSQSVEPGCQLQ
SEQ2        TAEGYCPL*P*TF*K*RVVSQS*E*EPGCQLQ
            *******.**.****** ******
```

Fig. 2

```
Program: needle
Matrix: BLOSUM62
Gap initiation penalty: 10.0
Gap extension penalty: 0.5
Number of identical residues: 315
Length of shortest sequence: 413
% Identity: 315/413 = 76.3%
SEQ2_mature       1                              NDTPASGYQVEKVVILS      17
                                                 ::|..||||:|||||||
UNIPROTQ6U677     1   MTISLFTHSPTRLLKCMPLAFIAASMLTTASYASETEPSGYQLEKVVILS   50
SEQ2_mature      18   RHGVRAPTKMTQTMRDVTPNTWPEWPVKLGYITPRGEHLISLMGGFYREK   67
                     ||||||||||||||||||.||||||||||||||||||||:||||||||:|
UNIPROTQ6U677    51   RHGVRAPTKMTQTMRDVTPNAWPEWPVKLGYITPRGEHLVSLMGGFYRQK  100
SEQ2_mature      68   FQQQGILSQGSCPTPNSIYVWADVDQRTLKTGEAFLAGLAPQCGLTIHHQ  117
                     |||.||||:|.|||.|.:||||||||||||||||||||||:.|:||||
UNIPROTQ6U677   101   FQQLGILSKGRCPTANDVYVWADVDQRTRKTGEAFLAGLAPECHLSIHHQ  150
SEQ2_mature     118   QNLEKADPLFHPVKAGTCSMDKTRLQQAVEKEAQTPIENLNQHYIPSLAL  167
                     |::::|||||||||||.|:|:||::||||::||..||:.||||.|:|||
UNIPROTQ6U677   151   QDIKQADPLFHPVKAGVCTMEKTQVQQAVEQQAGMPIDQLNQHYRPALAL  200
SEQ2_mature     168   MNTTLNFSTSAWCQKHSADKSCDLAQSMPSKLSIKDNGNKVALDGAVGLS  217
                     |::.|||..|.:||:||||::||||||::||||||||||||||||||||
UNIPROTQ6U677   201   MSSVLNFPKSTYCQQHSADQTCDLAQAMPSKLSIKDNGNKVALDGAVGLS  250
SEQ2_mature     218   STLAEIFLLEYAQGMPQAAWGKIHSEQDWAELLKLHNAQFDLMARTPYIA  267
                     ||||||||||||||||.||||||||||..||.||||||||||:|||||
UNIPROTQ6U677   251   STLAEIFLLEYAQGMPDAAWGKIHSEQDWNALLTLHNAQFDLMSRTPYIA  300
SEQ2_mature     268   RHNGTPLLQAISNALDPNATASKLPDISPDNKILFIAGHDTNIANISGML  317
                     :||||||||.|.:|::...::.:||:|.||||||.||||||||||:||.
UNIPROTQ6U677   301   KHNGTPLLQTIVSAINSQPSSRELPELSADNKILFPAGHDTNIANIAGMF  350
SEQ2_mature     318   NMRWTLPGQPDNTPPGGALIFERLADKAGKQYVSVSMVYQTLEQLRAQTP  367
                     .|.|.||||||||||||||:||.:||.||:||||.|:||||:|||.|||
UNIPROTQ6U677   351   GMSWALPGQPDNTPPGGALVFERWSDKTGKKYVSVQMMYQTLAQLRNQTP  400
SEQ2_mature     368   LSLKEPAGSVQLKIPGCNDQTAEGYCPLPTFKRVVSQSEEPGCQLQ       413
                     |:|.:|||||.|||||:||||||||||||.||.|:...|:|...||
UNIPROTQ6U677   401   LTLDKPAGSVALKIPGCDDQTAEGYCPLDTFTRLAKQNELVECQ         444
```

POLYPEPTIDES HAVING PHYTASE ACTIVITY AND POLYNUCLEOTIDES ENCODING SAME

CROSS-REFERENCE TO RELATED APPLICATIONS

This application is a divisional of U.S. application Ser. No. 13/327,831 filed on Dec. 16, 2011, now allowed, which is a divisional of U.S. application Ser. No. 12/022,221 filed Jan. 30, 2008, now U.S. Pat. No. 8,101,391, which claims priority or the benefit under 35 U.S.C. 119 of European application no. 07101395 filed Jan. 30, 2007 and U.S. provisional application No. 60/887,242 filed Jan. 30, 2007, the contents of which are fully incorporated herein by reference.

REFERENCE TO SEQUENCE LISTING

This application contains a Sequence Listing in computer readable form, which is incorporated herein by reference.

REFERENCE TO DEPOSITS OF BIOLOGICAL MATERIAL

This application contains a reference to deposits of biological material which have been made at DSMZ (Deutsche Sammlung von Mikroorganismen und Zellkulturen GmbH) under the Budapest Treaty and assigned accession numbers DSM 18930, DSM 18931, and DSM 18932, which microbial deposits are incorporated herein by reference.

FIELD OF THE INVENTION

The present invention relates to isolated polypeptides having phytase activity and isolated polynucleotides encoding the polypeptides. The invention also relates to nucleic acid constructs, vectors, and host cells comprising the polynucleotides as well as methods for producing and using the polypeptides.

DESCRIPTION OF THE RELATED ART

WO 2006/043178 discloses a phytase from *Buttiauxella* P1-29 (deposited as NCIMB 41248) having the amino acid sequence of SEQ ID NO: 3 in WO 2006/043178, as well as certain variants thereof. The sequence of a *Buttiauxella* wild-type phytase and a number of variants thereof have been submitted to the GENESEQP database with the following accession numbers: AEH25051, AEH25056, AEH25057, AEH25058, AEH25059, AEH25060, AEH25061, AEH25062, AEH25063, AEH25064, AEH25065, AEH25066, AEH25067, AEH25068, AEH25069, AEH25070, AEH25071, AEH25072, AEH25073, AEH25074, AEH25075, and AEH25076. These phytases all have a percentage of identity to any one of SEQ ID NOs: 2, 4 and 6 of above 70%, however they do not comprise at least one of 119N, 120L, and/or 121E, as defined above.

The sequence of a phytase from *Obesumbacterium proteus* has been submitted to the UNIPROT database with accession number Q6U677. This phytase, which is also described by Zinin et al. (2004, *FEMS Microbiology Letters* 236: 283-290), has a percentage of identity to SEQ ID NOs: 2, 4 and 6 of above 70%, however neither does this phytase comprise at least one of 119N, 120L, and/or 121E, as defined above.

It is an object of the present invention to provide improved polypeptides having phytase activity and polynucleotides encoding the polypeptides. The phytases of the invention have an improved specific activity, an improved stability such as an improved temperature and/or pH stability, an improved pH activity profile, an improved temperature activity profile, an improved substrate profile, an improved performance in animal feed in vitro, and/or an improved performance in animal feed in vivo.

SUMMARY OF THE INVENTION

In a first aspect, the present invention relates to a polypeptide having phytase activity and having an amino acid sequence which a) has at least 70% identity to amino acids 1-413 of SEQ ID NO: 2, amino acids 1-413 of SEQ ID NO: 4, and/or amino acids 1-413 of SEQ ID NO: 6 when aligned to the respective amino acid sequence using the Needle program with the BLOSUM62 substitution matrix, a gap opening penalty of 10.0, and a gap extension penalty of 0.5; and b) comprises at least one of the following amino acids at the position indicated: 119N, 120L, and/or 121E, when aligned as described in a) to amino acids 1-413 of SEQ ID NO: 2 and using an amino acid residue numbering corresponding to amino acids 1-413 of SEQ ID NO: 2.

In a particular embodiment, the polypeptide comprises at least one of the following amino acids at the position indicated: 109Q, 111G, 119N, 120L, and/or 121E.

In another particular embodiment, the polypeptide a) has at least 78% identity, such as, at least 80% identity, at least 85% identity, at least 90% identity, at least 95% identity, at least 96% identity, at least 97% identity, at least 98% identity, at least 99% identity to amino acids 1-413 of SEQ ID NO: 2, amino acids 1-413 of SEQ ID NO: 4, and/or amino acids 1-413 of SEQ ID NO: 6; and b) comprises at least one of the following amino acids at the position indicated: 109Q, 111G, 119N, 120L, 121E, and/or 193Q.

In another aspect, the invention relates to a polypeptide having phytase activity and having an amino acid sequence which a) has at least 78% identity, such as, at least 80% identity, at least 85% identity, at least 90% identity, at least 95% identity, at least 96% identity, at least 97% identity, at least 98% identity, at least 99% identity to amino acids 1-413 of SEQ ID NO: 2, amino acids 1-413 of SEQ ID NO: 4, and/or amino acids 1-413 of SEQ ID NO: 6; and b) comprises at least one of the following amino acids at the position indicated: 1S, 10I, 38S, 66E, 71K, 81A, 109Q, 111G, 119N, 120L, 121E, 141R, 142L, 152M, 155E, 193Q, 214V, 239K, 245D, 248E, 255A,T, 268A,T, 277T, 283D,E, 285K, 287D, 288A,V, 293G, 296S, 303L, 314A, 337I, 345A, 350I, 364A, 371K, 372E, 396P, 399K, 406E, and/or 413P.

In another aspect, the invention relates to a polypeptide having phytase activity, selected from the group consisting of: (i) a polypeptide comprising a mature part of SEQ ID NO: 2 (such as the sequence of amino acids 1-413 of SEQ ID NO: 2); (ii) a variant of (i) comprising at least one of the following substitutions: K26E, N37Y, A89T, D92E, T134I,V, H160R, S164F, T171I, T176K, A178P, S188N, D190E, A192G, K207E,T, A209S, D211C, A235V, E248L, Q256H,Y, A261E, N270K, D283N, A288E, I303F, and/or N318D; and (iii) a variant of (i) or (ii) comprising at least one of the following substitutions: N1S, V9I, T38S, E66Q, Q71K, T81A, R141Q, L142V, T152M, E155D, V214I, K239N, D245E, E248S, A255T, R268A,T, A277T, D283E, N285K, T287D, A288V, D293G, P296S, I303L, S314A, I337V, A345S, V350I, A364S, K371N, E372Q, P396S, K399T, E406V, and/or Q413P.

In another aspect, the invention relates to a polypeptide having phytase activity, selected from the group consisting of: (i) a polypeptide comprising a mature part of SEQ ID NO: 4

(such as the sequence of amino acids 1-413 of SEQ ID NO: 4); (ii) a variant of (i) comprising at least one of the following substitutions: K26E, N37Y, A89T, D92E, T134I,V, H160R, S164F, T171I, T176K, A178P, S188N, D190E, A192G, K207E,T, A209S, D211C, A235V, S248L, Q256H,Y, A261E, N270K, E283N, V288E, I303F, and/or N318D; and (iii) a variant of (i) or (ii) comprising at least one of the following substitutions: S1N, I9V, S38T, Q66E, K71Q, T81A, Q141R, V142L, M152T, E155D, I214V, N239K, E245D, S248E, T255A, A268R,T, T277A, E283D, K285N, D287T, V288A, D293G, S296P, I303L, A314S, V337I, S345A, I350V, A364S, N371K, E372Q, S396P, T399K, V406E, and/or P413Q.

Yet another aspect of the invention relates to a polypeptide having phytase activity, selected from the group consisting of: (i) a polypeptide comprising a mature part of SEQ ID NO: 6 (such as the sequence of amino acids 1-413 of SEQ ID NO: 6); (ii) a variant of (i) comprising at least one of the following substitutions: K26E, N37Y, A89T, D92E, T134I,V, H160R, S164F, T171I, T176K, A178P, S188N, D190E, A192G, K207E,T, A209S, D211C, A235V, S248L, Q256H,Y, A261E, N270K, E283N, V288E, L303F, and/or N318D; and (iii) a variant of (i) or (ii) comprising at least one of the following substitutions: N1S, V9I, T38S, E66Q, Q71K, A81T, Q141R, V142L, T152M, D155E, I214V, N239K, E245D, S248E, A255T, T268A,R, T277A, E283D, K285N, D287T, V288A, G293D, P296S, L303I, A314S, V337I, S345A, V350I, S364A, N371K, Q372E, S396P, T399K, V406E, and/or Q413P.

Another aspect of the invention is directed to a phytase which has an amino acid sequence which has at least 80% identity, such as, at least 85% identity, at least 90% identity, at least 95% identity, at least 96% identity, at least 97% identity, at least 98% identity, at least 99% identity, to amino acids 1-413 of SEQ ID NO: 2, amino acids 1-413 of SEQ ID NO: 4, or amino acids 1-413 of SEQ ID NO: 6.

In another aspect, the present invention is directed to a phytase variant which has an amino acid sequence which has at least 70% identity, at least 75% identity, at least 80% identity, such as, at least 85% identity, at least 90% identity, at least 95% identity, at least 96% identity, at least 97% identity, at least 98% identity, at least 99% identity to a polypeptide comprising a mature part (such as the sequence of amino acids 34-446) of any one of the following GENESEQP sequences: AEH25057, AEH25059, AEH25058, AEH25067, AEH25071, AEH25072, AEH25074, AEH25076, AEH25073, AEH25070, AEH25069, AEH25066, AEH25060, AEH25068, AEH25063, AEH25065, AEH25062, AEH25061, AEH25056, AEH25051, or AEH25064; which variant has phytase activity and comprises at least one of the following substitutions: N1S, V10I, T38S, Q66E, Q71K, T81A, E109Q, H111G, D119N, I120L, K121E, Q141R, V142L, T152M, D155E, L193Q, I214V, N239K, E245D, S248E, V255A,T, R268A,T, A277T, N283D,E, N285K, T287D, E288A,V, D293G, P296S, I303L, A314S, V337I, S345A, V350I, S364A, N371K, Q372E, S396P, T399K, V406E, and/or Q413P.

In a particular embodiment, the invention relates to a variant of a polypeptide comprising a mature part (such as the sequence of amino acids 34-446) of GENESEQP: AEH25075, which variant has phytase activity and comprises at least one of the following substitutions: N1S, V10I, T38S, Q66E, Q71K, T81A, E109Q, H111G, D119N, I120L, K121E, Q141R, V142L, T152M, D155E, L193Q, I214V, N239K, E245D, S248E, V255A,T, R268A,T, A277T, N283D,E, N285K, T287D, E288A,V, D293G, P296S, F303L, A314S, V337I, S345A, V350I, S364A, N371K, Q372E, S396P, T399K, V406E, and/or Q413P.

In each of these aspects, for calculating identity and determining amino acid residue positions, an alignment is produced as described under the first aspect above.

The invention also relates to polynucleotides encoding these polypeptides, as well as nucleic acid constructs, recombinant expression vectors, and recombinant host cells comprising the polynucleotides, and to methods for producing and using these polypeptides.

Another aspect of the present invention relates to animal feed compositions comprising a phytase of the present invention. The present invention also provides methods for improving the nutritional value of an animal feed using a phytase of the present invention.

Another aspect of the present invention relates to methods for treating proteins, including vegetable proteins, with a phytase of the present invention.

Yet another aspect of the present invention relates to the methods for producing a fermentation product, such as, e.g., ethanol, beer, wine, wherein the fermentation is carried out in the presence of a phytase of the present invention.

BRIEF DESCRIPTION OF THE FIGURES

FIG. 1 shows a multiple alignment of the expected mature parts of SEQ ID NO: 2, SEQ ID NO: 4 and SEQ ID NO: 6 of the invention together with the sequences with the following GENESEQP accession numbers: AEH25051 (SEQ ID NO: 27), AEH25056 (SEQ ID NO: 28), AEH25057 (SEQ ID NO: 29), AEH25058 (SEQ ID NO: 30), AEH25059 (SEQ ID NO: 31), AEH25060 (SEQ ID NO: 32), AEH25061 (SEQ ID NO: 33), AEH25062 (SEQ ID NO: 34), AEH25063 (SEQ ID NO: 35), AEH25064 (SEQ ID NO: 36), AEH25065 (SEQ ID NO: 37), AEH25066 (SEQ ID NO: 38), AEH25067 (SEQ ID NO: 39), AEH25068 (SEQ ID NO: 40), AEH25069 (SEQ ID NO: 41), AEH25070 (SEQ ID NO: 42), AEH25071 (SEQ ID NO: 43), AEH25072 (SEQ ID NO: 44), AEH25073 (SEQ ID NO: 45), AEH25074 (SEQ ID NO: 46), AEH25075 (SEQ ID NO: 47), and AEH25076 (SEQ ID NO: 48). The alignment was made using the Clustal method (Higgins, 1989, CABIOS 5: 151-153) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters are Ktuple=1, gap penalty=3, windows=5, and diagonals=5.

FIG. 2 shows an alignment of UNIPROT accession no. Q6U677 (SEQ ID NO: 49) with amino acids 1-413 of SEQ ID NO: 2. The alignment was made using the program needle with the matrix BLOSUM62, a gap initiation penalty of 10.0 and a gap extension penalty of 0.5.

DETAILED DESCRIPTION OF THE INVENTION

Structural Considerations

The structures of three phytases of the invention (mature part of SEQ ID NOs: 2, 4 and 6) were built by homology modelling, using as a template the structure of the *E. coli* AppA phytase (Protein Data Bank id.: 1DKN; Lim et al., 2000, *Nat. Struct. Biol.* 2: 108-113).

Positions 119 to 121 are facing the active site cleft and therefore the specific amino acids in these positions are expected to have an effect on specific activity. For increasing the specific activity, 119N is estimated as the better choice, followed by 121E, and finally 120L.

Positions 109 and 111 are close to a disulfide in a region which is a bit stressed, so the specific amino acids in these positions are expected to have an effect on stability, on thermostability in particular. 111G may be better than 109Q.

Position 193 is another region which may influence the stability of the enzyme. 193Q may provide a good stability.

Corresponding phytase variants, and other phytase variants (e.g., a variant comprising a conservative substitution, deletion, and/or insertion of one or more amino acids of amino acids), may be prepared by methods known in the art and tested as described in the experimental part.

Phytase Polypeptides, Percentage of Identity

In the present context a phytase is a polypeptide having phytase activity, i.e., an enzyme which catalyzes the hydrolysis of phytate (myo-inositol hexakisphosphate) to (1) myo-inositol and/or (2) mono-, di-, tri-, tetra- and/or penta-phosphates thereof and (3) inorganic phosphate.

In the present context the term a phytase substrate encompasses, i.a., phytic acid and any phytate (salt of phytic acid), as well as the phosphates listed under (2) above.

The ENZYME site at the internet (expasy.ch/enzyme/) is a repository of information relative to the nomenclature of enzymes. It is primarily based on the recommendations of the Nomenclature Committee of the International Union of Biochemistry and Molecular Biology (IUB-MB) and it describes each type of characterized enzyme for which an EC (Enzyme Commission) number has been provided (Bairoch, The ENZYME database, 2000, *Nucleic Acids Res.* 28: 304-305). See also the handbook Enzyme Nomenclature from NC-IUBMB, 1992).

According to the ENZYME site, three different types of phytases are known: A so-called 3-phytase (alternative name 1-phytase; a myo-inositol hexaphosphate 3-phosphohydrolase, EC 3.1.3.8), a so-called 4-phytase (alternative name 6-phytase, name based on 1L-numbering system and not 1D-numbering, EC 3.1.3.26), and a so-called 5-phytase (EC 3.1.3.72). For the purposes of the present invention, all three types are included in the definition of phytase.

In a particular embodiment, the phytases of the invention belong to the family of acid histidine phosphatases, which includes the *Escherichia coli* pH 2.5 acid phosphatase (gene appA) as well as fungal phytases such as *Aspergillus awamorii* phytases A and B (EC: 3.1.3.8) (gene phyA and phyB). The histidine acid phosphatases share two regions of sequence similarity, each centered around a conserved histidine residue. These two histidines seem to be involved in the enzymes' catalytic mechanism. The first histidine is located in the N-terminal section and forms a phosphor-histidine intermediate while the second is located in the C-terminal section and possibly acts as proton donor.

In a further particular embodiment, the phytases of the invention have a conserved active site motif, viz., R-H-G-V-R-A-P (see amino acids 18 to 24 of SEQ ID NOs: 2, 4, and 6).

For the purposes of the present invention the phytase activity is determined in the unit of FYT, one FYT being the amount of enzyme that liberates 1 micro-mol inorganic orthophosphate per min. under the following conditions: pH 5.5; temperature 37° C.; substrate: sodium phytate ($C_6H_6O_{24}P_6Na_{12}$) in a concentration of 10.8 mmol/l. Phytase activity is preferably determined using the assay of Example 3 herein. Other suitable phytase assays are the FYT and FTU assays described in Example 1 of WO 00/20569. FTU is for determining phytase activity in feed and premix.

In a particular embodiment the phytase of the invention is isolated. The term "isolated" as used herein refers to a polypeptide which is at least 20% pure, preferably at least 40% pure, more preferably at least 60% pure, even more preferably at least 80% pure, most preferably at least 90% pure, and even most preferably at least 95% pure, such as, at least 96%, 97%, 98%, 99% and higher purity, as determined by SDS-PAGE. In particular, it is preferred that the polypeptides are in "essentially pure form", i.e., that the polypeptide preparation is essentially free of other polypeptide material with which it is natively associated. This can be accomplished, for example, by preparing the polypeptide by means of well-known recombinant methods and/or by classical purification methods.

When used herein the term "mature part" refers to that part of the polypeptide which is secreted by a cell which contains, as part of its genetic equipment, a polynucleotide encoding the polypeptide. Generally, the mature polypeptide part refers to that part of the polypeptide which remains after the N-terminal signal peptide part is cleaved off once it has fulfilled its function of directing the encoded polypeptide into the cell's secretory pathway. However, experience shows that sometimes also minor C-terminal truncations occur during the secretion process. The term mature part as used herein also takes into account such C-terminal truncations, if any. The expected signal peptide parts of SEQ ID NOs: 2, 4 and 6 are amino acids −33 to −1 of SEQ ID NO: 2, −9 to −1 of SEQ ID NO: 4 (this is a partial signal peptide), and amino acids −33 to −1 of SEQ ID NO: 6 (see the sequence listing included herewith). SEQ ID NO: 8, which is encoded by SEQ ID NO: 7, is also a signal peptide. As we are not presently aware of any C-terminal truncations having occurred during secretion, the expected mature parts of SEQ ID NOs: 2, 4, and 6 are amino acids 1-413 thereof.

In various aspects of the present invention, the relatedness between two amino acid sequences is described by the parameter "identity". For purposes of the present invention, the alignment of two amino acid sequences is determined by using the Needle program from the EMBOSS package (emboss.org), preferably in version 2.8.0. The Needle program implements the global alignment algorithm described in Needleman and Wunsch, 1970, *J. Mol. Biol.* 48: 443-453. The substitution matrix used is BLOSUM62, the gap opening (initiation) penalty is 10.0, and the gap extension penalty is 0.5.

The degree of identity between an amino acid sequence of the present invention ("invention sequence") and an amino acid sequence referred to in the claims (e.g., amino acids 1-413 of SEQ ID NO: 2) is calculated as the number of exact matches in an alignment of the two sequences, divided by the length of the "invention sequence," or the length of amino acids 1-413 of SEQ ID NO: 2, whichever is the shortest. The result is expressed in percent identity.

An exact match occurs when the "invention sequence" and SEQ ID NO: 2 have identical amino acid residues in the same positions of the overlap (in the alignment example below this is represented by "I"). The length of a sequence is the number of amino acid residues in the sequence (e.g., the length of amino acids 1-413 of SEQ ID NO: 2 is 413).

In the purely hypothetical alignment example below, the overlap is the amino acid sequence "HTWGER-NL" of Sequence 1 (SEQ ID NO: 50); or the amino acid sequence "HGWGEDANL" of Sequence 2 (SEQ ID NO: 51). In the example a gap is indicated by a "-".

Hypothetical alignment example:

```
Sequence 1: ACMSHTWGER-NL      (SEQ ID NO: 50)
              | ||| ||
Sequence 2:     HGWGEDANLAMNPS (SEQ ID NO: 51)
```

In a particular embodiment, the percentage of identity of an amino acid sequence of a polypeptide with, or to, e.g., amino acids 1-413 of SEQ ID NO: 2 is determined by i) aligning the two amino acid sequences using the Needle program, with the BLOSUM62 substitution matrix, a gap opening penalty of 10.0, and a gap extension penalty of 0.5; ii) counting the number of exact matches in the alignment; iii) dividing the number of exact matches by the length of the shortest of the two amino acid sequences, and iv) converting the result of the division of iii) into percentage.

In the above hypothetical example, the number of exact matches is 6, the length of the shortest one of the two amino acid sequences is 12; accordingly the percentage of identity is 50%.

Another example of an alignment is shown in FIG. 2, where the phytase from Obesumbacterium proteus (UNIPROT:Q6U677) is aligned with amino acids 1-413 of SEQ ID NO: 2. From this alignment it appears that the percentage of identity of UNIPROT:Q6U677 to amino acids 1-413 of SEQ ID NO: 2 is 76.3% (315 exact matches, the length of the shortest sequence is 413).

In particular embodiments of the phytase of the invention (i.e., according to any one of the various aspects thereof), the degree of identity to any one of amino acids 1-413 of SEQ ID NO: 2, amino acids 1-413 of SEQ ID NO: 4, and amino acids 1-413 of SEQ ID NO: 6 is at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99%. In still further particular embodiments, the degree of identity is at least 90.0%, 90.2%, 90.4%, 90.6%, 90.8%, 91.0%, 91.2%, 91.4%, 91.6%, 91.8%, 92.0%, 92.2%, 92.4%, 92.6%, 92.8%, 93.0%, 93.2%, 93.4%, 93.6%, 93.8%, 94.0%, 94.2%, 94.4%, 94.6%, 94.8%, 95.0%, 95.2%, 95.4%, 95.6%, 95.8%, 96.0%, 96.2%, 96.4%, 96.6%, 96.8%, 97.0%, 97.2%, 97.4%, 97.6%, 97.8%, 98.0%, 98.2%, 98.4%, 98.6%, 98.8%, 99.0%, 99.2%, 99.4%, 99.6%, or at least 99.8%.

In still further particular embodiments, the phytase of the invention has (or has an amino acid sequence which differs by) no more than 1, 2, 3, 4, 5, 6, 7, 8, 9, or no more than 10 alterations as compared to any one of amino acids 1-413 of SEQ ID NO: 2, amino acids 1-413 of SEQ ID NO: 4, and amino acids 1-413 of SEQ ID NO: 6; no more than 11, 12, 13, 14, 15, 16, 17, 18, 19, or no more than 20 alterations as compared to any one of amino acids 1-413 of SEQ ID NO: 2, amino acids 1-413 of SEQ ID NO: 4, and amino acids 1-413 of SEQ ID NO: 6; no more than 21, 22, 23, 24, 25, 26, 27, 28, 29, or no more than 30 alterations as compared to any one of amino acids 1-413 of SEQ ID NO: 2, amino acids 1-413 of SEQ ID NO: 4, and amino acids 1-413 of SEQ ID NO: 6; no more than 31, 32, 33, 34, 35, 36, 37, 38, 39, or no more than 40 alterations as compared to any one of amino acids 1-413 of SEQ ID NO: 2, amino acids 1-413 of SEQ ID NO: 4, and amino acids 1-413 of SEQ ID NO: 6; no more than 41, 42, 43, 44, 45, 46, 47, 48, 49, or no more than 50 alterations as compared to any one of amino acids 1-413 of SEQ ID NO: 2, amino acids 1-413 of SEQ ID NO: 4, and amino acids 1-413 of SEQ ID NO: 6; no more than 51, 52, 53, 54, 55, 56, 57, 58, 59, or no more than 60 alterations as compared to any one of amino acids 1-413 of SEQ ID NO: 2, amino acids 1-413 of SEQ ID NO: 4, and amino acids 1-413 of SEQ ID NO: 6; no more than 61, 62, 63, 64, 65, 66, 67, 68, 69, or no more than 70 alterations as compared to any one of amino acids 1-413 of SEQ ID NO: 2, amino acids 1-413 of SEQ ID NO: 4, and amino acids 1-413 of SEQ ID NO: 6; no more than 71, 72, 73, 74, 75, 76, 77, 78, 79, or no more than 80 alterations as compared to any one of amino acids 1-413 of SEQ ID NO: 2, amino acids 1-413 of SEQ ID NO: 4, and amino acids 1-413 of SEQ ID NO: 6; no more than 81, 82, 83, 84, 85, 86, 87, 88, 89, or no more than 90 alterations as compared to any one of amino acids 1-413 of SEQ ID NO: 2, amino acids 1-413 of SEQ ID NO: 4, and amino acids 1-413 of SEQ ID NO: 6; no more than 91, 92, 93, 94, 95, 96, 97, 98, 99, or no more than 100 alterations as compared to any one of amino acids 1-413 of SEQ ID NO: 2, amino acids 1-413 of SEQ ID NO: 4, and amino acids 1-413 of SEQ ID NO: 6; no more than 101, 102, 103, 104, 105, 106, 107, 108, 109, or no more than 110 alterations as compared to any one of amino acids 1-413 of SEQ ID NO: 2, amino acids 1-413 of SEQ ID NO: 4, and amino acids 1-413 of SEQ ID NO: 6; no more than 111, 112, 113, 114, 115, 116, 117, 118, 119, or no more than 120 alterations as compared to any one of amino acids 1-413 of SEQ ID NO: 2, amino acids 1-413 of SEQ ID NO: 4, and amino acids 1-413 of SEQ ID NO: 6; or no more than 121, 122, 123, or 124 alterations as compared to any one of amino acids 1-413 of SEQ ID NO: 2, amino acids 1-413 of SEQ ID NO: 4, and amino acids 1-413 of SEQ ID NO: 6.

In alternative embodiments of the phytase of the invention, the degree of identity to any one of amino acids 1-413 of SEQ ID NO: 2, amino acids 1-413 of SEQ ID NO: 4, and amino acids 1-413 of SEQ ID NO: 6 is at least 55%, 56%, 57%, 58%, 59%, 60%, 61%, 62%, 63%, 64%, 65%, 66%, 67%, 68%, or at least 69%.

Position Numbering

The nomenclature used herein (i.e., according to any one of the various aspects of the invention) for defining amino acid positions is based on the amino acid sequence of the phytase derived from Buttiauxella gaviniae DSM 18930, viz., the expected mature sequence thereof which is amino acids 1-413 of SEQ ID NO: 2. Accordingly, in the present context, the basis for numbering positions is SEQ ID NO: 2 starting with N1 and ending with Q413. This position numbering is shown as the first line in the alignment of FIG. 1 and this numbering is also shown in the alignment of FIG. 2 (the upper row of the alignment).

Alterations, such as Substitutions, Deletions, Insertions

A phytase of the invention (i.e., according to any one of the various aspects of the invention), be it a wild-type or a variant, can comprise various types of alterations relative to a template (i.e., a reference or comparative amino acid sequence such as amino acids 1-413 of SEQ ID NO: 2). An amino acid can be substituted with another amino acid; an amino acid can be deleted; an amino acid can be inserted; as well as any combination of any number of such alterations. In the present context the term "insertion" is intended to cover also N- and/or C-terminal extensions, and the term "deletion" is intended to cover also N- and/or C-terminal truncations.

The general nomenclature used herein for a single alteration is the following: XDcY, where "X" and "Y" independently designate a one-letter amino acid code, or a "*", "D" designates a number, and "c" designates an alphabetical counter (a, b, c, and so forth), which is only present in insertions. Reference is made to Table 1 below which describes purely hypothetical examples of applying this nomenclature to various types of alterations.

TABLE 1

| Type | Description | Example |
|---|---|---|
| Substitution | X = Amino acid in template<br>D = Position in template<br>c empty<br>Y = Amino acid in variant | G80A<br>80<br>AALNNSIGVLGVAPSAELYAVKVLGASGSG (SEQ ID NO: 52)<br>\|\|\|\|\|\|\|\|:\|\|\|\|\|\|\|\|\|\|\|\|\|\|\|\|\|\|\|\|<br>AALNNSIAVLGVAPSAELYAVKVLGASGSG (SEQ ID NO: 53) |
| Insertion | X = "*"<br>D = Position in template before the insertion<br>c = "a" for first insertion at this position, "b" for next, etc | *80aT *80bY *85aS<br>80      85<br>AALNNSIG..VLGVA.PSAELYAVKVLGASG (SEQ ID NO: 54)<br>\|\|\|\|\|\|\|\|   \|\|\|\|\| \|\|\|\|\|\|\|\|\|\|\|\|\|\|\|<br>AALNNSIGTYVLGVASPSAELYAVKVLGASG (SEQ ID NO: 52) |
| Deletion | X = Amino acid in template<br>D = Position in template<br>c empty<br>Y = "*" | V81*<br>80<br>AALNNSIGVLGVAPSAELYAVKVLGASGSG (SEQ ID NO: 52)<br>\|\|\|\|\|\|\|\| \|\|\|\|\|\|\|\|\|\|\|\|\|\|\|\|\|\|\|\|\|<br>AALNNSIG.LGVAPSAELYAVKVLGASGSG (SEQ ID NO: 55) |
| N-terminal extension | Insertions at position "0". | *0aA *0bT *0cG<br>1<br>...AQSVPWGISRVQ (SEQ ID NO: 56)<br>\|\|\|\|\|\|\|\|\|\|\|\|\|<br>ATGAQSVPWGISRVQ (SEQ ID NO: 57) |
| C-terminal extension | Insertions after the N-terminal amino acid. | *275aS *275Bt<br>270  275<br>ATSLGSTNLYGSGLVNAEAATR.. (SEQ ID NO: 58)<br>\|\|\|\|\|\|\|\|\|\|\|\|\|\|\|\|\|\|\|\|\|\|\|<br>ATSLGSTNLYGSGLVNAEAATRST (SEQ ID NO: 59) |

As explained above, the position number ("D") is counted from the first amino acid residue of amino acids 1-413 of SEQ ID NO: 2.

Several alterations in the same sequence are separated by "/" (slash), e.g., the designation "1*/2*/3*" means that the amino acids in position number 1, 2, and 3 are all deleted, and the designation "104A/105F" means that the amino acid in position number 104 is substituted by A, and the amino acid in position number 105 is substituted by F.

Alternative alterations are separated by "," (comma), e.g., the designation "255A,T" means that the amino acid in position 255 is substituted with A or T.

The commas used herein in various other enumerations of possibilities mean what they usually do grammatically, viz., often and/or. For example, the first comma in the listing "255A,T, 406E, and/or 413P" denotes an alternative (A or T), whereas the two next commas should be interpreted as and/or options: 255A or 255T, and/or 406E, and/or 413P.

In the present context, "at least one" (e.g., amino acids at the position indicated, or substitution) means one or more, e.g., 1, 2, 3, 4, 5, 6, 7, 8, 9, or 10 amino acids (or substitutions); or 12, 14, 15, 16, 18, 20, 22, 24, 25, 28, or 30 amino acids (or substitutions); and so on, up to a maximum number of alterations of 125, 130, 140, 150, 160, 170, 180, 190, or of 200.

A substitution or extension without any indication of what to substitute or extend with refers to the insertion of any natural, or non-natural, amino acid, except the one that occupies this position in the template.

Identifying Corresponding Position Numbers

As explained above, the mature phytase of *Buttiauxella gaviniae* DSM 18930 (SEQ ID NO: 2) is used herein as the standard for position numbering and, thereby, also for the nomenclature.

For another phytase, be it a wild-type or a variant, the position corresponding to position D in SEQ ID NO: 2 is found by aligning the two sequences as specified above in the section entitled "Phytase polypeptides, percentage of identity". From the alignment, the position in the sequence of the invention corresponding to position D of SEQ ID NO: 2 can be clearly and unambiguously identified (the two positions on top of each other in the alignment).

Here are some purely hypothetical examples derived from Table 1 above which in the third column includes a number of alignments of two sequences.

Consider the third cell in the first row of Table 1: The upper sequence is the template, the lower the variant. Position number 80 refers to amino acid residue G in the template. Amino acid A occupies the corresponding position in the variant. Accordingly, this substitution is designated G80A.

Consider now the third cell in the second row of Table 1: The upper sequence is again the template and the lower the variant. Position number 80 again refers to amino acid residue G in the template. The variant has two insertions, viz., TY, after G80 and before V81 in the template. Whereas the T and Y of course would have their own "real" position number in the variant amino acid sequence, for the present purposes we always refer to the template position numbers, and accordingly the T and the Y are said to be in position number 80a and 80b, respectively.

Finally, consider the third cell in the last row of Table 1: Position number 275 refers to the last amino acid of the template. A C-terminal extension of ST are said to be in position number 275a and 275b, respectively, although, again, of course they have their own "real" position number in the variant amino acid sequence.

A real example of such alignment is shown in FIG. 2, where the phytase from Obesumbacterium *proteus* (UNIPROT: Q6U677) is aligned with amino acids 1-413 of SEQ ID NO: 2. From this alignment it is inferred that, i.a., amino acids 119N, 120L, and 121E of SEQ ID NO: 2 correspond to 119D, 120I and 120K of UNIPROT:Q6U677, respectively.

Various Embodiments

A polypeptide according to the second aspect of the invention has an amino acid sequence which a) has at least 78% identity to amino acids 1-413 of SEQ ID NO: 2, amino acids 1-413 of SEQ ID NO: 4, and/or amino acids 1-413 of SEQ ID NO: 6; and b) comprises at least one of the following amino acids at the position indicated: 1S, 10I, 38S, 66E, 71K, 81A, 109Q, 111G, 119N, 120L, 121E, 141R, 142L, 152M, 155E, 193Q, 214V, 239K, 245D, 248E, 255A,T, 268A,T, 277T, 283D,E, 285K, 287D, 288A,V, 293G, 296S, 303L, 314A, 337I, 345A, 350I, 364A, 371K, 372E, 396P, 399K, 406E, and/or 413P.

Each of the amino acids at the positions indicated under b) above make a difference to the *Buttiauxella* NCIMB 41248 wild-type phytase and its variants with the following GENESEQP accession numbers: AEH25051, AEH25056, AEH25057, AEH25058, AEH25059, AEH25060, AEH25061, AEH25062, AEH25063, AEH25064, AEH25065, AEH25066, AEH25067, AEH25068, AEH25069, AEH25070, AEH25071, AEH25072, AEH25073, AEH25074, AEH25075, and AEH25076.

In particular embodiments thereof, the amino acid sequence comprises a) at least one of 1A, 10I, 38S, 71K, 109Q, 111G, 119N, 120L, 121E, 152M, 155E, 193Q, 255T, 268A, 277T, 283E, 285K, 287D, 288V, 296S, 364A, 350I, 372E, and/or 413P (as represented by SEQ ID NO: 4); b) at least one of 66E, 81A, 109Q, 111G, 119N, 120L, 121E, 193Q, 255A, 268T, 277T, 283E, 285K, 287D, 288V, 293G, and/or 303L (as represented by SEQ ID NO: 6); and c) at least one of 66E, 109Q, 111G, 119N, 120L, 121E, 141R, 142L, 155E, 193Q, 214V, 239K, 245D, 248E, 255A, 283D, 288A, 314S, 337I, 345A, 364A, 371K, 372E, 396P, 399K, and/or 406E (as represented by SEQ ID NO: 2).

In another particular embodiment the polypeptide of the invention has been altered inspired by the *Buttiauxella* wild-type and mutant phytases disclosed in WO 2006/043178, viz., it has an amino acid sequence which comprises at least one of the following amino acids at the position indicated: 26E, 37Y, 89T, 92E, 134I,V, 160R, 164F, 171I, 176K, 178P, 188N, 190E, 192G, 207E,T, 209S, 211C, 235V, 248L, 256H,Y, 261E, 270K, 303F, and/or 318D.

For example, the mature part of SEQ ID NO: 2 is mutated to comprise at least one of the following substitutions: K26E, N37Y, A89T, D92E, T134I,V, H160R, S164F, T171I, T176K, A178P, S188N, D190E, A192G, K207E,T, A209S, D211C, A235V, E248L, Q256H,Y, A261E, N270K, D283N, A288E, I303F, and/or N318D. Other preferred substitutions in the mature part of SEQ ID NO: 2 are inspired by SEQ ID NOs: 4 and 6: N1S, V9I, T38S, E66Q, Q71K, T81A, R141Q, L142V, T152M, E155D, V214I, K239N, D245E, E248S, A255T, R268A,T, A277T, D283E, N285K, T287D, A288V, D293G, P296S, I303L, S314A, I337V, A345S, V350I, A364S, K371N, E372Q, P396S, K399T, E406V, and/or Q413P.

As another example, the mature part of SEQ ID NO: 4 is mutated to comprise at least one of the following substitutions: K26E, N37Y, A89T, D92E, T134I,V, H160R, S164F, T171I, T176K, A178P, S188N, D190E, A192G, K207E,T, A209S, D211C, A235V, S248L, Q256H,Y, A261E, N270K, E283N, V288E, I303F, and/or N318D. Other preferred substitutions in the mature part of SEQ ID NO: 2 are inspired by SEQ ID NOs: 2 and 6: S1N, I9V, S38T, Q66E, K71Q, T81A, Q141R, V142L, M152T, E155D, I214V, N239K, E245D, S248E, T255A, A268R,T, T277A, E283D, K285N, D287T, V288A, D293G, S296P, I303L, A314S, V337I, S345A, I350V, A364S, N371K, E372Q, S396P, T399K, V406E, and/or P413Q.

As a still further example, the mature part of SEQ ID NO: 6 is mutated to comprise at least one of the following substitutions: K26E, N37Y, A89T, D92E, T134I,V, H160R, S164F, T171I, T176K, A178P, S188N, D190E, A192G, K207E,T, A209S, D211C, A235V, S248L, Q256H,Y, A261E, N270K, E283N, V288E, L303F, and/or N318D. Other preferred substitutions in the mature part of SEQ ID NO: 2 are inspired by SEQ ID NOs: 2 and 4: N1S, V9I, T38S, E66Q, Q71K, A81T, Q141R, V142L, T152M, D155E, I214V, N239K, E245D, S248E, A255T, T268A,R, T277A, E283D, K285N, D287T, V288A, G293D, P296S, L303I, A314S, V337I, S345A, V350I, S364A, N371K, Q372E, S396P, T399K, V406E, and/or Q413P.

As explained above, various aspects of the present invention relate to polypeptides "having" an amino acid sequence which has a specified degree of identity to amino acids 1-413 of SEQ ID NO: 2, amino acids 1-413 of SEQ ID NO: 4, and/or amino acids 1-413 of SEQ ID NO: 6, which have phytase activity (hereinafter "homologous polypeptides"); or to polypeptides "having" an amino acid sequence which differs by a maximum number of amino acids amino acids 1-413 of SEQ ID NO: 2, amino acids 1-413 of SEQ ID NO: 4, and amino acids 1-413 of SEQ ID NO: 6.

A polypeptide of the present invention preferably comprises any one of amino acids 1-413 of SEQ ID NO: 2, amino acids 1-413 of SEQ ID NO: 4, or amino acids 1-413 of SEQ ID NO: 6; or an allelic variant thereof; or a fragment thereof that has phytase activity.

In another preferred embodiment, a polypeptide of the present invention consists of the amino acid sequence of amino acids 1-413 of SEQ ID NO: 2, amino acids 1-413 of SEQ ID NO: 4, and amino acids 1-413 of SEQ ID NO: 6; or an allelic variant thereof; or a fragment thereof that has phytase activity.

Anyone of the nucleotide sequences of SEQ ID NO: 1, 3 and 5, or a subsequence thereof, as well as the amino acid sequences of SEQ ID NO: 2, 4, and 6, or a fragment thereof, may be used to design a nucleic acid probe to identify and clone DNA encoding polypeptides having phytase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Both DNA and RNA probes can be used. The probes are typically labelled for detecting the corresponding gene (for example, with $^{32}P$, $^3H$, $^{35}S$, biotin, or avidin).

A genomic DNA library prepared from such other organisms may, therefore, be screened for DNA which hybridizes with the probes described above and which encodes a polypeptide having phytase activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO: 1, 3 or 5 or a subsequence thereof, the carrier material is used in a Southern blot.

In a preferred embodiment, the nucleic acid probe comprises nucleotides 454-462 of SEQ ID NO: 1, nucleotides 384-392 of SEQ ID NO: 3, or nucleotides 454-462 of SEQ ID NO: 5 (all corresponding to the motif 119N, 120L, and 121E).

In another preferred aspect, the nucleic acid probe is a polynucleotide sequence which encodes the polypeptides of any one of SEQ ID Nos: 2, 4, or 6, or a subsequence thereof. In another preferred aspect, the nucleic acid probe is SEQ ID NO: 1, 3 or 5.

The present invention also relates to variants comprising a conservative substitution, deletion, and/or insertion of one or more amino acids in the sequences of amino acids 1-413 of SEQ ID NO: 2, amino acids 1-413 of SEQ ID NO: 4, or amino acids 1-413 of SEQ ID NO: 6, or the mature polypeptides thereof. Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain. A fragment is a preferred example of a variant comprising a deletion, as described above, and a fragment preferably retains phytase activity.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter specific activity are known in the art and are described, for example, by Neurath and Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type polypeptide. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

Essential amino acids in the parent polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for biological activity (i.e., phytase activity) to identify amino acid residues that are critical to the activity of the molecule. See also, Hilton et al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labelling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309: 59-64. The identities of essential amino acids can also be inferred from analysis of identities with polypeptides which are related to a polypeptide according to the invention.

Single or multiple amino acid substitutions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, Proc. Natl. Acad. Sci. USA 86: 2152-2156; WO 95/17413; or WO 95/22625. Other methods that can be used include error-prone PCR, phage display (e.g., Lowman et al., 1991, Biochem. 30: 10832-10837; U.S. Pat. No. 5,223,409; WO 92/06204), and region-directed mutagenesis (Derbyshire et al., 1986, Gene 46: 145; Ner et al., 1988, DNA 7: 127).

Mutagenesis/shuffling methods can be combined with high-throughput, automated screening methods to detect activity of cloned, mutagenized polypeptides expressed by host cells. Mutagenized DNA molecules that encode active polypeptides can be recovered from the host cells and rapidly sequenced using standard methods in the art. These methods allow the rapid determination of the importance of individual amino acid residues in a polypeptide of interest, and can be applied to polypeptides of unknown structure.

A polypeptide of the present invention may be obtained from microorganisms of any genus. For purposes of the present invention, the term "obtained from" as used herein in connection with a given source shall mean that the polypeptide encoded by a nucleotide sequence is produced by the source or by a strain in which the nucleotide sequence from the source has been inserted. In a preferred aspect, the polypeptide obtained from a given source is secreted extracellularly.

A polypeptide of the present invention may be a bacterial polypeptide. In particular embodiments, the polypeptide is obtainable from the Proteobacteria; Gammaproteobacteria; Enterobacteriales; family of Enterobacteriaceae; preferably from the genus *Buttiauxella*, e.g., selected from amongst the species of *Buttiauxella agrestis*, *Buttiauxella brennerae*, *Buttiauxella ferragutiae*, *Buttiauxella gaviniae*, *Buttiauxella izardii*, *Buttiauxella noackiae*, *Buttiauxella warmboldiae*, *Buttiauxella* sp. B22, *Buttiauxella* sp. BTN01, *Buttiauxella* sp. LBV 449, *Buttiauxella* sp. P5, *Buttiauxella* sp. PNBS, *Buttiauxella* sp. S212, *Buttiauxella* sp. S215, *Buttiauxella* sp. S218.

In a more preferred aspect, the polypeptide is a *Buttiauxella gaviniae* or *Buttiauxella agrestis* polypeptide, most preferably a *Buttiauxella gaviniae* DSM 18930, a *Buttiauxella agrestis* DSM 18931, or a *Buttiauxella agrestis* DSM 18932 polypeptide.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The polynucleotide may then be obtained by similarly screening a genomic or cDNA library of another microorganism. Once a polynucleotide sequence encoding a polypeptide has been detected with the probe(s), the polynucleotide can be isolated or cloned by utilizing techniques which are well known to those of ordinary skill in the art (see, e.g., Sambrook et al., 1989, supra).

Polypeptides of the present invention also include fused polypeptides or cleavable fusion polypeptides in which another polypeptide is fused at the N-terminus or the C-terminus of the polypeptide or fragment thereof. A fused polypeptide is produced by fusing a nucleotide sequence (or a portion thereof) encoding another polypeptide to a nucleotide sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

Altered Properties

In a particular embodiment of any aspect of the invention the phytase has altered, preferably improved, properties. Examples of altered, preferably improved, properties are pI, temperature and/or pH stability, pH activity profile, temperature activity profile, substrate profile, and performance in animal feed in vitro or in vivo.

The terms "altered", "amended" and "improved" imply a comparison with another phytase. Examples of such other, reference, or comparative, phytases are the *Buttiauxella* NCIMB 41248 wild-type phytase and its variants with the following GENESEQP accession numbers: AEH25051, AEH25056, AEH25057, AEH25058, AEH25059, AEH25060, AEH25061, AEH25062, AEH25063, AEH25064, AEH25065, AEH25066, AEH25067, AEH25068, AEH25069, AEH25070, AEH25071, AEH25072, AEH25073, AEH25074, AEH25075, and AEH25076.

The phytases of the invention which comprise at least one of the following amino acids at the position indicated: 119N, 120L, and/or 121E have an improved specific activity as shown in the experimental part. In particular embodiments, the phytase of the invention comprises i) 119N; ii) 121E; iii) 120L; iv) 119N and 121E; v) 119N and 120L; vi) 121E and 120L; or vii) 119N, 120L, and 121E. In still further particular embodiments the phytases of i)-vii) have an improved specific activity. Specific activity is determined as described below.

The phytases of the invention which comprise at least one of the following amino acids at the position indicated: 109Q, and/or 111G are expected to have an improved stability, in particular an improved thermostability. In particular embodiments, the phytase of the invention comprises i) 111G; ii) 109Q; or iii) 111G and 109Q. In still further particular embodiments the phytases of i)-iii) have an improved stability, preferably an improved thermostability. Thermostability is determined as described below.

The phytases of the invention which comprise 193Q are also expected to have an improved stability, preferably an improved thermostability. Thermostability is determined as described below.

Additional specific amino acids at specified positions, as well as additional specific amino acid substitutions are also disclosed herein, which characterize and distinguish additional phytases of the invention which may have improved properties such as pI, temperature stability, pH stability, pH activity profile, temperature activity profile, substrate profile, and/or improved performance in animal feed in vitro or in vivo.

Specific Activity

In a particular embodiment, the phytase of the invention has an improved specific activity relative to a reference phytase. More in particular, the specific activity of a phytase of the invention is at least 105%, relative to the specific activity of a reference phytase determined by the same procedure. In still further particular embodiments, the relative specific activity is at least 110, 115, 120, 125, 130, 140, 145, 150, 160, 170, 180, 190, 200, 220, 240, 260, 280, 300, 350 or even 400%, still relative to the specific activity of the reference phytase as determined by the same procedure.

Examples of reference phytases are listed above. Preferred reference phytases for this embodiment are GENESEQP: AEH25072 (the variant disclosed in Table 3 of WO 2006/043178), and GENESEQP:AEH25051 (the wild-type phytase from *Buttiauxella* P1-29 disclosed in Example 10 of WO 2006/043178).

In the alternative, the term high specific activity refers to a specific activity of at least 240 FYT/mg Enzyme Protein (EP). In particular embodiments, the specific activity is at least 300, 350, 400, 450, 500, 550, 600, or at least 650 FYT/mg EP.

Specific activity is measured on highly purified samples (an SDS poly acryl amide gel should show the presence of only one component). Preferably, the sample of the enzyme is at least 95% pure, as determined by SDS-PAGE. The enzyme protein concentration may be determined by amino acid analysis, and the phytase activity in the units of FYT, determined as described in Example 3, i.e., on the substrate of sodium phytate at pH 5.5 and 37° C. Specific activity is a characteristic of the specific phytase in question, and it is calculated as the phytase activity measured in FYT units per mg phytase variant enzyme protein. See Example 4 for further details.

Isoelectric Point (pI)

In particular embodiments, the pI for the phytase of the invention is in the range of i) 7.0-8.0; ii) 7.2-7.8; or iii) 7.4-7.6. The pI is determined as described in Example 5.

pH profile

In a particular embodiment, the phytase of the invention has an altered pH profile as compared to a reference phytase. Examples of reference phytases are listed above.

In particular embodiments, the phytase of the invention has a relative activity at pH 2.0 which is at least 30% of the activity at pH 4.5 (optimum pH), preferably at least 31%, 32%, 33%, 34%, 35%, 36%, 37%, 38%, 39%, 40%, or at least 41%.

In additional particular embodiments, the phytase of the invention has a relative activity at pH 6.0 which is at least 10% of the activity at pH 4.5 (optimum pH), preferably at least 15%, 20%, 25%, 30%, 35%, 36%, 37%, 38%, 39%, 40%, 41%, 42%, or at least 43%.

The pH profile (phytase activity as a function of pH) is determined on highly purified samples (an SDS poly acryl amide gel should show the presence of only one component). Preferably, the sample of the enzyme is at least 95% pure, as determined by SDS-PAGE. The phytase activity is determined in the pH range of 2.0 to 7.5 using a buffer cocktail (50 mM glycine, 50 mM acetic acid and 50 mM Bis-Tris(Bis-(2-hydroxyethyl)imino-tris(hydroxymethyl)methan), and on the substrate of sodium phytate at pH 5.5 and 37° C. A preferred assay is the assay of Example 3, except that the buffer is replaced with the above indicated buffer. More details are found in Example 6.

pH Stability

In a particular embodiment, the phytase of the invention has an altered pH stability as compared to a reference phytase. Examples of reference phytases are listed above.

In particular embodiments, the phytase of the invention has a residual phytase activity after incubation for 1½ hours at 40° C. and at pH selected from 2.0, 3.0, 4.0, 5.0, 6.0, 7.0, and 8.0 of at least 50%, preferably at least 55%, 60%, 65%, 70%, 75%, 80%, 82%, 84%, 86%, 90%, 92%, or at least 94%, relative to the phytase activity at 0 hours (before start of the incubation). In preferred embodiments, the incubation pH is i) 2.0, ii) 3.0, iii) 4.0, iv) 5.0, v) 6.0, vi) 7.0, and vii) 8.0. In even more preferred embodiments, the incubation pH is 2.0, and the residual activity is at least 50%, 55%, 60%, 65%, 70%, 75%, 80%, or at least 82%. The phytase is incubated in 0.1 M glycine, 0.1 M acetic acid, 0.1 M Bis-Tris, adjusted to the desired pH. The phytase activity is determined on the substrate of sodium phytate at pH 5.5 and 37° C. The activity assay of Example 3 where the buffer is replaced with the above indicated buffer is a preferred assay. More details are found in Example 7.

In still further particular embodiments, the phytase of the invention has a residual phytase activity after incubation for 24 hours at 40° C. and at pH selected from 2.0, 3.0, 4.0, 5.0, 6.0, 7.0, and 8.0 of at least 50%, preferably at least 51%, 52%, 54%, 56%, 58%, 60%, 62%, 64%, 66%, 68%, 70%, 72%, 73%, 74%, 75%, 76%, 77%, 78%, 79%, 80%, 82%, 84%, 86%, or at least 88%, relative to the phytase activity at 0 hours (before start of the incubation). In preferred embodiments, the incubation pH is i) 2.0, ii) 3.0, iii) 4.0, iv) 5.0, v) 6.0, vi) 7.0, and vii) 8.0. In even more preferred embodiments, the incubation pH is 2.0, and the residual activity is at least 50%, 51%, 52%, 54%, or at least 56%. The phytase is incubated in 0.1 M glycine, 0.1 M acetic acid, 0.1 M Bis-Tris, adjusted to the desired pH. The phytase activity is determined on the substrate of sodium phytate at pH 5.5 and 37° C. The activity assay of Example 3 where the buffer is replaced with the above indicated buffer is a preferred assay. More details are found in Example 7.

Temperature Profile

In a particular embodiment, the phytase of the invention has an altered temperature profile as compared to a reference phytase. Examples of reference phytases are listed above.

In particular embodiments, the phytase of the invention has a relative activity at 30° C. which is at least 20% of the activity at 60° C. (optimum temperature), preferably at least 22%, 24%, 26%, 28%, 30%, 32%, 34%, 36%, 38%, or at least 40%.

In additional particular embodiments, the phytase of the invention has a relative activity at 70° C. which is at least 10% of the activity at 60° C. (optimum temperature), preferably at least 12%, 14%, 16%, 18%, 20%, 22%, or at least 23%.

The temperature profile (phytase activity as a function of temperature) is determined on highly purified samples (an SDS poly acryl amide gel should show the presence of only one component). Preferably, the sample of the enzyme is at least 95% pure, as determined by SDS-PAGE. The phytase activity is determined in the temperature range of 20-90° C. at pH 4.0, in the alternative at pH 5.5. In both cases a 0.25 M sodium acetate buffer is used. The activity is determined on the substrate of sodium phytate. A preferred assay is the assay of Example 3, except of course that the temperature differs, and if desired also the pH, cf. above. More details are found in Example 8.

Thermostability

In a particular embodiment, the phytase of the invention has an altered, preferably improved, thermostability as compared to a reference phytase. Examples of reference phytases are listed above.

In particular embodiments, the phytase of the invention has a residual phytase activity after incubation for a desired time (such as 15 minutes, 30 minutes, 1 hour, 1½ hours, or 2 hours) at an elevated temperature (such as 65, 70, 75, 80, 85, 90, or 95° C.) at pH 4.5 of at least 50%, preferably at least 55%, 60%, 65%, 70%, 75%, 80%, 82%, 84%, 86%, 90%, 92%, or at least 94%, relative to the phytase activity at 0 hours (before start of the incubation). In a preferred embodiment, the incubation time is 1 hour, the pH is 4.5 and the temperature 80° C. The phytase is incubated in 0.25 M sodium acetate. The phytase activity is determined on the substrate of sodium phytate at pH 5.5 and 37° C. The activity assay of Example 3 is a preferred assay.

In the alternative, Differential Scanning calorimetry (DSC) measurements may be used to determine the denaturation temperature, Td, of the purified phytase protein. The Td is indicative of the thermostability of the protein: The higher the Td, the higher the thermostability. DSC measurements may be performed at various pH values, e.g., using the VP-DSC from Micro Cal. Scans are performed at a constant scan rate of 1.5° C./min from 20-90° C. Preferred pH values are 4.0 and 5.5, preferably 4.0. Before running the DSC, the phytases are desalted, e.g., using NAP-5 columns (Pharmacia) equilibrated in appropriate buffers (e.g., 25 mM sodium acetate pH 4.0; 0.1 M sodium acetate, pH 5.5). Data-handling is performed using the MicroCal Origin software (version 4.10), and the denaturation temperature, Td (also called the melting temperature, Tm) is defined as the temperature at the apex of the peak in the thermogram.

In particular embodiments, the phytase of the invention has a Td, which may be determined as described above, of at least 60° C. In still further particular embodiments, the Td is at least 61, 62, 64, 66, 68, 70, 72, 74, 76, 78, or at least 80° C.

Performance in Animal Feed

In a particular embodiment the phytase of the invention has an improved performance in animal feed as compared to a reference phytase. Examples of reference phytases are listed above.

The performance in animal feed may be determined using an in vitro model simulating the gastro-intestinal conditions in a monogastric animal, e.g., as follows:

Feed samples composed of 30% soybean meal and 70% maize meal with added $CaCl_2$ to a concentration of 5 g calcium per kg feed are prepared and pre-incubated at 40° C. and pH 3.0 for 30 minutes followed by addition of pepsin (3000 U/g feed) and suitable dosages of the phytases (identical dosages are used for all phytases to be tested to allow comparison), for example between 0.25 to 0.75 phytase units FYT/g feed. A blank with no phytase activity is also included as reference. The samples are then incubated at 40° C. and pH 3.0 for 60 minutes followed by pH 4.0 for 30 minutes.

The reactions are stopped and phytic acid and inositol-phosphates extracted by addition of HCl to a final concentration of 0.5 M and incubation at 40° C. for 2 hours, followed by one freeze-thaw cycle and 1 hour incubation at 40° C.

Phytic acid and inositol-phosphates are separated by high performance ion chromatography as described by Chen et al. (2003, *Journal of Chromatography A* 1018: 41-52) and quantified as described by Skoglund et al. (1997, *J. Agric. Food Chem.* 45: 431-436).

Released phosphorous is then calculated as the difference in inositol-phosphate bound phosphorous (IP-P) between phytase-treated and non-treated samples. The relative performance of a specified phytase is calculated as the percentage of the phosphorous released relative to the desired reference phytase.

In particular embodiments the relative performance in vitro of the phytase of the invention is at least 105%, preferably at least 110, 120, 130, 140, 150, 160, 170, 180, 190, or at least 200%.

Polynucleotides, Nucleic Acid Constructs, and Expression Vectors

The present invention also relates to polynucleotides comprising a nucleotide sequence which encode a polypeptide of the present invention. The polynucleotides are preferably substantially pure, or isolated, which refers to a polynucleotide preparation free of other extraneous or unwanted nucleotides and in a form suitable for use within genetically engineered protein production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99%, and even most preferably at least 99.5% pure by weight. The polynucleotides of the present invention are preferably in a substantially pure form. In particular, it is preferred that the polynucleotides disclosed herein are in "essentially pure form", i.e., that the polynucleotide preparation is essentially free of other polynucleotide material with which it is natively associated. Herein, the term "substantially pure polynucleotide" is synonymous with the terms "isolated polynucleotide" and "polynucleotide in isolated form." The polynucleotides may be of genomic, cDNA, RNA, semisynthetic, synthetic origin, or any combinations thereof.

The present invention also relates to nucleic acid constructs comprising an isolated polynucleotide of the present invention operably linked to one or more control sequences which direct the expression of the coding sequence in a suitable host cell under conditions compatible with the control sequences.

The term "nucleic acid construct" as used herein refers to a nucleic acid molecule, either single- or double-stranded, which is isolated from a naturally occurring gene or which is modified to contain segments of nucleic acids in a manner that would not otherwise exist in nature. The term nucleic acid construct is synonymous with the term "expression cassette" when the nucleic acid construct contains the control sequences required for expression of a coding sequence of the present invention.

The term "control sequences" is defined herein to include all components, which are necessary or advantageous for the expression of a polynucleotide encoding a polypeptide of the present invention. Each control sequence may be native or foreign to the nucleotide sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

The control sequence may be an appropriate promoter sequence, a nucleotide sequence which is recognized by a host cell for expression of a polynucleotide encoding a polypeptide of the present invention.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, *Proceedings of the National Academy of Sciences USA* 75: 3727-3731), as well as the tac promoter (DeBoer et al., 1983, *Proceedings of the National Academy of Sciences USA* 80: 21-25). Further promoters are described in "Useful proteins from recombinant bacteria" in *Scientific American* 1980, 242: 74-94; and in Sambrook et al., 1989, supra.

The control sequence may also be a suitable transcription terminator sequence, a sequence recognized by a host cell to terminate transcription. The terminator sequence is operably linked to the 3' terminus of the nucleotide sequence encoding the polypeptide. Any terminator which is functional in the host cell of choice may be used in the present invention.

The control sequence may also be a suitable leader sequence, a nontranslated region of an mRNA which is important for translation by the host cell. The leader sequence is operably linked to the 5' terminus of the nucleotide sequence encoding the polypeptide. Any leader sequence that is functional in the host cell of choice may be used in the present invention.

The control sequence may also be a polyadenylation sequence, a sequence operably linked to the 3' terminus of the nucleotide sequence and which, when transcribed, is recognized by the host cell as a signal to add polyadenosine residues to transcribed mRNA. Any polyadenylation sequence which is functional in the host cell of choice may be used in the present invention.

The control sequence may also be a signal peptide coding region that codes for an amino acid sequence linked to the amino terminus of a polypeptide and directs the encoded polypeptide into the cell's secretory pathway. The 5' end of the coding sequence of the nucleotide sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus*

*stearothermophilus* neutral proteases (nprT, nprS, nprM), and *Bacillus subtilis* prsA. Further signal peptides are described by Simonen and Palva, 1993, *Microbiological Reviews* 57: 109-137.

In a preferred aspect, the signal peptide coding region is nucleotides 1 to 81 of SEQ ID NO: 7 which encode amino acids 1 to 27 of SEQ ID NO: 8.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. Other examples of regulatory sequences are those which allow for gene amplification. In these cases, the nucleotide sequence encoding the polypeptide would be operably linked with the regulatory sequence.

The present invention also relates to recombinant expression vectors comprising a polynucleotide of the present invention, a promoter, and transcriptional and translational stop signals. The term "expression vector" is defined herein as a linear or circular DNA molecule that comprises a polynucleotide encoding a polypeptide of the invention, and which is operably linked to additional nucleotides that provide for its expression. The various nucleic acids and control sequences described above may be joined together to produce a recombinant expression vector which may include one or more convenient restriction sites to allow for insertion or substitution of the nucleotide sequence encoding the polypeptide at such sites. Alternatively, a nucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The term "expression" includes any step involved in the production of the polypeptide including, but not limited to, transcription, post-transcriptional modification, translation, post-translational modification, and secretion.

The recombinant expression vector may be any vector (e.g., a plasmid or virus) which can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

A vector comprising a polynucleotide of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like.

A conditionally essential gene may function as a non-antibiotic selectable marker. Non-limiting examples of bacterial conditionally essential non-antibiotic selectable markers are the dal genes from *Bacillus subtilis*, *Bacillus licheniformis*, or other Bacilli, that are only essential when the bacterium is cultivated in the absence of D-alanine. Also the genes encoding enzymes involved in the turnover of UDP-galactose can function as conditionally essential markers in a cell when the cell is grown in the presence of galactose or grown in a medium which gives rise to the presence of galactose. Non-limiting examples of such genes are those from *B. subtilis* or *B. licheniformis* encoding UTP-dependent phosphorylase (EC 2.7.7.10), UDP-glucose-dependent uridylyltransferase (EC 2.7.7.12), or UDP-galactose epimerase (EC 5.1.3.2). Also a xylose isomerase gene such as xylA, of Bacilli can be used as selectable markers in cells grown in minimal medium with xylose as sole carbon source. The genes necessary for utilizing gluconate, gntK, and gntP can also be used as selectable markers in cells grown in minimal medium with gluconate as sole carbon source. Other examples of conditionally essential genes are known in the art. Antibiotic selectable markers confer antibiotic resistance to such antibiotics as ampicillin, kanamycin, chloramphenicol, erythromycin, tetracycline, neomycin, hygromycin or methotrexate.

The vectors of the present invention preferably contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity with the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication which functions in a cell. The term "origin of replication" or "plasmid replicator" is defined herein as a nucleotide sequence that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMR1 permitting replication in *Bacillus*.

More than one copy of a polynucleotide of the present invention may be inserted into the host cell to increase production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention, which are advantageously used in the recombinant production of the polypeptides. The term "host cell", as used herein, includes any cell type which is susceptible to transformation, transfection, transduction, and the like with a nucleic acid construct comprising a polynucleotide of the present invention.

The host cell may be a unicellular microorganism, e.g., a prokaryote, or a non-unicellular microorganism, e.g., a eukaryote.

Useful unicellular microorganisms are bacterial cells such as gram positive bacteria including, but not limited to, a *Bacillus* cell, e.g., *Bacillus alkalophilus*, *Bacillus amyloliquefaciens*, *Bacillus brevis*, *Bacillus circulans*, *Bacillus clausii*, *Bacillus coagulans*, *Bacillus lautus*, *Bacillus lentus*, *Bacillus licheniformis*, *Bacillus megaterium*, *Bacillus stearothermophilus*, *Bacillus subtilis*, and *Bacillus thuringiensis*; or a *Streptomyces* cell, e.g., *Streptomyces lividans* and *Streptomyces murinus*, or gram negative bacteria such as *E. coli* and *Pseudomonas* sp. In a preferred aspect, the bacterial host cell is a *Bacillus lentus*, *Bacillus licheniformis*, *Bacillus stearothermophilus*, or *Bacillus subtilis* cell. In another preferred aspect, the *Bacillus* cell is an alkalophilic *Bacillus*.

The introduction of a vector into a bacterial host cell may, for instance, be effected by protoplast transformation (see, e.g., Chang and Cohen, 1979, *Molecular General Genetics* 168: 111-115), using competent cells (see, e.g., Young and Spizizin, 1961, *Journal of Bacteriology* 81: 823-829, or Dubnau and Davidoff-Abelson, 1971, *Journal of Molecular Biology* 56: 209-221), electroporation (see, e.g., Shigekawa and Dower, 1988, *Biotechniques* 6: 742-751), or conjugation (see, e.g., Koehler and Thorne, 1987, *Journal of Bacteriology* 169: 5771-5278).

The host cell may also be a eukaryote, such as a mammalian, insect, plant, or fungal cell.

Methods of Production

The present invention also relates to methods for producing a polypeptide of the present invention, comprising (a) cultivating a cell, which in its wild-type form is capable of producing the polypeptide, under conditions conducive for production of the polypeptide; and (b) recovering the polypeptide. Preferably, the cell is of the genus *Buttiauxella*, and more preferably *Buttiauxella agrestis* or *Buttiauxella gaviniae*.

The present invention also relates to methods for producing a polypeptide of the present invention, comprising (a) cultivating a host cell under conditions conducive for production of the polypeptide; and (b) recovering the polypeptide.

In the production methods of the present invention, the cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, Janson and Ryden, editors, VCH Publishers, New York, 1989). A typical purification scheme may include centrifugation, germ filtration, ammonium sulphate precipitation (using, e.g., 80% ammonium sulphate saturation), centrifugation, re-suspension of pellets in 50 mM sodium acetate buffer pH 4.5, filtration, dialysis against 50 mM sodium acetate buffer and cation exchange chromatography (S-sepharose, loading with 50 mM sodium acetate pH 4.5, eluting with a linear salt gradient (50 mM sodium acetate pH 4.5+1 M NaCl)).

Transgenic Plants

The present invention also relates to a transgenic plant, plant part, or plant cell which has been transformed with a nucleotide sequence encoding a polypeptide having phytase activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an antinutritive factor.

In a particular embodiment, the polypeptide is targeted to the endosperm storage vacuoles in seeds. This can be obtained by synthesizing it as a precursor with a suitable signal peptide, see Horvath et al. (2000, *PNAS* 97(4): 1914-1919.

The transgenic plant can be dicotyledonous (a dicot) or monocotyledonous (a monocot) or engineered variants thereof. Examples of monocot plants are grasses, such as meadow grass (blue grass, *Poa*), forage grass such as *Festuca*, *Lolium*, temperate grass, such as *Agrostis*, and cereals, e.g., wheat, oats, rye, barley, rice, sorghum, triticale (stabilized hybrid of wheat (Triticum) and rye (Secale), and maize (corn). Examples of dicot plants are tobacco, legumes, such as sunflower (Helianthus), cotton (Gossypium), lupins, potato, sugar beet, pea, bean and soybean, and cruciferous plants (family Brassicaceae), such as cauliflower, rape seed, and the closely related model organism *Arabidopsis thaliana*. Low-phytate plants as described, e.g., in U.S. Pat. Nos. 5,689, 054 and 6,111,168 are examples of engineered plants.

Examples of plant parts are stem, callus, leaves, root, fruits, seeds, and tubers, as well as the individual tissues comprising these parts, e.g., epidermis, mesophyll, parenchyma, vascular tissues, meristems. Also specific plant cell compartments, such as chloroplast, apoplast, mitochondria, vacuole, peroxisomes, and cytoplasm are considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats.

Also included within the scope of the present invention are the progeny of such plants, plant parts and plant cells.

The transgenic plant or plant cell expressing a polypeptide of the present invention may be constructed in accordance with methods known in the art. Briefly, the plant or plant cell is constructed by incorporating one or more expression constructs encoding a polypeptide of the present invention into the plant host genome and propagating the resulting modified plant or plant cell into a transgenic plant or plant cell.

Conveniently, the expression construct is a nucleic acid construct which comprises a nucleic acid sequence encoding a polypeptide of the present invention operably linked with appropriate regulatory sequences required for expression of the nucleic acid sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences are determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific cell compartment, tissue or plant part such as seeds or leaves. Regulatory sequences are, for example, described by Tague et al., 1988, *Plant Physiology* 86: 506.

For constitutive expression, the following promoters may be used: The 35S-CaMV promoter (Franck et al., 1980, *Cell* 21: 285-294), the maize ubiquitin 1 (Christensen, Sharrock and Quail, 1992. Maize polyubiquitin genes: structure, thermal perturbation of expression and transcript splicing, and promoter activity following transfer to protoplasts by electroporation), or the rice actin 1 promoter (*Plant Mol. Biol.* 18, 675-689.; Zhang, McElroy and Wu, 1991, Analysis of rice Act1 5' region activity in transgenic rice plants, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant and Cell Physiology* 39: 885-889), a *Vicia faba* promoter from the legumin B4 and the unknown seed protein gene from *Vicia faba* (Conrad et al., 1998, *Journal of Plant Physiology* 152: 708-711), a promoter from a seed oil body protein (Chen et al., 1998, *Plant and Cell Physiology* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102: 991-1000, the *chlorella* virus adenine methyltransferase gene promoter (Mitra and Higgins, 1994, *Plant Molecular Biology* 26: 85-93), or the aldP gene promoter from rice (Kagaya et al., 1995, *Molecular and General Genetics* 248: 668-674), or a wound inducible promoter such as the potato pin2 promoter (Xu et al., 1993, *Plant Molecular Biology* 22: 573-588). Likewise, the promoter may be inducible by abiotic treatments such as temperature, drought or alterations in salinity or inducible by exogenously applied substances that activate the promoter, e.g., ethanol, oestrogens, plant hormones like ethylene, abscisic acid, gibberellic acid, and/or heavy metals.

A promoter enhancer element may also be used to achieve higher expression of the polypeptide in the plant. For instance, the promoter enhancer element may be an intron which is placed between the promoter and the nucleotide sequence encoding a polypeptide of the present invention. For instance, Xu et al., 1993, supra disclose the use of the first intron of the rice actin 1 gene to enhance expression.

Still further, the codon usage may be optimized for the plant species in question to improve expression (see Horvath et al. referred to above).

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Molecular Biology* 19: 15-38), and it can also be used for transforming monocots, although other transformation methods are more often used for these plants. Presently, the method of choice for generating transgenic monocots, supplementing the *Agrobacterium* approach, is particle bombardment (microscopic gold or tungsten particles coated with the transforming DNA) of embryonic calli or developing embryos (Christou, 1992, *Plant Journal* 2: 275-281; Shimamoto, 1994, *Current Opinion Biotechnology* 5: 158-162; Vasil et al., 1992, *Bio/Technology* 10: 667-674). An alternative method for transformation of monocots is based on protoplast transformation as described by Omirulleh et al., 1993, *Plant Molecular Biology* 21: 415-428.

Following transformation, the transformants having incorporated therein the expression construct are selected and regenerated into whole plants according to methods well-known in the art. Often the transformation procedure is designed for the selective elimination of selection genes either during regeneration or in the following generations by using, e.g., co-transformation with two separate T-DNA constructs or site specific excision of the selection gene by a specific recombinase.

The present invention also relates to methods for producing a polypeptide of the present invention comprising (a) cultivating a transgenic plant or a plant cell comprising a nucleic acid sequence encoding a polypeptide having phytase activity of the present invention under conditions conducive for production of the polypeptide; and (b) recovering the polypeptide.

Transgenic Animals

The present invention also relates to a transgenic, non-human animal and products or elements thereof, examples of which are body fluids such as milk and blood, organs, flesh, and animal cells. Techniques for expressing proteins, e.g., in mammalian cells, are known in the art, see, e.g., the handbook Protein Expression: A Practical Approach, Higgins and Hames (eds), Oxford University Press (1999), and the three other handbooks in this series relating to Gene Transcription, RNA processing, and Post-translational Processing. Generally speaking, to prepare a transgenic animal, selected cells of a selected animal are transformed with a nucleic acid sequence encoding a polypeptide having phytase activity of the present invention so as to express and produce the polypeptide. The polypeptide may be recovered from the animal, e.g., from the milk of female animals, or the polypeptide may be expressed to the benefit of the animal itself, e.g., to assist the animal's digestion. Examples of animals are mentioned below in the section headed Animal Feed.

To produce a transgenic animal with a view to recovering the polypeptide from the milk of the animal, a gene encoding the polypeptide may be inserted into the fertilized eggs of an animal in question, e.g., by use of a transgene expression vector which comprises a suitable milk protein promoter, and the gene encoding the polypeptide. The transgene expression vector is microinjected into fertilized eggs, and preferably permanently integrated into the chromosome. Once the egg begins to grow and divide, the potential embryo is implanted into a surrogate mother, and animals carrying the transgene are identified. The resulting animal can then be multiplied by conventional breeding. The polypeptide may be purified from the animal's milk, see, e.g., Meade et al., 1999, Expression of recombinant proteins in the milk of transgenic animals, Gene expression systems: Using nature for the art of expression, Fernandez and Hoeffler (eds.), Academic Press.

In the alternative, in order to produce a transgenic non-human animal that carries in the genome of its somatic and/or germ cells a nucleic acid sequence including a heterologous transgene construct including a transgene encoding the polypeptide, the transgene may be operably linked to a first regulatory sequence for salivary gland specific expression of the polypeptide, as disclosed in WO 00/064247.

Compositions and Uses

In still further aspects, the present invention relates to compositions comprising a polypeptide of the present invention, as well as methods of using these.

The polypeptide compositions may be prepared in accordance with methods known in the art and may be in the form of a liquid or a dry composition. For instance, the polypeptide composition may be in the form of granulates or microgranulates. The polypeptide to be included in the composition may be stabilized in accordance with methods known in the art.

The phytase of the invention can be used for degradation, in any industrial context, of, for example, phytate, phytic acid, and/or the mono-, di-, tri-, tetra- and/or penta-phosphates of myo-inositol. It is well known that the phosphate moieties of these compounds chelates divalent and trivalent cations such as metal ions, inter alia, the nutritionally essential ions of calcium, iron, zinc and magnesium as well as the trace minerals manganese, copper and molybdenum. Besides, the phytic acid also to a certain extent binds proteins by electro-static interaction.

Accordingly, preferred uses of the polypeptides of the invention are in animal feed preparations (including human food) or in additives for such preparations.

In a particular embodiment, the polypeptide of the invention can be used for improving the nutritional value of an animal feed. Non-limiting examples of improving the nutritional value of animal feed (including human food), are: Improving feed digestibility; promoting growth of the animal; improving feed utilization; improving bio-availability of proteins; increasing the level of digestible phosphate; improving the release and/or degradation of phytate; improving bio-availability of trace minerals; improving bio-availability of macro minerals; eliminating the need for adding supplemental phosphate, trace minerals, and/or macro minerals; and/or improving egg shell quality. The nutritional value of the feed is therefore increased, and the growth rate and/or weight gain and/or feed conversion (i.e., the weight of ingested feed relative to weight gain) of the animal may be improved.

Furthermore, the polypeptide of the invention can be used for reducing phytate level of manure.

Animals, Animal Feed, and Animal Feed Additives

The term animal includes all animals, including human beings. Examples of animals are non-ruminants, and ruminants. Ruminant animals include, for example, animals such as sheep, goat, and cattle, e.g., cow such as beef cattle and dairy cows. In a particular embodiment, the animal is a non-ruminant animal. Non-ruminant animals include mono-gastric animals, e.g., pig or swine (including, but not limited to, piglets, growing pigs, and sows); poultry such as turkeys, ducks and chickens (including but not limited to broiler chicks, layers); fish (including but not limited to salmon, trout, tilapia, catfish and carp); and crustaceans (including but not limited to shrimp and prawn).

The term feed or feed composition means any compound, preparation, mixture, or composition suitable for, or intended for intake by an animal.

In the use according to the invention the polypeptide can be fed to the animal before, after, or simultaneously with the diet. The latter is preferred.

In a particular embodiment, the polypeptide, in the form in which it is added to the feed, or when being included in a feed additive, is substantially pure. In a particular embodiment it is well-defined. The term "well-defined" means that the phytase preparation is at least 50% pure as determined by Size-exclusion chromatography (see Example 12 of WO 01/58275). In other particular embodiments the phytase preparation is at least 60, 70, 80, 85, 88, 90, 92, 94, or at least 95% pure as determined by this method.

A substantially pure, and/or well-defined polypeptide preparation is advantageous. For instance, it is much easier to dose correctly to the feed a polypeptide that is essentially free from interfering or contaminating other polypeptides. The term dose correctly refers in particular to the objective of obtaining consistent and constant results, and the capability of optimising dosage based upon the desired effect.

For the use in animal feed, however, the phytase polypeptide of the invention need not be that pure; it may, e.g., include other polypeptides, in which case it could be termed a phytase preparation.

The phytase preparation can be (a) added directly to the feed (or used directly in a treatment process of proteins), or (b) it can be used in the production of one or more intermediate compositions such as feed additives or premixes that is subsequently added to the feed (or used in a treatment process). The degree of purity described above refers to the purity of the original polypeptide preparation, whether used according to (a) or (b) above.

Polypeptide preparations with purities of this order of magnitude are in particular obtainable using recombinant methods of production, whereas they are not so easily obtained and also subject to a much higher batch-to-batch variation when the polypeptide is produced by traditional fermentation methods.

Such polypeptide preparation may of course be mixed with other polypeptides.

The polypeptide can be added to the feed in any form, be it as a relatively pure polypeptide, or in admixture with other components intended for addition to animal feed, i.e., in the form of animal feed additives, such as the so-called pre-mixes for animal feed.

In a further aspect the present invention relates to compositions for use in animal feed, such as animal feed, and animal feed additives, e.g., premixes.

Apart from the polypeptide of the invention, the animal feed additives of the invention contain at least one fat-soluble vitamin, and/or at least one water soluble vitamin, and/or at least one trace mineral. The feed additive may also contain at least one macro mineral.

Further, optional, feed-additive ingredients are colouring agents, e.g., carotenoids such as beta-carotene, astaxanthin, and lutein; aroma compounds; stabilizers; antimicrobial peptides; polyunsaturated fatty acids; reactive oxygen generating species; and/or at least one other polypeptide selected from amongst phytase (EC 3.1.3.8 or 3.1.3.26); phosphatase (EC 3.1.3.1; EC 3.1.3.2; EC 3.1.3.39); xylanase (EC 3.2.1.8); galactanase (EC 3.2.1.89); alpha-galactosidase (EC 3.2.1.22); protease (EC 3.4.-.-), phospholipase A1 (EC 3.1.1.32); phospholipase A2 (EC 3.1.1.4); lysophospholipase (EC 3.1.1.5); phospholipase C (3.1.4.3); phospholipase D (EC 3.1.4.4); amylase such as, for example, alpha-amylase (EC 3.2.1.1); and/or beta-glucanase (EC 3.2.1.4 or EC 3.2.1.6).

In a particular embodiment these other polypeptides are well-defined (as defined above for phytase preparations).

The phytase of the invention may also be combined with other phytases, for example ascomycete phytases such as *Aspergillus* phytases, for example derived from *Aspergillus awamori*, *Aspergillus ficuum*, or *Aspergillus niger*; or basidiomycete phytases, for example derived from *Agrocybe pediades*, *Paxillus involutus*, *Peniophora lycii*, or *Trametes pubescens*; or derivatives, fragments or variants thereof which have phytase activity.

Thus, in preferred embodiments of the use in animal feed of the invention, and in preferred embodiments of the animal feed additive and the animal feed of the invention, the phytase of the invention is combined with such phytases.

Examples of antimicrobial peptides (AMP's) are CAP18, Leucocin A, Tritrpticin, Protegrin-1, Thanatin, Defensin, Lactoferrin, Lactoferricin, and Ovispirin such as Novispirin (Robert Lehrer, 2000), Plectasins, and Statins, including the compounds and polypeptides disclosed in WO 03/044049 and WO 03/048148, as well as variants or fragments of the above that retain antimicrobial activity.

Examples of antifungal polypeptides (AFP's) are the *Aspergillus giganteus* and *Aspergillus niger* peptides, as well as variants and fragments thereof which retain antifungal activity, as disclosed in WO 94/01459 and WO 02/090384.

Examples of polyunsaturated fatty acids are C18, C20 and C22 polyunsaturated fatty acids, such as arachidonic acid, docosohexaenoic acid, eicosapentaenoic acid and gamma-linoleic acid.

Examples of reactive oxygen generating species are chemicals such as perborate, persulphate, or percarbonate; and polypeptides such as an oxidase, an oxygenase or a synthethase.

Usually fat- and water-soluble vitamins, as well as trace minerals form part of a so-called premix intended for addition to the feed, whereas macro minerals are usually separately added to the feed. Either of these composition types, when enriched with a polypeptide of the invention, is an animal feed additive of the invention.

In a particular embodiment, the animal feed additive of the invention is intended for being included (or prescribed as having to be included) in animal diets or feed at levels of 0.01 to 10.0%; more particularly 0.05 to 5.0%; or 0.2 to 1.0% (% meaning g additive per 100 g feed). This is so in particular for premixes.

The following are non-exclusive lists of examples of these components:

Examples of fat-soluble vitamins are vitamin A, vitamin D3, vitamin E, and vitamin K, e.g., vitamin K3.

Examples of water-soluble vitamins are vitamin B12, biotin and choline, vitamin B1, vitamin B2, vitamin B6, niacin, folic acid and panthothenate, e.g., Ca-D-panthothenate.

Examples of trace minerals are manganese, zinc, iron, copper, iodine, selenium, and cobalt.

Examples of macro minerals are calcium, phosphorus and sodium.

The nutritional requirements of these components (exemplified with poultry and piglets/pigs) are listed in Table A of WO 01/58275. Nutritional requirement means that these components should be provided in the diet in the concentrations indicated.

In the alternative, the animal feed additive of the invention comprises at least one of the individual components specified in Table A of WO 01/58275. At least one means either of, one or more of, one, or two, or three, or four and so forth up to all thirteen, or up to all fifteen individual components. More specifically, this at least one individual component is included in the additive of the invention in such an amount as to provide an in-feed-concentration within the range indicated in column four, or column five, or column six of Table A.

The present invention also relates to animal feed compositions. Animal feed compositions or diets have a relatively high content of protein. Poultry and pig diets can be characterised as indicated in Table B of WO 01/58275, columns 2-3. Fish diets can be characterised as indicated in column 4 of this Table B. Furthermore such fish diets usually have a crude fat content of 200-310 g/kg.

WO 01/58275 corresponds to U.S. Ser. No. 09/779,334 which is hereby incorporated by reference.

An animal feed composition according to the invention has a crude protein content of 50-800 g/kg, and furthermore comprises at least one polypeptide as claimed herein.

Furthermore, or in the alternative (to the crude protein content indicated above), the animal feed composition of the invention has a content of metabolisable energy of 10-30 MJ/kg; and/or a content of calcium of 0.1-200 g/kg; and/or a content of available phosphorus of 0.1-200 g/kg; and/or a content of methionine of 0.1-100 g/kg; and/or a content of methionine plus cysteine of 0.1-150 g/kg; and/or a content of lysine of 0.5-50 g/kg.

In particular embodiments, the content of metabolizable energy, crude protein, calcium, phosphorus, methionine, methionine plus cysteine, and/or lysine is within any one of ranges 2, 3, 4 or 5 in Table B of WO 01/58275 (R. 2-5).

Crude protein is calculated as nitrogen (N) multiplied by a factor 6.25, i.e., Crude protein (g/kg)=N (g/kg)×6.25. The nitrogen content is determined by the Kjeldahl method (A.O.A.C., 1984, Official Methods of Analysis 14th ed., Association of Official Analytical Chemists, Washington D.C.).

Metabolizable energy can be calculated on the basis of the NRC publication Nutrient requirements in swine, ninth revised edition 1988, subcommittee on swine nutrition, committee on animal nutrition, board of agriculture, national research council. National Academy Press, Washington, D.C., pp. 2-6, and the European Table of Energy Values for Poultry Feed-stuffs, Spelderholt centre for poultry research and extension, 7361 DA Beekbergen, The Netherlands. Grafisch bedrijf Ponsen & looijen by, Wageningen. ISBN 90-71463-12-5.

The dietary content of calcium, available phosphorus and amino acids in complete animal diets is calculated on the basis of feed tables such as Veevoedertabel 1997, gegevens over chemische samenstelling, verteerbaarheid en voederwaarde van voedermiddelen, Central Veevoederbureau, Runderweg 6, 8219 pk Lelystad. ISBN 90-72839-13-7.

In a particular embodiment, the animal feed composition of the invention contains at least one protein. The protein may be an animal protein, such as meat and bone meal, and/or fish meal; or it may be a vegetable protein. The term vegetable proteins as used herein refers to any compound, composition, preparation or mixture that includes at least one protein derived from or originating from a vegetable, including modified proteins and protein-derivatives. In particular embodiments, the protein content of the vegetable proteins is at least 10, 20, 30, 40, 50, or 60% (w/w).

Vegetable proteins may be derived from vegetable protein sources, such as legumes and cereals, for example materials from plants of the families Fabaceae (Leguminosae), Cruciferaceae, Chenopodiaceae, and Poaceae, such as soy bean meal, lupin meal and rapeseed meal.

In a particular embodiment, the vegetable protein source is material from one or more plants of the family Fabaceae, e.g., soybean, lupine, pea, or bean.

In another particular embodiment, the vegetable protein source is material from one or more plants of the family Chenopodiaceae, e.g., beet, sugar beet, spinach or quinoa.

Other examples of vegetable protein sources are rapeseed, sunflower seed, cotton seed, and cabbage.

Soybean is a preferred vegetable protein source.

Other examples of vegetable protein sources are cereals such as barley, wheat, rye, oat, maize (corn), rice, triticale, and sorghum.

In still further particular embodiments, the animal feed composition of the invention contains 0-80% maize; and/or 0-80% sorghum; and/or 0-70% wheat; and/or 0-70% Barley; and/or 0-30% oats; and/or 0-40% soybean meal; and/or 0-25% fish meal; and/or 0-25% meat and bone meal; and/or 0-20% whey.

Animal diets can, e.g., be manufactured as mash feed (non pelleted) or pelleted feed. Typically, the milled feed-stuffs are mixed and sufficient amounts of essential vitamins and minerals are added according to the specifications for the species in question. Polypeptides can be added as solid or liquid polypeptide formulations. For example, a solid polypeptide formulation is typically added before or during the mixing step; and a liquid polypeptide preparation is typically added after the pelleting step. The polypeptide may also be incorporated in a feed additive or premix.

The final polypeptide concentration in the diet is within the range of 0.01-200 mg polypeptide protein per kg diet, for example in the range of 5-30 mg polypeptide protein per kg animal diet.

The phytase of the invention should of course be applied in an effective amount, i.e., in an amount adequate for improving solubilisation and/or improving nutritional value of feed. It is at present contemplated that the polypeptide is administered in one or more of the following amounts (dosage ranges): 0.01-200; 0.01-100; 0.5-100; 1-50; 5-100; 10-100; 0.05-50; or 0.10-10—all these ranges being in mg phytase polypeptide protein per kg feed (ppm).

For determining mg phytase polypeptide protein per kg feed, the phytase is purified from the feed composition, and the specific activity of the purified phytase is determined using a relevant assay. The phytase activity of the feed composition as such is also determined using the same assay, and on the basis of these two determinations, the dosage in mg phytase protein per kg feed is calculated.

The same principles apply for determining mg phytase polypeptide protein in feed additives. Of course, if a sample is available of the phytase used for preparing the feed additive or the feed, the specific activity is determined from this sample (no need to purify the phytase from the feed composition or the additive).

Methods for Producing Fermentation Products and Co-Products

Yet another aspect of the present invention relates to the methods for producing a fermentation product/co-product, such as, e.g., ethanol, beer, wine, distillers dried grains (DDG), wherein the fermentation is carried out in the presence of a phytase of the present invention. Examples of fermentation processes include, for example, the processes described in WO 01/62947. Fermentation is carried out using a fermenting microorganism, such as, yeast.

In a particular embodiment, the present invention provides methods for producing ethanol, comprising fermenting (using a fermenting microorganism, such as yeast) a carbohydrate containing material (e.g., starch) in the presence of a phytase of the present invention.

In another embodiment, the present invention provides methods for producing ethanol comprising hydrolyzing starch, e.g., by a liquefaction and/or saccharification process, a raw starch hydrolysis process, fermenting the resulting starch in the presence of a phytase of the present invention, and producing ethanol.

The phytase may be added to the fermentation process at any suitable stage and in any suitable composition, including alone or in combination with other enzymes, such as, one or more alpha-amylases, cellulases, glucoamylases, and proteases.

In another embodiment, the present invention provides methods for producing ethanol comprising hydrolyzing biomass, and fermenting the resulting biomass in the presence of a phytase of the present invention.

EXAMPLES

Chemicals used as buffers and substrates were commercial products of at least reagent grade.

Example 1

Cloning and Expression of *Buttiauxella* Phytases

A multiple alignment was made of the following histidine acid phosphatases (HAP): appA *Escherichia coli* (SP-TREMBL:Q8GN88), *Citrobacter gillenii* DSM 13694 phytase (geneseqp:aeh04533), *Citrobacter amalonaticus* ATCC 25407 phytase (geneseqp:aeh04535), *Citrobacter braakii* phytase (geneseqp:aeh04827), and ypo1648 *Yersinia pestis* CO92 (SPTREMBL:Q8ZFP6). Two degenerate oligonucleotide primers were designed on the basis of consensus sequences:

```
2123:
                         (SEQ ID NO: 9, forward primer)
5'-CATGGTGTGCGNGCNCCNACNAA-3'

2065:
                         (SEQ ID NO: 10, reverse primer)
5'-CCCACCAGGNGGNGTRTTRTCNGGYTG-3',
``` wherein Y designates T or C, R designates A or G, and N designates A, C, G or T.

The primers were used for PCR screening of a number of bacterial species at annealing temperatures between 40 and 50° C. but typically as touch down program starting with 50° C. and then reducing the annealing temperature with 1° C. for each cycle over the next 10 cycles before conducting standard PCR.

A partial phytase gene in the form of an approximately 950 bp PCR fragment was identified in *Buttiauxella agrestis* DSM 18932.

The PCR fragment was isolated from agarose gel and the fragment was sequenced using the same PCR primers as those with which the fragment was generated. By translation of the nucleotide sequence, it was confirmed that the DNA fragment was part of a HAP phytase gene.

For obtaining the full length nucleotide sequence of the gene, the DNA Walking SpeedUp Kit (DWSK-V102 from Seegene, Inc., 2nd Fl., Myungji Bldg., 142-21, Samsung-dong, Kangnam-gu, Seoul, 135-090, Korea) was used, which is designed to capture unknown target sites. For this purpose, 4 specific oligonucleotides were designed and used with the kit:

```
2138 TSP1N:
                         (SEQ ID NO: 11)
5'-ATTGCGGAGCAAGCCCTG-3'

2139 TSP2N:
                         (SEQ ID NO: 12)
5'-TCGCCAGTTTTAAGCGNGCG-3'

2136 TSP1C:
                         (SEQ ID NO: 13)
5'-TGGAATATGCGCAAGGGATG-3'

2137 TSP2C:
                         (SEQ ID NO: 14)
5'-TGGGGGTCAGAGCAAGAGTGGG-3'
```

The full length nucleotide sequence encoding the phytase from *Buttiauxella agrestis* DSM 18932 is shown in the sequence listing as SEQ ID NO: 5, and the corresponding encoded amino acid sequence has SEQ ID NO: 6. The first 33 amino acids of SEQ ID NO: 6 (i.e., amino acids −33 to −1) are a signal peptide, as predicted by Signal P V3.0 (see www.cbs.dtu.dk/services/SignalP/).

The same multiple alignment described above was used for design of two other degenerate oligonucleotide PCR primers:

```
315:
                         (SEQ ID NO: 15, forward primer)
5'-CGCGTGGTGATTGTGTCCMGNCAYGGNGT-3'

316:
                         (SEQ ID NO: 16, reverse primer)
5'-CCAGGTTGGTATCATGGCCNGCDATRAA-3',
``` wherein Y designates T or C, M designates A or C, N designates A, C, G or T, and R designates A or G.

The primers were used for PCR screening of a number of bacterial species at the same conditions as described above.

Partial phytase genes in the form of approximately 900 bp PCR fragments were identified in *Buttiauxella gaviniae* DSM 18930 as well as in *Buttiauxella agrestis* DSM 18931.

The two PCR fragments were isolated from agarose gel and sequenced using primers 1978 and 1979:

```
1978:
                         (SEQ ID NO: 17)
5'-CGCGTGGTGATTGTGTCC-3'

1979:
                         (SEQ ID NO: 18)
5'-CCAGGTTGGTATCATGGCC-3'
```

By translation of the nucleotide sequence, it was confirmed that both DNA fragments were PCR amplified from HAP phytase genes.

Four new primers were designed for each gene for obtaining the full length nucleotide sequence of the gene according to the instructions given in the DNA Walking SpeedUp Kit (DWSK-V102 from Seegene, Inc., 2nd Fl., Myungji Bldg., 142-21, Samsung-dong, Kangnam-gu, Seoul, 135-090, Korea).

The four specific oligonucleotide PCR primers designed for the *Buttiauxella gaviniae* DSM 18930 phytase gene were:

```
2029 TSP1N:
                         (SEQ ID NO: 19)
5'-AAGCTTCGCCAGTTTTAAGCG-3'

2030 TSP2N:
                         (SEQ ID NO: 20)
5'-TTGAGTTTGGTGTGGGGCAACTG-3'

2031 TSP1C:
                         (SEQ ID NO: 21)
5'-TGGCAACAAAGTCGCTCTCG-3'

2032 TSP2C:
                         (SEQ ID NO: 22)
5'-TCCTGCTGGAATATGCGCAAGG-3'
```

The four specific oligonucleotide PCR primers designed for the *Buttiauxella agrestis* DSM 18931 phytase gene were:

2017 TSP1N:
5'-TTCGCCCGTTTTAAGCGTG-3' (SEQ ID NO: 23)

2018 TSP1C:
5'-ACTGCCCTGCGATAAAATGCCC-3' (SEQ ID NO: 24)

2019 TSP2N:
5'-TTTCCTGCTGGAATATGCGC-3' (SEQ ID NO: 25)

2020 TSP2C:
5'-TTGATGGCGCGCACACCTTAC-3' (SEQ ID NO: 26)

The full length nucleotide sequence encoding the phytase from *Buttiauxella gaviniae* DSM 18930 is shown in the sequence listing as SEQ ID NO: 1, and the corresponding encoded amino acid sequence has SEQ ID NO: 2. The first 33 amino acids of SEQ ID NO: 2 (i.e., amino acids −33 to −1) are expected to be a signal peptide (predicted by Signal P V3.0, see www.cbs.dtu.dk/services/SignalPI).

The full length nucleotide sequence encoding the mature phytase, as well as a partial sequence coding for the signal peptide from *Buttiauxella agrestis* DSM 18931 is shown in the sequence listing as SEQ ID NO: 3. The corresponding encoded amino acid sequence has SEQ ID NO: 4. The first 9 amino acids of SEQ ID NO: 4 (i.e., amino acids −9 to −1) are expected to be a part of the signal peptide.

The three phytase genes were expressed in *Bacillus subtilis* as follows:

The signal peptide encoding sequence of SEQ ID NO: 7 (encoding the signal peptide of SEQ ID NO: 8 and derived from a *Bacillus licheniformis* protease) was fused by PCR in frame to the gene encoding the mature phytase from each of the three phytases in turn.

The DNA coding for the resulting coding sequence was integrated by homologous recombination on the *Bacillus subtilis* host cell genome. The gene constructs were expressed under the control of a triple promoter system (as described in WO 99/43835), consisting of the promoters from *Bacillus amyloliquefaciens* alpha-amylase gene (amyQ), *Bacillus licheniformis* alpha-amylase gene (amyL), and the *Bacillus thuringiensis* cryIIIA promoter including stabilizing sequence. The gene coding for Chloramphenicol acetyltransferase was used as marker as described in, e.g., Diderichsen et al., 1993, A useful cloning vector for *Bacillus subtilis*, *Plasmid* 30: 312.

For each of the three constructs, chloramphenicol resistant transformants were cultured in PS-1 medium (10% sucrose, 4% soybean flour, 1% $Na_3PO_4$-$12H_2O$, 0.5% $CaCO_3$, and 0.01% pluronic acid), while shaking at 250 rpm at 30° C. After 2-5 days of incubation the supernatants were removed and the phytase activity was identified by applying 20 microliters of the supernatant into 4 mm diameter holes punched out in 1% LSB-agarose plates containing 0.1 M Sodium acetate pH 4.5 and 0.1% Inositol hexaphosphoric acid. The plates were left over night at 37° C. and a buffer consisting of 0.25 M $CaCl_2$ and 500 mM MES (adjusted to pH 6.5 with 4 N NaOH) were poured over the plates. The plates were left at room temperature for 1 h and the inositolphosphate phosphatase, or phytase, activity was then identified as a clear zone.

Several phytase positive transformants for each of the three constructs were analyzed by DNA sequencing to ensure the correct DNA sequence of the constructs. One correct clone was selected for each of the three constructs.

Example 2

Fermentation and Purification of *Buttiauxella* Phytases

The strain of *Bacillus subtilis* harboring the *Buttiauxella agrestis* DSM 18932 phytase construct and capable of expressing the phytase having SEQ ID NO: 6 (mature part) was cultivated at 30° C. and with 250 rpm for 6 days in SK-1 M medium (Sodium Caseinate (Miprodan 30 from Arla) 40 g, Maltodextrin 01 (Glucidex 6, catalogue no. 332203 from Roquette), 200 g, Soybean Meal 50 g, Dowfax 63N10 (a non-ionic surfactant from Dow) 0.1 ml, tap water up to 1000 ml, $CaCO_3$ tablet 0.5 g/100 ml).

The strain of *Bacillus subtilis* harboring the *Buttiauxella agrestis* DSM 18931 phytase construct and capable of expressing the phytase having SEQ ID NO: 4 (mature part) was cultivated at 30° C. and with 250 rpm for 5 days in the PS-1 medium which is described in Example 1.

The strain of *Bacillus subtilis* harboring the *Buttiauxella gaviniae* DSM 18930 phytase construct and capable of expressing the phytase having SEQ ID NO: 2 (mature part) was cultivated at 30° C. and with 250 rpm for 5 days in the PS-1 medium which is described in Example 1.

The fermentation supernatant with the phytase of SEQ ID NO: 2 was first centrifuged at 7200 rpm and 5° C. for 2 hours and filtered through a Fast PES Bottle top filter with a 0.22 micro-m cut-off. Next, the filtered supernatant was pretreated as follows:

The sample solution was washed with water and concentrated using an ultrafiltration unit (Filtron, from Filtron Technology Corporation) equipped with a 10 kDa cut-off ultrafiltration membrane.

Then pH was adjusted to 5.0 with 6 M HCl, which caused a minor precipitation. This was removed by centrifugation of the sample at 7200 rpm for 20 minutes at 5° C. The supernatant, containing the phytase, was added 2.5 ml 1 M sodium acetate pH 5.0 and filtered through a Fast PES bottle top filter with a 0.22 micro-m cut-off. After this the pH of the solution was measured to 5.0 and the conductivity was found to be 1.8 mS/cm. After pretreatment the phytase was purified by chromatography on SP Sepharose, approximately 85 ml in a XK26 column, using as buffer A 20 mM sodium acetate pH 5.0, and as buffer B 20 mM sodium acetate+1 M NaCl pH 5.0.

The fractions from the column were analyzed for phytase activity and fractions with activity were pooled.

The phytase of SEQ ID NO: 4 was purified essentially as described above, except that 10% acetic acid was used to adjust the pH. Again some precipitation was observed and this was removed by centrifugation. The pH of the solution was measured to 5.0, while the conductivity was found to be approximately 1.2 mS/cm before the column chromatography step.

The fermentation supernatant with the phytase of SEQ ID NO: 6 was first centrifuged at 7200 rpm and 5° C. for one hour and filtered through a sandwich of four Whatman glass microfibre filters (2.7, 1.6, 1.2 and 0.7 micrometer). Following this the solution was filtered through a Seitz-EKS depth filter using pressure. The solution was added solid ammonium sulfate giving a final concentration of 1.5 M and the pH was adjusted to 6.0 using 6 M HCl.

The phytase-containing solution was applied to a butyl-sepharose column, approximately 50 ml in a XK26 column, using as buffer A 25 mM bis-tris+1.5 M ammonium sulfate pH 6.0, and as buffer B 25 mM bis-tris pH 6.0. However, the enzyme did not bind to the column and almost all activity was found in the flow-through and wash fractions. The flow-through and wash fractions were combined and solid ammonium sulfate was added to about 80% saturation. The solution was left overnight at 5° C. in order to complete precipitation. The precipitate was isolated (no activity was found in the supernatant) and dissolved in Milli-Q water. This solution was dialyzed against Milli-Q water and pH was adjusted to 4.5.

Following this the phytase was purified by chromatography on S Sepharose, approximately 150 ml in a XK26 column, using as buffer A 50 mM sodium acetate pH 4.5, and as buffer B 50 mM sodium acetate+1 M NaCl pH 4.5.

The fractions from the column were analyzed for phytase activity and fractions with activity were pooled. Finally, the fractions with phytase activity were concentrated using an Amicon ultra-15 filtering device with a 30 kDa cut-off membrane.

The molecular weight, as estimated from SDS-PAGE, was approximately 40 kDa for all three phytases and the purity was in all cases >95%.

Example 3

Phytase Activity Assay

Phytase activity may suitably be determined by the following assay:

75 microliters phytase-containing enzyme solution, appropriately diluted in 0.25 M sodium acetate, 0.005% (w/v) Tween-20, pH 5.5, is dispensed in a microtiter plate well, e.g., NUNC 269620, and 75 microliters substrate is added (prepared by dissolving 100 mg sodium phytate from rice (Aldrich Cat. No. 274321) in 10 ml 0.25 M sodium acetate buffer, pH 5.5). The plate is sealed and incubated 15 min. shaken with 750 rpm at 37° C. After incubation, 75 microliters stop reagent is added (the stop reagent being prepared by mixing 10 ml molybdate solution (10% (w/v) ammonium heptamolybdate in 0.25% (w/v) ammonia solution), 10 ml ammonium vanadate (0.24% commercial product from Bie&Berntsen, Cat. No. LAB17650), and 20 ml 21.7% (w/v) nitric acid), and the absorbance at 405 nm is measured in a microtiter plate spectrophotometer. The phytase activity is expressed in the unit of FYT, one FYT being the amount of enzyme that liberates 1 micromole inorganic ortho-phosphate per minute under the conditions above. An absolute value for the measured phytase activity may be obtained by reference to a standard curve prepared from appropriate dilutions of inorganic phosphate, or by reference to a standard curve made from dilutions of a phytase enzyme preparation with known activity (such standard enzyme preparation with a known activity is available on request from Novozymes NS, Krogshoejvej 36, DK-2880 Bagsvaerd).

Example 4

Specific Activity

The specific activity of the phytases from *Buttiauxella gaviniae* DSM 18930, *Buttiauxella agrestis* DSM 18931, and *Buttiauxella agrestis* DSM 18932 (having the amino acid sequences of the mature parts of SEQ ID NO: 2, 4 and 6, respectively) was determined in sodium acetate buffer, pH 5.5. The phytases were highly purified as described in Example 2, i.e., only one component was identified on an SDS polyacrylamide gel.

The protein concentration was determined by amino acid analysis as follows: An aliquot of the sample was hydrolyzed in 6 M HCl, 0.1% phenol for 16 h at 110° C. in an evacuated glass tube. The resulting amino acids were quantified using an Applied Biosystems 420A amino acid analysis system operated according to the manufacturer's instructions. From the amounts of the amino acids the total mass—and thus also the concentration—of protein in the hydrolyzed aliquot was calculated.

The phytase activity was determined in the units of FYT as described in Example 3, and the specific activity was calculated as the phytase activity measured in FYT units per mg phytase enzyme protein.

The resulting specific activities for the three phytases are shown in Table 2. The specific activity was determined on sodium phytate at pH 5.5 and 37° C.

TABLE 2

| Phytase | Specific activity (FYT/mg protein) |
|---|---|
| SEQ ID NO: 2 | 700 |
| SEQ ID NO: 4 | 800 |
| SEQ ID NO: 6 | 650 |

The wild-type (wt) phytase from *Buttiauxella* P1-29 described in WO 2006/043178 has a specific activity at pH 3.5 and 37° C. of about 300 U/mg (see Example 10 of this WO publication). According to Example 2 thereof, the ratio of activities at pH 3.5 and pH 5.5 is about 1.3, while according to FIG. 2 (pH activity profile of the purified phytase) this ratio is rather 1.5. In any event, when the specific activity at pH 3.5 is about 300 U/mg, the specific activity at pH 5.5 is not higher than 300/1.3=231 U/mg (maybe it is rather 300/1.5=200 U/mg).

WO 2006/043178 also discloses a variant phytase with a specific activity at pH 4.0 and 37° C. which is 115% of the specific activity of the wt. Using again FIG. 2, the specific activity of the wt at pH 4.0 is not higher than 80/60×300 U/mg=400 U/mg. The specific activity at pH 4.0 of the variant is then 1.15×400 U/mg=460 U/mg, while at pH 5.5 the specific activity of this variant is approximately 40/80×460 U/mg=230 U/mg (in fact, 230 is precisely 115% of the 200 U/mg of the wild-type at pH 5.5, as calculated above).

Apart from the pH-difference, which has been taken into account above, the assay conditions of WO 2006/043178 are, for all practical purposes, identical to those of the present invention, except possibly for the presence in WO 2006/043178 of 0.8 mM $CaCl_2$ in the reaction mixture. However, we have tested the activity of the phytases of SEQ ID NOs: 2, 4 and 6 in the assay of Example 3 including even more $Ca^{2+}$ (viz., 1 mM $CaCl_2$) but found no difference.

Accordingly, the phytases of the present invention have a very much improved specific activity at pH 5.5 as compared to the phytases disclosed in WO 2006/043178. In fact, the specific activity of the phytases of the invention is improved in the whole range of pH 3.5-5.5. This is apparent from Example 6 below, which shows that for the phytases of the invention the activity in this range is at least as high as the activity at pH 5.5.

Example 5 pI

The isoelectric point, pI, for the three phytases was determined using isoelectric focusing gels (Novex pH 3 10 IEF gel from Invitrogen, catalog number EC6655A2) run as described by the manufacturer. The pI for the *Buttiauxella agrestis* DSM 18931 and DSM 18932 phytases (SEQ ID NOs: 4 and 6) is 7.4, while the pI for the *Buttiauxella gaviniae* DSM 18930 (SEQ ID NO: 2) phytase is 7.6.

Example 6 pH Profile

The pH profile (phytase activity as a function of pH) of the three phytases was determined in the pH range of 2.0 to 7.5 as described in Example 3, except that a buffer cocktail (50 mM glycine, 50 mM acetic acid and 50 mM Bis-Tris(Bis-(2-hydroxyethyl)imino-tris(hydroxymethyl)methan)) was used instead of the 0.25 M sodium acetate pH 5.5 buffer.

The results are shown in Table 3 below, relative to the value at the optimum pH for each phytase (pH 4.5).

TABLE 3

Relative phytase activity versus pH

| pH | *Buttiauxella gaviniae* DSM 18930 (SEQ ID NO: 2) | *Buttiauxella agrestis* DSM 18931 (SEQ ID NO: 4) | *Buttiauxella noackiea* DSM 18932 (SEQ ID NO: 6) |
|---|---|---|---|
| 2.0 | 37 | 41 | 40 |
| 2.5 | 46 | 49 | 49 |
| 3.0 | 66 | 65 | 66 |
| 3.5 | 83 | 86 | 78 |
| 4.0 | 96 | 99 | 99 |
| 4.5 | 100 | 100 | 100 |
| 5.0 | 92 | 91 | 83 |
| 5.5 | 70 | 70 | 69 |
| 6.0 | 38 | 43 | 39 |
| 6.5 | 11 | 14 | 14 |
| 7.0 | −3 | 1 | 1 |
| 7.5 | −5 | −2 | 0 |

As compared to the pH activity profile of the wild-type (wt) phytase from *Buttiauxella* P1-29 described in WO 2006/043178 (see FIG. 2 thereof), the phytases of the invention appear to have a higher relative activity at low as well as high pH-values (at pH 2.0 and pH 6.0 the activity of the phytases of the present invention is twice as high, and eight times as high, respectively, as compared to the *Buttiauxella* P1-29 wt phytase).

Example 7 pH Stability

The pH stability of the purified phytases of SEQ ID NOs: 2 and 4 at 40° C. was determined by measuring residual phytase activity after incubation at 40° C. and at various pH values for 1.5 and 24 hours. The phytases were incubated in 0.1 M glycine, 0.1 M acetic acid, 0.1 M Bis-Tris, adjusted to the desired pH. Samples of the respective incubation mixtures were withdrawn after 0, 1.5 and 24 hours, the pH of the samples was adjusted to 5.5 by dilution in 0.25 M sodium acetate, 0.005% (w/v) Tween20, pH 5.5), and the residual activity at pH 5.5 was determined using the method described in Example 3. The results, normalized to the activity found at 0 hours, are shown in Table 4 below.

TABLE 4 pH stability at 40° C.

| pH | *Buttiauxella gaviniae* (SEQ ID NO: 2) | *Buttiauxella agrestis* (SEQ ID NO: 4) |
|---|---|---|
| | 1.5 hours | |
| 2.0 | 77 | 83 |
| 3.0 | 74 | 85 |
| 4.0 | 81 | 95 |
| 5.0 | 80 | 68 |
| 6.0 | 82 | 67 |
| 7.0 | 79 | 75 |
| 8.0 | 80 | 74 |
| | 24 hours | |
| 2.0 | 51 | 56 |
| 3.0 | 66 | 66 |
| 4.0 | 77 | 88 |
| 5.0 | 78 | 67 |
| 6.0 | 76 | 67 |
| 7.0 | 76 | 73 |
| 8.0 | 77 | 70 |

Both phytases are very stable for 1.5 hours in the entire range of pH 2.0-8.0, whereas when incubated for 24 hours a certain loss of activity is observed at the lower pH values (pH 2.0-3.0).

Example 8

Temperature Profile

The temperature profile (phytase activity as a function of temperature) of the three phytases was determined in the temperature range of 20-90° C. essentially as described in Example 3, however, the enzymatic reactions (100 microliters phytase-containing enzyme solution+100 microliters substrate) were performed in PCR tubes instead of microtiter plates. After a 15 minute reaction period at desired temperature the tubes were cooled to 20° C. for 20 seconds and 150 microliters of the reaction mixture was transferred to a microtiter plate. 75 microliters stop reagent was added and the absorbance at 405 nm was measured in a microtiter plate spectrophotometer.

The temperature profiles for the phytases of SEQ ID NOs: 2 and 4 were determined at pH 4.0 (0.25 M sodium acetate), whereas the temperature profile for the phytase of SEQ ID NO: 6 was determined at pH 5.5 (0.25 M sodium acetate).

The results are shown in Table 5 below, for each phytase relative to the activity at the optimum temperature.

TABLE 5

Temperature profile at pH 4.0/5.5

| | Temperature (° C.) | | | | | | | |
|---|---|---|---|---|---|---|---|---|
| | 20 | 30 | 40 | 50 | 60 | 70 | 80 | 90 |
| SEQ ID NO: 2 | 21 | 36 | 43 | 75 | 100 | 23 | 9 | 6 |
| SEQ ID NO: 4 | 24 | 40 | 54 | 82 | 100 | 17 | 8 | 7 |
| SEQ ID NO: 6 | 22 | 32 | 50 | 74 | 100 | 14 | 8 | 3 |

All phytases appear to have an optimum temperature of about 60° C., are fairly active in the temperature range of 30-60° C., and also show a decent activity at 20° C. as well as at 70° C. In the range of 80-90° C. the activity is insignificant.

Deposit of Biological Material

The following biological material has been deposited under the terms of the Budapest Treaty with DSMZ (Deutsche Sammlung von Mikroorganismen and Zellkulturen GmbH), Inhoffenstraβe 7 B, D-38124 Braunschweig, Germany, and given the following accession numbers:

| Deposit | Accession Number | Date of Deposit |
|---|---|---|
| *Buttiauxella gaviniae* | DSM 18930 | 15 Jan. 2007 |
| *Buttiauxella agrestis* | DSM 18931 | 15 Jan. 2007 |
| *Buttiauxella agrestis* | DSM 18932 | 15 Jan. 2007 |

The strains have been deposited under conditions that assure that access to the culture will be available during the pendency of this patent application to one determined by the Commissioner of Patents and Trademarks to be entitled thereto under 37 C.F.R. §1.14 and 35 U.S.C. §122. The deposits represent substantially pure cultures of the deposited strains. The deposits are available as required by foreign patent laws in countries wherein counterparts of the subject application or its progeny are filed. However, it should be understood that the availability of a deposit does not constitute a license to practice the subject invention in derogation of patent rights granted by governmental action.

The above strains were isolated from samples collected in Denmark in 2005.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

The invention claimed is:

1. A recombinant host cell comprising a recombinant polynucleotide comprising a nucleotide sequence which encodes a recombinant polypeptide having phytase activity and having an amino acid sequence which
   a) has at least 80% identity to amino acids 1-413 of SEQ ID NO: 2, amino acids 1-413 of SEQ ID NO: 4, and/or amino acids 1-413 of SEQ ID NO: 6; and
   b) comprises at least one of the following amino acids at the position indicated: 119N, 120L, and/or 121E, when aligned to amino acids 1-413 of SEQ ID NO: 2 and using an amino acid residue numbering corresponding to amino acids 1-413 of SEQ ID NO: 2.

2. The recombinant host cell of claim 1, wherein the polypeptide has at least 85% identity to amino acids 1-413 of SEQ ID NO: 2, amino acids 1-413 of SEQ ID NO: 4, and/or amino acids 1-413 of SEQ ID NO: 6.

3. The recombinant host cell of claim 1, wherein the polypeptide has at least 90% identity to amino acids 1-413 of SEQ ID NO: 2, amino acids 1-413 of SEQ ID NO: 4, and/or amino acids 1-413 of SEQ ID NO: 6.

4. The recombinant host cell of claim 1, wherein the polypeptide has at least 95% identity to amino acids 1-413 of SEQ ID NO: 2, amino acids 1-413 of SEQ ID NO: 4, and/or amino acids 1-413 of SEQ ID NO: 6.

5. The recombinant host cell of claim 1, wherein the polypeptide comprises 119N.

6. The recombinant host cell of claim 1, wherein the polypeptide comprises 120L.

7. The recombinant host cell of claim 5, wherein the polypeptide comprises 120L.

8. The recombinant host cell of claim 1, wherein the polypeptide comprises 121E.

9. The recombinant host cell of claim 5, wherein the polypeptide comprises 121E.

10. The recombinant host cell of claim 6, wherein the polypeptide comprises 121E.

11. The recombinant host cell of claim 7, wherein the polypeptide comprises 121E.

12. The recombinant host cell of claim 4, wherein the polypeptide comprises 119N.

13. The recombinant host cell of claim 4, wherein the polypeptide comprises 120L.

14. The recombinant host cell of claim 12, wherein the polypeptide comprises 120L.

15. The recombinant host cell of claim 4, wherein the polypeptide comprises 121E.

16. The recombinant host cell of claim 12, wherein the polypeptide comprises 121E.

17. The recombinant host cell of claim 13, wherein the polypeptide comprises 121E.

18. The recombinant host cell of claim 14, wherein the polypeptide comprises 121E.

19. The recombinant host cell of claim 18, wherein the polypeptide comprises 109Q and 111G.

20. The recombinant host cell of claim 1, wherein the polypeptide consists of an amino acid sequence of 413 amino acids.

21. The recombinant host cell of claim 4, wherein the polypeptide consists of an amino acid sequence of 413 amino acids.

22. The recombinant host cell of claim 18, wherein the polypeptide consists of an amino acid sequence of 413 amino acids.

23. The recombinant host cell of claim 19, wherein the polypeptide consists of an amino acid sequence of 413 amino acids.

24. A method for producing a recombinant polypeptide having phytase activity comprising
    (a) cultivating a host cell of claim 1 under conditions conducive for production of the polypeptide; and
    (b) recovering the polypeptide.

25. A method for producing a recombinant polypeptide having phytase activity comprising
    (a) cultivating a host cell of claim 2 under conditions conducive for production of the polypeptide; and
    (b) recovering the polypeptide.

26. A method for producing a recombinant polypeptide having phytase activity comprising
    (a) cultivating a host cell of claim 3 under conditions conducive for production of the polypeptide; and
    (b) recovering the polypeptide.

27. A method for producing a recombinant polypeptide having phytase activity comprising
    (a) cultivating a host cell of claim 4 under conditions conducive for production of the polypeptide; and
    (b) recovering the polypeptide.

28. A method for producing a recombinant polypeptide having phytase activity comprising
    (a) cultivating a host cell of claim 12 under conditions conducive for production of the polypeptide; and
    (b) recovering the polypeptide.

29. A method for producing a recombinant polypeptide having phytase activity comprising
    (a) cultivating a host cell of claim 13 under conditions conducive for production of the polypeptide; and
    (b) recovering the polypeptide.

30. A method for producing a recombinant polypeptide having phytase activity comprising
    (a) cultivating a host cell of claim 14 under conditions conducive for production of the polypeptide; and
    (b) recovering the polypeptide.

31. A method for producing a recombinant polypeptide having phytase activity comprising
    (a) cultivating a host cell of claim 15 under conditions conducive for production of the polypeptide; and
    (b) recovering the polypeptide.

32. A method for producing a recombinant polypeptide having phytase activity comprising
    (a) cultivating a host cell of claim 16 under conditions conducive for production of the polypeptide; and
    (b) recovering the polypeptide.

33. A method for producing a recombinant polypeptide having phytase activity comprising
    (a) cultivating a host cell of claim 17 under conditions conducive for production of the polypeptide; and
    (b) recovering the polypeptide.

34. A method for producing a recombinant polypeptide having phytase activity comprising
    (a) cultivating a host cell of claim 18 under conditions conducive for production of the polypeptide; and
    (b) recovering the polypeptide.

35. A method for producing a recombinant polypeptide having phytase activity comprising
    (a) cultivating a host cell of claim 20 under conditions conducive for production of the polypeptide; and
    (b) recovering the polypeptide.

36. A method for producing a recombinant polypeptide having phytase activity comprising
    (a) cultivating a host cell of claim 21 under conditions conducive for production of the polypeptide; and
    (b) recovering the polypeptide.

37. A method for producing a recombinant polypeptide having phytase activity comprising
    (a) cultivating a host cell of claim 22 under conditions conducive for production of the polypeptide; and
    (b) recovering the polypeptide.

* * * * *

UNITED STATES PATENT AND TRADEMARK OFFICE
CERTIFICATE OF CORRECTION

PATENT NO. : 9,109,211 B2  
APPLICATION NO. : 13/946229  
DATED : August 18, 2015  
INVENTOR(S) : Sjoeholm et al.

Page 1 of 1

It is certified that error appears in the above-identified patent and that said Letters Patent is hereby corrected as shown below:

On the title page item [56], line 5, insert

-- Palmiter et al., Nature, Vol. 300, pages 611-615 (1982) --

Signed and Sealed this
Twenty-second Day of March, 2016

Michelle K. Lee
*Director of the United States Patent and Trademark Office*

SEQUENCE LISTING

```
<160> NUMBER OF SEQ ID NOS: 59

<210> SEQ ID NO 1
<211> LENGTH: 1341
<212> TYPE: DNA
<213> ORGANISM: Buttiauxella gaviniae DSM18930
<220> FEATURE:
<221> NAME/KEY: CDS
<222> LOCATION: (1)..(1338)
<220> FEATURE:
<221> NAME/KEY: sig_peptide
<222> LOCATION: (1)..(99)
<220> FEATURE:
<221> NAME/KEY: mat_peptide
<222> LOCATION: (100)..(1338)

<400> SEQUENCE: 1 atg acg atc tct gcg ttt aac cac aaa aaa ctg acg ctt cac cct ggt       48
Met Thr Ile Ser Ala Phe Asn His Lys Lys Leu Thr Leu His Pro Gly
            -30                 -25                 -20 ctg ttc gta gca ctg agc gcc ata ttt tca tta ggc tct acg gca tat       96
Leu Phe Val Ala Leu Ser Ala Ile Phe Ser Leu Gly Ser Thr Ala Tyr
        -15                 -10                  -5 gcc aat gac act ccc gct tca ggc tac cag gtt gaa aaa gtg gtt atc      144
Ala Asn Asp Thr Pro Ala Ser Gly Tyr Gln Val Glu Lys Val Val Ile
 -1   1               5                  10                  15 ctc agc cgc cac ggt gtg cga gcc ccc acc aaa atg aca cag act atg      192
Leu Ser Arg His Gly Val Arg Ala Pro Thr Lys Met Thr Gln Thr Met
                20                  25                  30 cgc gac gta aca ccc aat acc tgg cca gaa tgg cca gta aaa ctg ggt      240
Arg Asp Val Thr Pro Asn Thr Trp Pro Glu Trp Pro Val Lys Leu Gly
            35                  40                  45 tat atc acg cca cgc ggt gag cat ctg att agc ctg atg ggc ggg ttt      288
Tyr Ile Thr Pro Arg Gly Glu His Leu Ile Ser Leu Met Gly Gly Phe
        50                  55                  60 tat cgc gag aag ttt caa caa cag ggc att tta tcg cag ggc agt tgc      336
Tyr Arg Glu Lys Phe Gln Gln Gln Gly Ile Leu Ser Gln Gly Ser Cys
    65                  70                  75 ccc aca cca aac tca att tat gtc tgg gca gac gtt gat cag cgc acg      384
Pro Thr Pro Asn Ser Ile Tyr Val Trp Ala Asp Val Asp Gln Arg Thr
80                  85                  90                  95 ctt aaa act ggc gaa gct ttc ctg gca ggg ctt gct ccg caa tgt ggt      432
Leu Lys Thr Gly Glu Ala Phe Leu Ala Gly Leu Ala Pro Gln Cys Gly
                100                 105                 110
```

```
tta act att cac cac caa cag aat ctt gaa aaa gcc gat ccg ctg ttc      480
Leu Thr Ile His His Gln Gln Asn Leu Glu Lys Ala Asp Pro Leu Phe
            115                 120                 125 cat ccg gtg aaa gcg ggc acc tgt tca atg gat aaa act cgg ctc caa      528
His Pro Val Lys Ala Gly Thr Cys Ser Met Asp Lys Thr Arg Leu Gln
        130                 135                 140 cag gcc gtt gaa aaa gaa gct caa acg ccc att gag aat ctg aac cag      576
Gln Ala Val Glu Lys Glu Ala Gln Thr Pro Ile Glu Asn Leu Asn Gln
    145                 150                 155 cac tat att ccc tct ctg gct ttg atg aac acg acc ctc aac ttt tcg      624
His Tyr Ile Pro Ser Leu Ala Leu Met Asn Thr Thr Leu Asn Phe Ser
160                 165                 170                 175 acg tct gcc tgg tgt cag aaa cac agc gcg gat aaa agc tgt gat tta      672
Thr Ser Ala Trp Cys Gln Lys His Ser Ala Asp Lys Ser Cys Asp Leu
                180                 185                 190 gcg caa tcc atg ccg agc aag ctg tcg ata aaa gat aat ggc aac aaa      720
Ala Gln Ser Met Pro Ser Lys Leu Ser Ile Lys Asp Asn Gly Asn Lys
            195                 200                 205 gtc gct ctc gat ggg gct gtt ggt ctt tca tcc act ctt gct gaa att      768
Val Ala Leu Asp Gly Ala Val Gly Leu Ser Ser Thr Leu Ala Glu Ile
        210                 215                 220 ttc ctg ctg gaa tat gcg caa ggg atg ccg caa gcg gcc tgg ggg aag      816
Phe Leu Leu Glu Tyr Ala Gln Gly Met Pro Gln Ala Ala Trp Gly Lys
    225                 230                 235 att cat tca gag caa gat tgg gcg gag ttg ctg aaa ctg cat aac gcc      864
Ile His Ser Glu Gln Asp Trp Ala Glu Leu Leu Lys Leu His Asn Ala
240                 245                 250                 255 cag ttt gat ttg atg gcg cgc aca cct tat atc gcc aga cat aac gga      912
Gln Phe Asp Leu Met Ala Arg Thr Pro Tyr Ile Ala Arg His Asn Gly
                260                 265                 270 acg cct tta ttg cag gcc atc agc aac gcg ctg gac cca aac gcc acc      960
Thr Pro Leu Leu Gln Ala Ile Ser Asn Ala Leu Asp Pro Asn Ala Thr
            275                 280                 285 gca agc aag ctg cct gat atc tcg ccg gac aat aag atc ctg ttt att     1008
Ala Ser Lys Leu Pro Asp Ile Ser Pro Asp Asn Lys Ile Leu Phe Ile
        290                 295                 300 gcc gga cac gat acc aat atc gcc aac atc tca ggc atg ctc aac atg     1056
Ala Gly His Asp Thr Asn Ile Ala Asn Ile Ser Gly Met Leu Asn Met
    305                 310                 315 cgc tgg acg cta ccc gga caa cca gat aac act cct cca ggc ggc gct     1104
Arg Trp Thr Leu Pro Gly Gln Pro Asp Asn Thr Pro Pro Gly Gly Ala
320                 325                 330                 335 ttg atc ttt gaa cgc ctg gct gat aaa gct ggg aaa caa tat gtt agt     1152
Leu Ile Phe Glu Arg Leu Ala Asp Lys Ala Gly Lys Gln Tyr Val Ser
                340                 345                 350 gtg agt atg gtg tat cag aca ctc gag cag ttg cgc gct caa aca ccg     1200
Val Ser Met Val Tyr Gln Thr Leu Glu Gln Leu Arg Ala Gln Thr Pro
            355                 360                 365 ctt agc ctt aag gaa ccc gca gga agt gtg cag cta aaa att cct ggc     1248
Leu Ser Leu Lys Glu Pro Ala Gly Ser Val Gln Leu Lys Ile Pro Gly
        370                 375                 380 tgt aat gac cag acg gct gaa gga tat tgc ccg ctg cca aca ttt aaa     1296
Cys Asn Asp Gln Thr Ala Glu Gly Tyr Cys Pro Leu Pro Thr Phe Lys
    385                 390                 395 cgc gtg gtt agc caa agt gaa gaa ccg ggc tgc cag cta cag taa          1341
Arg Val Val Ser Gln Ser Glu Glu Pro Gly Cys Gln Leu Gln
400                 405                 410
```

<210> SEQ ID NO 2

<211> LENGTH: 446
<212> TYPE: PRT
<213> ORGANISM: Buttiauxella gaviniae DSM18930

<400> SEQUENCE: 2

```
Met Thr Ile Ser Ala Phe Asn His Lys Lys Leu Thr Leu His Pro Gly
            -30                 -25                 -20
Leu Phe Val Ala Leu Ser Ala Ile Phe Ser Leu Gly Ser Thr Ala Tyr
        -15                 -10                  -5
Ala Asn Asp Thr Pro Ala Ser Gly Tyr Gln Val Glu Lys Val Val Ile
 -1   1               5                  10                  15
Leu Ser Arg His Gly Val Arg Ala Pro Thr Lys Met Thr Gln Thr Met
                 20                  25                  30
Arg Asp Val Thr Pro Asn Thr Trp Pro Glu Trp Pro Val Lys Leu Gly
             35                  40                  45
Tyr Ile Thr Pro Arg Gly Glu His Leu Ile Ser Leu Met Gly Gly Phe
         50                  55                  60
Tyr Arg Glu Lys Phe Gln Gln Gln Gly Ile Leu Ser Gln Gly Ser Cys
 65                  70                  75
Pro Thr Pro Asn Ser Ile Tyr Val Trp Ala Asp Val Asp Gln Arg Thr
 80                  85                  90                  95
Leu Lys Thr Gly Glu Ala Phe Leu Ala Gly Leu Ala Pro Gln Cys Gly
                100                 105                 110
Leu Thr Ile His His Gln Asn Leu Glu Lys Ala Asp Pro Leu Phe
                115                 120                 125
His Pro Val Lys Ala Gly Thr Cys Ser Met Asp Lys Thr Arg Leu Gln
            130                 135                 140
Gln Ala Val Glu Lys Glu Ala Gln Thr Pro Ile Glu Asn Leu Asn Gln
        145                 150                 155
His Tyr Ile Pro Ser Leu Ala Leu Met Asn Thr Thr Leu Asn Phe Ser
160                 165                 170                 175
Thr Ser Ala Trp Cys Gln Lys His Ser Ala Asp Lys Ser Cys Asp Leu
                180                 185                 190
Ala Gln Ser Met Pro Ser Lys Leu Ser Ile Lys Asp Asn Gly Asn Lys
                195                 200                 205
Val Ala Leu Asp Gly Ala Val Gly Leu Ser Ser Thr Leu Ala Glu Ile
            210                 215                 220
Phe Leu Leu Glu Tyr Ala Gln Gly Met Pro Gln Ala Ala Trp Gly Lys
        225                 230                 235
Ile His Ser Glu Gln Asp Trp Ala Glu Leu Leu Lys Leu His Asn Ala
240                 245                 250                 255
Gln Phe Asp Leu Met Ala Arg Thr Pro Tyr Ile Ala Arg His Asn Gly
                260                 265                 270
Thr Pro Leu Leu Gln Ala Ile Ser Asn Ala Leu Asp Pro Asn Ala Thr
            275                 280                 285
Ala Ser Lys Leu Pro Asp Ile Ser Pro Asp Asn Lys Ile Leu Phe Ile
        290                 295                 300
Ala Gly His Asp Thr Asn Ile Ala Asn Ile Ser Gly Met Leu Asn Met
305                 310                 315
Arg Trp Thr Leu Pro Gly Gln Pro Asp Asn Thr Pro Pro Gly Gly Ala
320                 325                 330                 335
Leu Ile Phe Glu Arg Leu Ala Asp Lys Ala Gly Lys Gln Tyr Val Ser
                340                 345                 350
Val Ser Met Val Tyr Gln Thr Leu Glu Gln Leu Arg Ala Gln Thr Pro
```

-continued

```
                    355                 360                 365
Leu Ser Leu Lys Glu Pro Ala Gly Ser Val Gln Leu Lys Ile Pro Gly
        370                 375                 380

Cys Asn Asp Gln Thr Ala Glu Gly Tyr Cys Pro Leu Pro Thr Phe Lys
385                 390                 395

Arg Val Val Ser Gln Ser Glu Glu Pro Gly Cys Gln Leu Gln
400                 405                 410

<210> SEQ ID NO 3
<211> LENGTH: 1271
<212> TYPE: DNA
<213> ORGANISM: Buttiauxella agrestis DSM18931
<220> FEATURE:
<221> NAME/KEY: CDS
<222> LOCATION: (3)..(1268)
<220> FEATURE:
<221> NAME/KEY: sig_peptide
<222> LOCATION: (3)..(29)
<220> FEATURE:
<221> NAME/KEY: mat_peptide
<222> LOCATION: (30)..(1268)

<400> SEQUENCE: 3 ca ttt tca tta ggt tta acg gca tat gcc agc gac act ccc gct tca       47
   Phe Ser Leu Gly Leu Thr Ala Tyr Ala Ser Asp Thr Pro Ala Ser
       -5                  -1  1                   5 ggc tac cag att gaa aaa gtg gta ata ctc agc cgc cac ggt gtg cga      95
Gly Tyr Gln Ile Glu Lys Val Val Ile Leu Ser Arg His Gly Val Arg
             10                  15                  20 gca ccc acc aaa atg aca cag acc atg cgc gac gta aca ccc aat tcc    143
Ala Pro Thr Lys Met Thr Gln Thr Met Arg Asp Val Thr Pro Asn Ser
         25                  30                  35 tgg ccc gaa tgg ccg gta aaa ttg ggt tat atc acg cca cgc ggt gag    191
Trp Pro Glu Trp Pro Val Lys Leu Gly Tyr Ile Thr Pro Arg Gly Glu
     40                  45                  50 cat ctg att agc ctg atg ggc ggg ttt tat cgc cag aag ttt caa caa    239
His Leu Ile Ser Leu Met Gly Gly Phe Tyr Arg Gln Lys Phe Gln Gln
 55                  60                  65                  70 aag ggc att tta tcg cag ggc agt tgc ccc aca cca aac tca att tat    287
Lys Gly Ile Leu Ser Gln Gly Ser Cys Pro Thr Pro Asn Ser Ile Tyr
                 75                  80                  85 gtc tgg gca gac gtt gat cag cgc acg ctt aaa acg ggc gaa gct ttc    335
Val Trp Ala Asp Val Asp Gln Arg Thr Leu Lys Thr Gly Glu Ala Phe
             90                  95                 100 ctg gca ggg ctt gct ccg caa tgt ggt tta act att cac cac cag cag    383
Leu Ala Gly Leu Ala Pro Gln Cys Gly Leu Thr Ile His His Gln Gln
         105                 110                 115 aat ctt gaa aaa gcc gat ccg ctg ttc cat ccg gtg aaa gcg ggc acc    431
Asn Leu Glu Lys Ala Asp Pro Leu Phe His Pro Val Lys Ala Gly Thr
     120                 125                 130 tgt tca atg gat aaa act caa gtc cag cag gcc gtt gaa aaa gaa gct    479
Cys Ser Met Asp Lys Thr Gln Val Gln Gln Ala Val Glu Lys Glu Ala
135                 140                 145                 150 caa atg ccc att gag aat ctg aac cag cac tat att ccc tct ctg gcc    527
Gln Met Pro Ile Glu Asn Leu Asn Gln His Tyr Ile Pro Ser Leu Ala
                 155                 160                 165 ttg atg aac acg act ctc aac ttt tcg acg tct gcc tgg tgc cag aaa    575
Leu Met Asn Thr Thr Leu Asn Phe Ser Thr Ser Ala Trp Cys Gln Lys
             170                 175                 180 cac agc gcg gat aaa agc tgt gat tta gcg caa tcc atg ccg agc aag    623
His Ser Ala Asp Lys Ser Cys Asp Leu Ala Gln Ser Met Pro Ser Lys
         185                 190                 195
```

```
ctg tcg ata aaa gat aat ggc aac aaa gtc gct ctt gat ggg gcc att    671
Leu Ser Ile Lys Asp Asn Gly Asn Lys Val Ala Leu Asp Gly Ala Ile
    200                 205                 210 ggc ctt tcg tct acg ctt gct gaa att ttc ctg ctg gaa tat gcg caa    719
Gly Leu Ser Ser Thr Leu Ala Glu Ile Phe Leu Leu Glu Tyr Ala Gln
215                 220                 225                 230 ggg atg ccg caa gcg gcg tgg ggg aat att cat tca gag caa gag tgg    767
Gly Met Pro Gln Ala Ala Trp Gly Asn Ile His Ser Glu Gln Glu Trp
                235                 240                 245 gcg tcg cta ttg aaa ctg cat aac acc cag ttt gat ttg atg gcg cgc    815
Ala Ser Leu Leu Lys Leu His Asn Thr Gln Phe Asp Leu Met Ala Arg
            250                 255                 260 aca cct tac atc gcc gca cat aac gga acg ccg tta ttg cag acc atc    863
Thr Pro Tyr Ile Ala Ala His Asn Gly Thr Pro Leu Leu Gln Thr Ile
        265                 270                 275 agc aac gcg ctg gag ccg aaa gcc gac gta agc aaa ctg cct gat atc    911
Ser Asn Ala Leu Glu Pro Lys Ala Asp Val Ser Lys Leu Pro Asp Ile
    280                 285                 290 tca tct gac aat aag atc ctg ttt att gcc gga cac gat acc aat att    959
Ser Ser Asp Asn Lys Ile Leu Phe Ile Ala Gly His Asp Thr Asn Ile
295                 300                 305                 310 gcc aat atc gca ggc atg ctc aac atg cgc tgg acg cta cca ggg caa   1007
Ala Asn Ile Ala Gly Met Leu Asn Met Arg Trp Thr Leu Pro Gly Gln
                315                 320                 325 ccc gat aac acc cca ccg ggc ggc gct tta gtc ttt gag cgt ttg gcc   1055
Pro Asp Asn Thr Pro Pro Gly Gly Ala Leu Val Phe Glu Arg Leu Ala
            330                 335                 340 gat aag tca ggg aaa caa tat att agc gtg agc atg gtg tat cag act   1103
Asp Lys Ser Gly Lys Gln Tyr Ile Ser Val Ser Met Val Tyr Gln Thr
        345                 350                 355 ctt gag cag ttg cgc gct caa aca cca ctt agc ctt aat gaa cca gcg   1151
Leu Glu Gln Leu Arg Ala Gln Thr Pro Leu Ser Leu Asn Glu Pro Ala
    360                 365                 370 ggt agc gta cag cta aaa att cct ggc tgt aac gac cag acg gct gaa   1199
Gly Ser Val Gln Leu Lys Ile Pro Gly Cys Asn Asp Gln Thr Ala Glu
375                 380                 385                 390 gga tac tgc cca ctg tcg acg ttc aca cgc gtg gtt agc caa agc gtg   1247
Gly Tyr Cys Pro Leu Ser Thr Phe Thr Arg Val Val Ser Gln Ser Val
                395                 400                 405 gaa cca ggc tgc cag cta ccg taa                                    1271
Glu Pro Gly Cys Gln Leu Pro
            410

<210> SEQ ID NO 4
<211> LENGTH: 422
<212> TYPE: PRT
<213> ORGANISM: Buttiauxella agrestis DSM18931

<400> SEQUENCE: 4

Phe Ser Leu Gly Leu Thr Ala Tyr Ala Ser Asp Thr Pro Ala Ser Gly
                -5                  -1  1               5

Tyr Gln Ile Glu Lys Val Val Ile Leu Ser Arg His Gly Val Arg Ala
                10                  15                  20

Pro Thr Lys Met Thr Gln Thr Met Arg Asp Val Thr Pro Asn Ser Trp
            25                  30                  35

Pro Glu Trp Pro Val Lys Leu Gly Tyr Ile Thr Pro Arg Gly Glu His
40                  45                  50                  55

Leu Ile Ser Leu Met Gly Gly Phe Tyr Arg Gln Lys Phe Gln Gln Lys
                60                  65                  70
```

```
Gly Ile Leu Ser Gln Gly Ser Cys Pro Thr Pro Asn Ser Ile Tyr Val
            75                  80                  85

Trp Ala Asp Val Asp Gln Arg Thr Leu Lys Thr Gly Glu Ala Phe Leu
        90                  95                 100

Ala Gly Leu Ala Pro Gln Cys Gly Leu Thr Ile His His Gln Gln Asn
    105                 110                 115

Leu Glu Lys Ala Asp Pro Leu Phe His Pro Val Lys Ala Gly Thr Cys
120                 125                 130                 135

Ser Met Asp Lys Thr Gln Val Gln Gln Ala Val Lys Glu Ala Gln
                140                 145                 150

Met Pro Ile Glu Asn Leu Asn Gln His Tyr Ile Pro Ser Leu Ala Leu
                155                 160                 165

Met Asn Thr Thr Leu Asn Phe Ser Thr Ser Ala Trp Cys Gln Lys His
                170                 175                 180

Ser Ala Asp Lys Ser Cys Asp Leu Ala Gln Ser Met Pro Ser Lys Leu
                185                 190                 195

Ser Ile Lys Asp Asn Gly Asn Lys Val Ala Leu Asp Gly Ala Ile Gly
200                 205                 210                 215

Leu Ser Ser Thr Leu Ala Glu Ile Phe Leu Glu Tyr Ala Gln Gly
                220                 225                 230

Met Pro Gln Ala Ala Trp Gly Asn Ile His Ser Glu Gln Glu Trp Ala
                235                 240                 245

Ser Leu Leu Lys Leu His Asn Thr Gln Phe Asp Leu Met Ala Arg Thr
                250                 255                 260

Pro Tyr Ile Ala Ala His Asn Gly Thr Pro Leu Leu Gln Thr Ile Ser
                265                 270                 275

Asn Ala Leu Glu Pro Lys Ala Asp Val Ser Lys Leu Pro Asp Ile Ser
280                 285                 290                 295

Ser Asp Asn Lys Ile Leu Phe Ile Ala Gly His Asp Thr Asn Ile Ala
                300                 305                 310

Asn Ile Ala Gly Met Leu Asn Met Arg Trp Thr Leu Pro Gly Gln Pro
                315                 320                 325

Asp Asn Thr Pro Pro Gly Gly Ala Leu Val Phe Glu Arg Leu Ala Asp
                330                 335                 340

Lys Ser Gly Lys Gln Tyr Ile Ser Val Ser Met Val Tyr Gln Thr Leu
345                 350                 355

Glu Gln Leu Arg Ala Gln Thr Pro Leu Ser Leu Asn Glu Pro Ala Gly
360                 365                 370                 375

Ser Val Gln Leu Lys Ile Pro Gly Cys Asn Asp Gln Thr Ala Glu Gly
                380                 385                 390

Tyr Cys Pro Leu Ser Thr Phe Thr Arg Val Val Ser Gln Ser Val Glu
                395                 400                 405

Pro Gly Cys Gln Leu Pro
        410

<210> SEQ ID NO 5
<211> LENGTH: 1341
<212> TYPE: DNA
<213> ORGANISM: Buttiauxella agrestis DSM18932
<220> FEATURE:
<221> NAME/KEY: CDS
<222> LOCATION: (1)..(1338)
<220> FEATURE:
<221> NAME/KEY: sig_peptide
<222> LOCATION: (1)..(99)
<220> FEATURE:
```

-continued

```
<221> NAME/KEY: mat_peptide
<222> LOCATION: (100)..(1338)

<400> SEQUENCE: 5 atg acg ttc tct gcg ttt aac cgc aaa aaa ctg acg ctt cac cct ggt       48
Met Thr Phe Ser Ala Phe Asn Arg Lys Lys Leu Thr Leu His Pro Gly
        -30                 -25                 -20 ctg ttc gta gca ctg agc gcc ata ttt tca tta ggc tct acg gcc tat       96
Leu Phe Val Ala Leu Ser Ala Ile Phe Ser Leu Gly Ser Thr Ala Tyr
    -15                 -10                  -5 gcc aac gac act ccc gct tca ggc tac cag gtt gaa aaa gtg gta atc      144
Ala Asn Asp Thr Pro Ala Ser Gly Tyr Gln Val Glu Lys Val Val Ile
 -1  1               5                  10                  15 ctc agc cgc cac ggg gtg cga gca ccc acc aaa atg aca cag acc atg      192
Leu Ser Arg His Gly Val Arg Ala Pro Thr Lys Met Thr Gln Thr Met
                 20                  25                  30 cgc gac gta aca ccc aat acc tgg ccc gaa tgg cca gta aaa ttg ggt      240
Arg Asp Val Thr Pro Asn Thr Trp Pro Glu Trp Pro Val Lys Leu Gly
                     35                  40                  45 tat atc acg cca cgc ggt gag cat ctg att agc ctg atg ggc ggg ttt      288
Tyr Ile Thr Pro Arg Gly Glu His Leu Ile Ser Leu Met Gly Gly Phe
         50                  55                  60 tat cgc gag aag ttt caa caa cag ggc att tta tcg cag ggc agt tgc      336
Tyr Arg Glu Lys Phe Gln Gln Gln Gly Ile Leu Ser Gln Gly Ser Cys
 65                  70                  75 ccc gca cca aac tca att tat gtc tgg gca gac gtt gat cag cgc acg      384
Pro Ala Pro Asn Ser Ile Tyr Val Trp Ala Asp Val Asp Gln Arg Thr
 80                  85                  90                  95 ctt aaa act ggc gaa gct ttc ctg gca ggg ctt gct ccg caa tgt ggt      432
Leu Lys Thr Gly Glu Ala Phe Leu Ala Gly Leu Ala Pro Gln Cys Gly
                100                 105                 110 tta act att cac cac cag cag aat ctt gaa aaa gcc gat ccg ctg ttc      480
Leu Thr Ile His His Gln Gln Asn Leu Glu Lys Ala Asp Pro Leu Phe
            115                 120                 125 cat ccg gtg aaa gcg ggc acg tgt tca atg gat aaa act cag gtc caa      528
His Pro Val Lys Ala Gly Thr Cys Ser Met Asp Lys Thr Gln Val Gln
        130                 135                 140 cag gcc gtt gaa aaa gaa gct caa acc ccc att gat aat ctg aat cag      576
Gln Ala Val Glu Lys Glu Ala Gln Thr Pro Ile Asp Asn Leu Asn Gln
145                 150                 155 cac tat att ccc tct ctg gcc ttg atg aac acg acc ctc aac ttt tcg      624
His Tyr Ile Pro Ser Leu Ala Leu Met Asn Thr Thr Leu Asn Phe Ser
160                 165                 170                 175 acg tct gcc tgg tgt cag aaa cac agc gcg gat aaa agc tgt gat tta      672
Thr Ser Ala Trp Cys Gln Lys His Ser Ala Asp Lys Ser Cys Asp Leu
                180                 185                 190 gcg caa tcc atg ccg agc aag ctg tcg ata aaa gat aat ggc aac aaa      720
Ala Gln Ser Met Pro Ser Lys Leu Ser Ile Lys Asp Asn Gly Asn Lys
            195                 200                 205 gtc gct ctc gac ggg gcc att ggc ctt tcg tct acg ctt gct gaa att      768
Val Ala Leu Asp Gly Ala Ile Gly Leu Ser Ser Thr Leu Ala Glu Ile
        210                 215                 220 ttc ctg ctg gaa tat gcg caa ggg atg ccg caa gcg gcg tgg ggg aat      816
Phe Leu Leu Glu Tyr Ala Gln Gly Met Pro Gln Ala Ala Trp Gly Asn
    225                 230                 235 att cat tca gag caa gag tgg gcg tcg cta ctg aaa ctg cat aac gcc      864
Ile His Ser Glu Gln Glu Trp Ala Ser Leu Leu Lys Leu His Asn Ala
240                 245                 250                 255 cag ttt gat ttg atg gcg cgc aca cct tac atc gcc aca cat aac ggc      912
Gln Phe Asp Leu Met Ala Arg Thr Pro Tyr Ile Ala Thr His Asn Gly
```

```
                 260                 265                 270
acg cct tta ttg cag acc atc agc aac gcg ctg gag ccg aaa gcc gac        960
Thr Pro Leu Leu Gln Thr Ile Ser Asn Ala Leu Glu Pro Lys Ala Asp
            275                 280                 285 gta agc aaa ctg cct ggt atc tca cct gac aat aag atc ctg ttt ctt       1008
Val Ser Lys Leu Pro Gly Ile Ser Pro Asp Asn Lys Ile Leu Phe Leu
        290                 295                 300 gcc ggg cac gat acc aat att gcc aat atc gca ggc atg ctc aac atg       1056
Ala Gly His Asp Thr Asn Ile Ala Asn Ile Ala Gly Met Leu Asn Met
    305                 310                 315 cgc tgg acg cta cca ggg caa ccc gat aac acc cct ccg ggc ggc gct       1104
Arg Trp Thr Leu Pro Gly Gln Pro Asp Asn Thr Pro Pro Gly Gly Ala
320                 325                 330                 335 tta gtc ttt gag cgt ttg gcc gat aag tca ggg aaa caa tat gtt agc       1152
Leu Val Phe Glu Arg Leu Ala Asp Lys Ser Gly Lys Gln Tyr Val Ser
                340                 345                 350 gtg agc atg gtg tat cag act ctc gag cag ttg cga tcc caa aca cca       1200
Val Ser Met Val Tyr Gln Thr Leu Glu Gln Leu Arg Ser Gln Thr Pro
            355                 360                 365 ctt agc ctt aat caa cct gcg gga agc gtt cag cta aaa att cct ggc       1248
Leu Ser Leu Asn Gln Pro Ala Gly Ser Val Gln Leu Lys Ile Pro Gly
        370                 375                 380 tgt aac gac cag acg gct gaa gga tac tgc cca ctg tcg aca ttc aca       1296
Cys Asn Asp Gln Thr Ala Glu Gly Tyr Cys Pro Leu Ser Thr Phe Thr
    385                 390                 395 cgc gtg gtt agc caa agc gtg gaa ccc ggc tgc cag cta cag taa           1341
Arg Val Val Ser Gln Ser Val Glu Pro Gly Cys Gln Leu Gln
400                 405                 410

<210> SEQ ID NO 6
<211> LENGTH: 446
<212> TYPE: PRT
<213> ORGANISM: Buttiauxella agrestis DSM18932

<400> SEQUENCE: 6

Met Thr Phe Ser Ala Phe Asn Arg Lys Lys Leu Thr Leu His Pro Gly
            -30                 -25                 -20

Leu Phe Val Ala Leu Ser Ala Ile Phe Ser Leu Gly Ser Thr Ala Tyr
        -15                 -10                  -5

Ala Asn Asp Thr Pro Ala Ser Gly Tyr Gln Val Glu Lys Val Val Ile
 -1   1               5                  10                  15

Leu Ser Arg His Gly Val Arg Ala Pro Thr Lys Met Thr Gln Thr Met
                20                  25                  30

Arg Asp Val Thr Pro Asn Thr Trp Pro Glu Trp Pro Val Lys Leu Gly
            35                  40                  45

Tyr Ile Thr Pro Arg Gly Glu His Leu Ile Ser Leu Met Gly Gly Phe
        50                  55                  60

Tyr Arg Glu Lys Phe Gln Gln Gln Gly Ile Leu Ser Gln Gly Ser Cys
 65                  70                  75

Pro Ala Pro Asn Ser Ile Tyr Val Trp Ala Asp Val Asp Gln Arg Thr
 80                  85                  90                  95

Leu Lys Thr Gly Glu Ala Phe Leu Ala Gly Leu Ala Pro Gln Cys Gly
                100                 105                 110

Leu Thr Ile His His Gln Gln Asn Leu Glu Lys Ala Asp Pro Leu Phe
            115                 120                 125

His Pro Val Lys Ala Gly Thr Cys Ser Met Asp Lys Thr Gln Val Gln
        130                 135                 140
```

```
Gln Ala Val Glu Lys Glu Ala Gln Thr Pro Ile Asp Asn Leu Asn Gln
    145                 150                 155
His Tyr Ile Pro Ser Leu Ala Leu Met Asn Thr Thr Leu Asn Phe Ser
160                 165                 170                 175
Thr Ser Ala Trp Cys Gln Lys His Ser Ala Asp Lys Ser Cys Asp Leu
                180                 185                 190
Ala Gln Ser Met Pro Ser Lys Leu Ser Ile Lys Asp Asn Gly Asn Lys
            195                 200                 205
Val Ala Leu Asp Gly Ala Ile Gly Leu Ser Ser Thr Leu Ala Glu Ile
        210                 215                 220
Phe Leu Leu Glu Tyr Ala Gln Gly Met Pro Gln Ala Ala Trp Gly Asn
225                 230                 235
Ile His Ser Glu Gln Glu Trp Ala Ser Leu Leu Lys Leu His Asn Ala
240                 245                 250                 255
Gln Phe Asp Leu Met Ala Arg Thr Pro Tyr Ile Ala Thr His Asn Gly
                260                 265                 270
Thr Pro Leu Leu Gln Thr Ile Ser Asn Ala Leu Glu Pro Lys Ala Asp
            275                 280                 285
Val Ser Lys Leu Pro Gly Ile Ser Pro Asp Asn Lys Ile Leu Phe Leu
        290                 295                 300
Ala Gly His Asp Thr Asn Ile Ala Asn Ile Ala Gly Met Leu Asn Met
305                 310                 315
Arg Trp Thr Leu Pro Gly Gln Pro Asp Asn Thr Pro Pro Gly Gly Ala
320                 325                 330                 335
Leu Val Phe Glu Arg Leu Ala Asp Lys Ser Gly Lys Gln Tyr Val Ser
                340                 345                 350
Val Ser Met Val Tyr Gln Thr Leu Glu Gln Leu Arg Ser Gln Thr Pro
            355                 360                 365
Leu Ser Leu Asn Gln Pro Ala Gly Ser Val Gln Leu Lys Ile Pro Gly
        370                 375                 380
Cys Asn Asp Gln Thr Ala Glu Gly Tyr Cys Pro Leu Ser Thr Phe Thr
385                 390                 395
Arg Val Val Ser Gln Ser Val Glu Pro Gly Cys Gln Leu Gln
400                 405                 410

<210> SEQ ID NO 7
<211> LENGTH: 81
<212> TYPE: DNA
<213> ORGANISM: Bacillus licheniformis
<220> FEATURE:
<221> NAME/KEY: sig_peptide
<222> LOCATION: (1)..(81)
<220> FEATURE:
<221> NAME/KEY: CDS
<222> LOCATION: (1)..(81)

<400> SEQUENCE: 7 atg aag aaa ccg ttg ggg aaa att gtc gca agc acc gca cta ctc att      48
Met Lys Lys Pro Leu Gly Lys Ile Val Ala Ser Thr Ala Leu Leu Ile
1               5                   10                  15 tct gtt gct ttt agt tca tcg atc gca tcg gct                          81
Ser Val Ala Phe Ser Ser Ser Ile Ala Ser Ala
            20                  25

<210> SEQ ID NO 8
<211> LENGTH: 27
<212> TYPE: PRT
<213> ORGANISM: Bacillus licheniformis
```

-continued

<400> SEQUENCE: 8

Met Lys Lys Pro Leu Gly Lys Ile Val Ala Ser Thr Ala Leu Leu Ile
1               5                   10                  15

Ser Val Ala Phe Ser Ser Ser Ile Ala Ser Ala
            20                  25

<210> SEQ ID NO 9
<211> LENGTH: 23
<212> TYPE: DNA
<213> ORGANISM: Artificial
<220> FEATURE:
<223> OTHER INFORMATION: Primer 2123
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 9
catggtgtgc gngcnccnac naa                                        23

<210> SEQ ID NO 10
<211> LENGTH: 27
<212> TYPE: DNA
<213> ORGANISM: Artificial
<220> FEATURE:
<223> OTHER INFORMATION: Primer 2065
<220> FEATURE:
<221> NAME/KEY: misc_feature
<223> OTHER INFORMATION: Y means T or C; R means A or G
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t

<400> SEQUENCE: 10
cccaccaggn ggngtrttrt cnggytg                                    27

<210> SEQ ID NO 11
<211> LENGTH: 18
<212> TYPE: DNA
<213> ORGANISM: Artificial
<220> FEATURE:
<223> OTHER INFORMATION: Primer 2138

<400> SEQUENCE: 11
attgcggagc aagccctg                                              18

<210> SEQ ID NO 12
<211> LENGTH: 20
<212> TYPE: DNA

```
<213> ORGANISM: Artificial
<220> FEATURE:
<223> OTHER INFORMATION: Primer 2139
<220> FEATURE:
<221> NAME/KEY: misc_feature
<222> LOCATION: (17)..(17)
<223> OTHER INFORMATION: n is a, c, g, or t

<400> SEQUENCE: 12
tcgccagttt taagcgngcg                                              20

<210> SEQ ID NO 13
<211> LENGTH: 20
<212> TYPE: DNA
<213> ORGANISM: Artificial
<220> FEATURE:
<223> OTHER INFORMATION: Primer 2136

<400> SEQUENCE: 13
tggaatatgc gcaagggatg                                              20

<210> SEQ ID NO 14
<211> LENGTH: 22
<212> TYPE: DNA
<213> ORGANISM: Artificial
<220> FEATURE:
<223> OTHER INFORMATION: Primer 2137

<400> SEQUENCE: 14
tgggggtcag agcaagagtg gg                                           22

<210> SEQ ID NO 15
<211> LENGTH: 29
<212> TYPE: DNA
<213> ORGANISM: Artificial
<220> FEATURE:
<223> OTHER INFORMATION: Primer 315
<220> FEATURE:
<221> NAME/KEY: misc_feature
<223> OTHER INFORMATION: Y means T or C; M means A or C
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t

<400> SEQUENCE: 15
cgcgtggtga ttgtgtccmg ncayggngt                                    29

<210> SEQ ID NO 16
<211> LENGTH: 28
<212> TYPE: DNA
<213> ORGANISM: Artificial
<220> FEATURE:
<223> OTHER INFORMATION: Primer 316
<220> FEATURE:
<221> NAME/KEY: misc_feature
<223> OTHER INFORMATION: R means A or G
<220> FEATURE:
<221> NAME/KEY: misc_feature
<222> LOCATION: (20)..(20)
<223> OTHER INFORMATION: n is a, c, g, or t

<400> SEQUENCE: 16
ccaggttggt atcatggccn gcdatraa                                     28
```

```
<210> SEQ ID NO 17
<211> LENGTH: 18
<212> TYPE: DNA
<213> ORGANISM: Artificial
<220> FEATURE:
<223> OTHER INFORMATION: Primer 1978

<400> SEQUENCE: 17
cgcgtggtga ttgtgtcc                                                 18

<210> SEQ ID NO 18
<211> LENGTH: 19
<212> TYPE: DNA
<213> ORGANISM: Artificial
<220> FEATURE:
<223> OTHER INFORMATION: Primer 1979

<400> SEQUENCE: 18
ccaggttggt atcatggcc                                                19

<210> SEQ ID NO 19
<211> LENGTH: 21
<212> TYPE: DNA
<213> ORGANISM: Artificial
<220> FEATURE:
<223> OTHER INFORMATION: Primer 2029

<400> SEQUENCE: 19
aagcttcgcc agttttaagc g                                             21

<210> SEQ ID NO 20
<211> LENGTH: 23
<212> TYPE: DNA
<213> ORGANISM: Artificial
<220> FEATURE:
<223> OTHER INFORMATION: Primer 2030

<400> SEQUENCE: 20
ttgagtttgg tgtgggcaa ctg                                            23

<210> SEQ ID NO 21
<211> LENGTH: 20
<212> TYPE: DNA
<213> ORGANISM: Artificial
<220> FEATURE:
<223> OTHER INFORMATION: Primer 2031

<400> SEQUENCE: 21
tggcaacaaa gtcgctctcg                                               20

<210> SEQ ID NO 22
<211> LENGTH: 22
<212> TYPE: DNA
<213> ORGANISM: Artificial
<220> FEATURE:
<223> OTHER INFORMATION: Primer 2032

<400> SEQUENCE: 22
tcctgctgga atatgcgcaa gg                                            22

<210> SEQ ID NO 23
<211> LENGTH: 19
<212> TYPE: DNA
<213> ORGANISM: Artificial
<220> FEATURE:
<223> OTHER INFORMATION: Primer 2017
```

```
<400> SEQUENCE: 23
ttcgcccgtt ttaagcgtg                                                    19

<210> SEQ ID NO 24
<211> LENGTH: 22
<212> TYPE: DNA
<213> ORGANISM: Artificial
<220> FEATURE:
<223> OTHER INFORMATION: Primer 2018

<400> SEQUENCE: 24
actgccctgc gataaaatgc cc                                                22

<210> SEQ ID NO 25
<211> LENGTH: 20
<212> TYPE: DNA
<213> ORGANISM: Artificial
<220> FEATURE:
<223> OTHER INFORMATION: Primer 2019

<400> SEQUENCE: 25
tttcctgctg gaatatgcgc                                                   20

<210> SEQ ID NO 26
<211> LENGTH: 21
<212> TYPE: DNA
<213> ORGANISM: Artificial
<220> FEATURE:
<223> OTHER INFORMATION: Primer 2020

<400> SEQUENCE: 26
ttgatggcgc gcacacctta c                                                 21

<210> SEQ ID NO 27
<211> LENGTH: 446
<212> TYPE: PRT
<213> ORGANISM: Artificial sequence
<220> FEATURE:
<223> OTHER INFORMATION: Synthetic construct

<400> SEQUENCE: 27
```

| Met | Thr | Ile | Ser | Ala | Phe | Asn | Arg | Lys | Lys | Leu | Thr | Leu | His | Pro | Gly |
|---|---|---|---|---|---|---|---|---|---|---|---|---|---|---|---|
| 1 | | | | 5 | | | | | 10 | | | | | 15 | |

| Leu | Phe | Val | Ala | Leu | Ser | Ala | Ile | Phe | Ser | Leu | Gly | Ser | Thr | Ala | Tyr |
|---|---|---|---|---|---|---|---|---|---|---|---|---|---|---|---|
| | | | 20 | | | | | 25 | | | | | 30 | | |

| Ala | Asn | Asp | Thr | Pro | Ala | Ser | Gly | Tyr | Gln | Val | Glu | Lys | Val | Val | Ile |
|---|---|---|---|---|---|---|---|---|---|---|---|---|---|---|---|
| | | | 35 | | | | | 40 | | | | | 45 | | |

| Leu | Ser | Arg | His | Gly | Val | Arg | Ala | Pro | Thr | Lys | Met | Thr | Gln | Thr | Met |
|---|---|---|---|---|---|---|---|---|---|---|---|---|---|---|---|
| 50 | | | | | 55 | | | | | 60 | | | | | |

| Arg | Asp | Val | Thr | Pro | Asn | Thr | Trp | Pro | Glu | Trp | Pro | Val | Lys | Leu | Gly |
|---|---|---|---|---|---|---|---|---|---|---|---|---|---|---|---|
| 65 | | | | | 70 | | | | | 75 | | | | | 80 |

| Tyr | Ile | Thr | Pro | Arg | Gly | Glu | His | Leu | Ile | Ser | Leu | Met | Gly | Gly | Phe |
|---|---|---|---|---|---|---|---|---|---|---|---|---|---|---|---|
| | | | | 85 | | | | | 90 | | | | | 95 | |

| Tyr | Arg | Gln | Lys | Phe | Gln | Gln | Gln | Gly | Ile | Leu | Ser | Gln | Gly | Ser | Cys |
|---|---|---|---|---|---|---|---|---|---|---|---|---|---|---|---|
| | | | 100 | | | | | 105 | | | | | 110 | | |

| Pro | Thr | Pro | Asn | Ser | Ile | Tyr | Val | Trp | Ala | Asp | Val | Asp | Gln | Arg | Thr |
|---|---|---|---|---|---|---|---|---|---|---|---|---|---|---|---|
| | | | 115 | | | | | 120 | | | | | 125 | | |

| Leu | Lys | Thr | Gly | Glu | Ala | Phe | Leu | Ala | Gly | Leu | Ala | Pro | Glu | Cys | His |
|---|---|---|---|---|---|---|---|---|---|---|---|---|---|---|---|
| | | 130 | | | | | 135 | | | | | 140 | | | |

| Leu | Thr | Ile | His | His | Gln | Gln | Asp | Ile | Lys | Lys | Ala | Asp | Pro | Leu | Phe |
|---|---|---|---|---|---|---|---|---|---|---|---|---|---|---|---|
| 145 | | | | | 150 | | | | | 155 | | | | | 160 |

His Pro Val Lys Ala Gly Thr Cys Ser Met Asp Lys Thr Gln Val Gln
            165                 170                 175

Gln Ala Val Glu Lys Glu Ala Gln Thr Pro Ile Asp Asn Leu Asn Gln
        180                 185                 190

His Tyr Ile Pro Phe Leu Ala Leu Met Asn Thr Thr Leu Asn Phe Ser
    195                 200                 205

Thr Ser Ala Trp Cys Gln Lys His Ser Ala Asp Lys Ser Cys Asp Leu
210                 215                 220

Gly Leu Ser Met Pro Ser Lys Leu Ser Ile Lys Asp Asn Gly Asn Lys
225                 230                 235                 240

Val Ala Leu Asp Gly Ala Ile Gly Leu Ser Ser Thr Leu Ala Glu Ile
            245                 250                 255

Phe Leu Leu Glu Tyr Ala Gln Gly Met Pro Gln Ala Ala Trp Gly Asn
        260                 265                 270

Ile His Ser Glu Gln Glu Trp Ala Ser Leu Leu Lys Leu His Asn Val
    275                 280                 285

Gln Phe Asp Leu Met Ala Arg Thr Pro Tyr Ile Ala Arg His Asn Gly
290                 295                 300

Thr Pro Leu Leu Gln Ala Ile Ser Asn Ala Leu Asn Pro Asn Ala Thr
305                 310                 315                 320

Glu Ser Lys Leu Pro Asp Ile Ser Pro Asp Asn Lys Ile Leu Phe Ile
            325                 330                 335

Ala Gly His Asp Thr Asn Ile Ala Asn Ile Ala Gly Met Leu Asn Met
        340                 345                 350

Arg Trp Thr Leu Pro Gly Gln Pro Asp Asn Thr Pro Pro Gly Gly Ala
    355                 360                 365

Leu Val Phe Glu Arg Leu Ala Asp Lys Ser Gly Lys Gln Tyr Val Ser
370                 375                 380

Val Ser Met Val Tyr Gln Thr Leu Glu Gln Leu Arg Ser Gln Thr Pro
385                 390                 395                 400

Leu Ser Leu Asn Gln Pro Ala Gly Ser Val Gln Leu Lys Ile Pro Gly
            405                 410                 415

Cys Asn Asp Gln Thr Ala Glu Gly Tyr Cys Pro Leu Ser Thr Phe Thr
        420                 425                 430

Arg Val Val Ser Gln Ser Val Glu Pro Gly Cys Gln Leu Gln
    435                 440                 445

<210> SEQ ID NO 28
<211> LENGTH: 446
<212> TYPE: PRT
<213> ORGANISM: Artificial sequence
<220> FEATURE:
<223> OTHER INFORMATION: Synthetic construct

<400> SEQUENCE: 28

Met Thr Ile Ser Ala Phe Asn Arg Lys Lys Leu Thr Leu His Pro Gly
1               5                   10                  15

Leu Phe Val Ala Leu Ser Ala Ile Phe Ser Leu Gly Ser Thr Ala Tyr
            20                  25                  30

Ala Asn Asp Thr Pro Ala Ser Gly Tyr Gln Val Glu Lys Val Val Ile
        35                  40                  45

Leu Ser Arg His Gly Val Arg Ala Pro Thr Glu Met Thr Gln Thr Met
    50                  55                  60

Arg Asp Val Thr Pro Asn Thr Trp Pro Glu Trp Pro Val Lys Leu Gly
65                  70                  75                  80

Tyr Ile Thr Pro Arg Gly Glu His Leu Ile Ser Leu Met Gly Gly Phe
                85                  90                  95

Tyr Arg Gln Lys Phe Gln Gln Gly Ile Leu Ser Gln Gly Ser Cys
    100                 105                 110

Pro Thr Pro Asn Ser Ile Tyr Val Trp Ala Asp Val Asp Gln Arg Thr
    115                 120                 125

Leu Lys Thr Gly Glu Ala Phe Leu Ala Gly Leu Ala Pro Glu Cys His
130                 135                 140

Leu Thr Ile His His Gln Gln Asp Ile Lys Lys Ala Asp Pro Leu Phe
145                 150                 155                 160

His Pro Val Lys Ala Gly Thr Cys Ser Met Asp Lys Thr Gln Val Gln
                165                 170                 175

Gln Ala Val Glu Lys Glu Ala Gln Thr Pro Ile Asp Asn Leu Asn Gln
                180                 185                 190

His Tyr Ile Pro Phe Leu Ala Leu Met Asn Thr Thr Leu Asn Phe Ser
                195                 200                 205

Thr Ser Ala Trp Cys Gln Lys His Ser Ala Asp Lys Ser Cys Asp Leu
210                 215                 220

Gly Leu Ser Met Pro Ser Lys Leu Ser Ile Lys Asp Asn Gly Asn Lys
225                 230                 235                 240

Val Ala Leu Asp Gly Ala Ile Gly Leu Ser Ser Thr Leu Ala Glu Ile
                245                 250                 255

Phe Leu Leu Glu Tyr Ala Gln Gly Met Pro Gln Ala Ala Trp Gly Asn
                260                 265                 270

Ile His Ser Glu Gln Glu Trp Ala Ser Leu Leu Lys Leu His Asn Val
                275                 280                 285

Gln Phe Asp Leu Met Ala Arg Thr Pro Tyr Ile Ala Arg His Asn Gly
290                 295                 300

Thr Pro Leu Leu Gln Ala Ile Ser Asn Ala Leu Asn Pro Asn Ala Thr
305                 310                 315                 320

Glu Ser Lys Leu Pro Asp Ile Ser Pro Asp Asn Lys Ile Leu Phe Ile
                325                 330                 335

Ala Gly His Asp Thr Asn Ile Ala Asn Ile Ala Gly Met Leu Asn Met
                340                 345                 350

Arg Trp Thr Leu Pro Gly Gln Pro Asp Asn Thr Pro Pro Gly Gly Ala
                355                 360                 365

Leu Val Phe Glu Arg Leu Ala Asp Lys Ser Gly Lys Gln Tyr Val Ser
    370                 375                 380

Val Ser Met Val Tyr Gln Thr Leu Glu Gln Leu Arg Ser Gln Thr Pro
385                 390                 395                 400

Leu Ser Leu Asn Gln Pro Ala Gly Ser Val Gln Leu Lys Ile Pro Gly
                405                 410                 415

Cys Asn Asp Gln Thr Ala Glu Gly Tyr Cys Pro Leu Ser Thr Phe Thr
                420                 425                 430

Arg Val Val Ser Gln Ser Val Glu Pro Gly Cys Gln Leu Gln
                435                 440                 445

<210> SEQ ID NO 29
<211> LENGTH: 446
<212> TYPE: PRT
<213> ORGANISM: Artificial sequence
<220> FEATURE:
<223> OTHER INFORMATION: Synthetic construct

<400> SEQUENCE: 29

```
Met Thr Ile Ser Ala Phe Asn Arg Lys Lys Leu Thr Leu His Pro Gly
1               5                   10                  15

Leu Phe Val Ala Leu Ser Ala Ile Phe Ser Leu Gly Ser Thr Ala Tyr
                20                  25                  30

Ala Asn Asp Thr Pro Ala Ser Gly Tyr Gln Val Glu Lys Val Val Ile
            35                  40                  45

Leu Ser Arg His Gly Val Arg Ala Pro Thr Lys Met Thr Gln Thr Met
    50                  55                  60

Arg Asp Val Thr Pro Asn Thr Trp Pro Glu Trp Pro Val Lys Leu Gly
65                  70                  75                  80

Tyr Ile Thr Pro Arg Gly Glu His Leu Ile Ser Leu Met Gly Gly Phe
                85                  90                  95

Tyr Arg Gln Lys Phe Gln Gln Gln Gly Ile Leu Ser Gln Gly Ser Cys
            100                 105                 110

Pro Thr Pro Asn Ser Ile Tyr Val Trp Ala Asp Val Asp Gln Arg Thr
                115                 120                 125

Leu Lys Thr Gly Glu Ala Phe Leu Ala Gly Leu Ala Pro Glu Cys His
    130                 135                 140

Leu Thr Ile His His Gln Gln Asp Ile Lys Lys Ala Asp Pro Leu Phe
145                 150                 155                 160

His Pro Val Lys Ala Gly Val Cys Ser Met Asp Lys Thr Gln Val Gln
                165                 170                 175

Gln Ala Val Glu Lys Glu Ala Gln Thr Pro Ile Asp Asn Leu Asn Gln
            180                 185                 190

His Tyr Ile Pro Phe Leu Ala Leu Met Asn Thr Thr Leu Asn Phe Ser
            195                 200                 205

Thr Ser Ala Trp Cys Gln Lys His Ser Ala Asp Lys Ser Cys Asp Leu
210                 215                 220

Gly Leu Ser Met Pro Ser Lys Leu Ser Ile Lys Asp Asn Gly Asn Lys
225                 230                 235                 240

Val Ala Leu Asp Gly Ala Ile Gly Leu Ser Ser Thr Leu Ala Glu Ile
                245                 250                 255

Phe Leu Leu Glu Tyr Ala Gln Gly Met Pro Gln Ala Ala Trp Gly Asn
            260                 265                 270

Ile His Ser Glu Gln Glu Trp Ala Ser Leu Leu Lys Leu His Asn Val
            275                 280                 285

Gln Phe Asp Leu Met Ala Arg Thr Pro Tyr Ile Ala Arg His Asn Gly
    290                 295                 300

Thr Pro Leu Leu Gln Ala Ile Ser Asn Ala Leu Asn Pro Asn Ala Thr
305                 310                 315                 320

Glu Ser Lys Leu Pro Asp Ile Ser Pro Asp Asn Lys Ile Leu Phe Ile
                325                 330                 335

Ala Gly His Asp Thr Asn Ile Ala Asn Ile Ala Gly Met Leu Asn Met
            340                 345                 350

Arg Trp Thr Leu Pro Gly Gln Pro Asp Asn Thr Pro Pro Gly Gly Ala
                355                 360                 365

Leu Val Phe Glu Arg Leu Ala Asp Lys Ser Gly Lys Gln Tyr Val Ser
    370                 375                 380

Val Ser Met Val Tyr Gln Thr Leu Glu Gln Leu Arg Ser Gln Thr Pro
385                 390                 395                 400

Leu Ser Leu Asn Gln Pro Ala Gly Ser Val Gln Leu Lys Ile Pro Gly
                405                 410                 415
```

```
Cys Asn Asp Gln Thr Ala Glu Gly Tyr Cys Pro Leu Ser Thr Phe Thr
            420                 425                 430

Arg Val Val Ser Gln Ser Val Glu Pro Gly Cys Gln Leu Gln
        435                 440                 445

<210> SEQ ID NO 30
<211> LENGTH: 446
<212> TYPE: PRT
<213> ORGANISM: Artificial sequence
<220> FEATURE:
<223> OTHER INFORMATION: Synthetic construct

<400> SEQUENCE: 30

Met Thr Ile Ser Ala Phe Asn Arg Lys Lys Leu Thr Leu His Pro Gly
1               5                   10                  15

Leu Phe Val Ala Leu Ser Ala Ile Phe Ser Leu Gly Ser Thr Ala Tyr
            20                  25                  30

Ala Asn Asp Thr Pro Ala Ser Gly Tyr Gln Val Glu Lys Val Val Ile
            35                  40                  45

Leu Ser Arg His Gly Val Arg Ala Pro Thr Lys Met Thr Gln Thr Met
        50                  55                  60

Arg Asp Val Thr Pro Asn Thr Trp Pro Glu Trp Pro Val Lys Leu Gly
65                  70                  75                  80

Tyr Ile Thr Pro Arg Gly Glu His Leu Ile Ser Leu Met Gly Gly Phe
                85                  90                  95

Tyr Arg Gln Lys Phe Gln Gln Gln Gly Ile Leu Ser Gln Gly Ser Cys
            100                 105                 110

Pro Thr Pro Asn Ser Ile Tyr Val Trp Ala Asp Val Asp Gln Arg Thr
        115                 120                 125

Leu Lys Thr Gly Glu Ala Phe Leu Ala Gly Leu Ala Pro Glu Cys His
    130                 135                 140

Leu Thr Ile His His Gln Gln Asp Ile Lys Lys Ala Asp Pro Leu Phe
145                 150                 155                 160

His Pro Val Lys Ala Gly Thr Cys Ser Met Asp Lys Thr Gln Val Gln
                165                 170                 175

Gln Ala Val Glu Lys Glu Ala Gln Thr Pro Ile Asp Asn Leu Asn Gln
            180                 185                 190

His Tyr Ile Pro Phe Leu Ala Leu Met Asn Thr Thr Leu Asn Phe Ser
        195                 200                 205

Thr Ser Ala Trp Cys Gln Lys His Ser Ala Asp Lys Ser Cys Asp Leu
    210                 215                 220

Gly Leu Ser Met Pro Ser Lys Leu Ser Ile Lys Asp Asn Gly Asn Thr
225                 230                 235                 240

Val Ala Leu Asp Gly Ala Ile Gly Leu Ser Ser Thr Leu Ala Glu Ile
                245                 250                 255

Phe Leu Leu Glu Tyr Ala Gln Gly Met Pro Gln Ala Ala Trp Gly Asn
            260                 265                 270

Ile His Ser Glu Gln Glu Trp Ala Ser Leu Leu Lys Leu His Asn Val
        275                 280                 285

Gln Phe Asp Leu Met Ala Arg Thr Pro Tyr Ile Ala Arg His Asn Gly
    290                 295                 300

Thr Pro Leu Leu Gln Ala Ile Ser Asn Ala Leu Asn Pro Asn Ala Thr
305                 310                 315                 320

Glu Ser Lys Leu Pro Asp Ile Ser Pro Asp Asn Lys Ile Leu Phe Ile
                325                 330                 335
```

```
Ala Gly His Asp Thr Asn Ile Ala Asn Ile Ala Gly Met Leu Asn Met
            340                 345                 350

Arg Trp Thr Leu Pro Gly Gln Pro Asp Asn Thr Pro Pro Gly Gly Ala
        355                 360                 365

Leu Val Phe Glu Arg Leu Ala Asp Lys Ser Gly Lys Gln Tyr Val Ser
    370                 375                 380

Val Ser Met Val Tyr Gln Thr Leu Glu Gln Leu Arg Ser Gln Thr Pro
385                 390                 395                 400

Leu Ser Leu Asn Gln Pro Ala Gly Ser Val Gln Leu Lys Ile Pro Gly
                405                 410                 415

Cys Asn Asp Gln Thr Ala Glu Gly Tyr Cys Pro Leu Ser Thr Phe Thr
            420                 425                 430

Arg Val Val Ser Gln Ser Val Glu Pro Gly Cys Gln Leu Gln
        435                 440                 445

<210> SEQ ID NO 31
<211> LENGTH: 446
<212> TYPE: PRT
<213> ORGANISM: Artificial sequence
<220> FEATURE:
<223> OTHER INFORMATION: Synthetic construct

<400> SEQUENCE: 31

Met Thr Ile Ser Ala Phe Asn Arg Lys Lys Leu Thr Leu His Pro Gly
1               5                   10                  15

Leu Phe Val Ala Leu Ser Ala Ile Phe Ser Leu Gly Ser Thr Ala Tyr
            20                  25                  30

Ala Asn Asp Thr Pro Ala Ser Gly Tyr Gln Val Glu Lys Val Val Ile
            35                  40                  45

Leu Ser Arg His Gly Val Arg Ala Pro Thr Lys Met Thr Gln Thr Met
    50                  55                  60

Arg Asp Val Thr Pro Asn Thr Trp Pro Glu Trp Pro Val Lys Leu Gly
65                  70                  75                  80

Tyr Ile Thr Pro Arg Gly Glu His Leu Ile Ser Leu Met Gly Gly Phe
                85                  90                  95

Tyr Arg Gln Lys Phe Gln Gln Gly Ile Leu Ser Gly Ser Cys
            100                 105                 110

Pro Thr Pro Asn Ser Ile Tyr Val Trp Ala Asp Val Asp Gln Arg Thr
            115                 120                 125

Leu Lys Thr Gly Glu Ala Phe Leu Ala Gly Leu Ala Pro Glu Cys His
    130                 135                 140

Leu Thr Ile His His Gln Gln Asp Ile Lys Lys Ala Asp Pro Leu Phe
145                 150                 155                 160

His Pro Val Lys Ala Gly Ile Cys Ser Met Asp Lys Thr Gln Val Gln
                165                 170                 175

Gln Ala Val Glu Lys Glu Ala Gln Thr Pro Ile Asp Asn Leu Asn Gln
            180                 185                 190

His Tyr Ile Pro Phe Leu Ala Leu Met Asn Thr Thr Leu Asn Phe Ser
        195                 200                 205

Thr Ser Ala Trp Cys Gln Lys His Ser Ala Asp Lys Ser Cys Asp Leu
    210                 215                 220

Gly Leu Ser Met Pro Ser Lys Leu Ser Ile Lys Asp Asn Gly Asn Lys
225                 230                 235                 240

Val Ala Leu Asp Gly Ala Ile Gly Leu Ser Ser Thr Leu Ala Glu Ile
                245                 250                 255
```

```
Phe Leu Leu Glu Tyr Ala Gln Gly Met Pro Gln Ala Ala Trp Gly Asn
                260                 265                 270

Ile His Ser Glu Gln Glu Trp Ala Ser Leu Leu Lys Leu His Asn Val
            275                 280                 285

Gln Phe Asp Leu Met Ala Arg Thr Pro Tyr Ile Ala Arg His Asn Gly
        290                 295                 300

Thr Pro Leu Leu Gln Ala Ile Ser Asn Ala Leu Asn Pro Asn Ala Thr
305                 310                 315                 320

Glu Ser Lys Leu Pro Asp Ile Ser Pro Asp Asn Lys Ile Leu Phe Ile
                325                 330                 335

Ala Gly His Asp Thr Asn Ile Ala Asn Ile Ala Gly Met Leu Asn Met
            340                 345                 350

Arg Trp Thr Leu Pro Gly Gln Pro Asp Asn Thr Pro Pro Gly Gly Ala
        355                 360                 365

Leu Val Phe Glu Arg Leu Ala Asp Lys Ser Gly Lys Gln Tyr Val Ser
370                 375                 380

Val Ser Met Val Tyr Gln Thr Leu Glu Gln Leu Arg Ser Gln Thr Pro
385                 390                 395                 400

Leu Ser Leu Asn Gln Pro Ala Gly Ser Val Gln Leu Lys Ile Pro Gly
                405                 410                 415

Cys Asn Asp Gln Thr Ala Glu Gly Tyr Cys Pro Leu Ser Thr Phe Thr
            420                 425                 430

Arg Val Val Ser Gln Ser Val Glu Pro Gly Cys Gln Leu Gln
        435                 440                 445

<210> SEQ ID NO 32
<211> LENGTH: 446
<212> TYPE: PRT
<213> ORGANISM: Artificial sequence
<220> FEATURE:
<223> OTHER INFORMATION: Synthetic construct

<400> SEQUENCE: 32

Met Thr Ile Ser Ala Phe Asn Arg Lys Lys Leu Thr Leu His Pro Gly
1               5                   10                  15

Leu Phe Val Ala Leu Ser Ala Ile Phe Ser Leu Gly Ser Thr Ala Tyr
            20                  25                  30

Ala Asn Asp Thr Pro Ala Ser Gly Tyr Gln Val Glu Lys Val Val Ile
        35                  40                  45

Leu Ser Arg His Gly Val Arg Ala Pro Thr Lys Met Thr Gln Thr Met
50                  55                  60

Arg Asp Val Thr Pro Asn Thr Trp Pro Glu Trp Pro Val Lys Leu Gly
65                  70                  75                  80

Tyr Ile Thr Pro Arg Gly Glu His Leu Ile Ser Leu Met Gly Gly Phe
                85                  90                  95

Tyr Arg Gln Lys Phe Gln Gln Gln Gly Ile Leu Ser Gln Gly Ser Cys
            100                 105                 110

Pro Thr Pro Asn Ser Ile Tyr Val Trp Ala Asp Val Asp Gln Arg Thr
        115                 120                 125

Leu Lys Thr Gly Glu Ala Phe Leu Ala Gly Leu Ala Pro Glu Cys His
130                 135                 140

Leu Thr Ile His His Gln Gln Asp Ile Lys Lys Ala Asp Pro Leu Phe
145                 150                 155                 160

His Pro Val Lys Ala Gly Thr Cys Ser Met Asp Lys Thr Gln Val Gln
                165                 170                 175
```

```
Gln Ala Val Glu Lys Glu Ala Gln Thr Pro Ile Asp Asn Leu Asn Gln
            180                 185                 190

His Tyr Ile Pro Phe Leu Ala Leu Met Asn Thr Thr Leu Asn Phe Ser
        195                 200                 205

Thr Ser Ala Trp Cys Gln Lys His Ser Ala Asp Lys Ser Cys Asp Leu
    210                 215                 220

Gly Leu Ser Met Pro Ser Lys Leu Ser Ile Lys Asp Asn Gly Asn Glu
225                 230                 235                 240

Val Ala Leu Asp Gly Ala Ile Gly Leu Ser Ser Thr Leu Ala Glu Ile
                245                 250                 255

Phe Leu Leu Glu Tyr Ala Gln Gly Met Pro Gln Ala Ala Trp Gly Asn
                260                 265                 270

Ile His Ser Glu Gln Glu Trp Ala Ser Leu Leu Lys Leu His Asn Val
            275                 280                 285

Gln Phe Asp Leu Met Ala Arg Thr Pro Tyr Ile Ala Arg His Asn Gly
        290                 295                 300

Thr Pro Leu Leu Gln Ala Ile Ser Asn Ala Leu Asn Pro Asn Ala Thr
305                 310                 315                 320

Glu Ser Lys Leu Pro Asp Ile Ser Pro Asp Asn Lys Ile Leu Phe Ile
                325                 330                 335

Ala Gly His Asp Thr Asn Ile Ala Asn Ile Ala Gly Met Leu Asn Met
                340                 345                 350

Arg Trp Thr Leu Pro Gly Gln Pro Asp Asn Thr Pro Pro Gly Gly Ala
            355                 360                 365

Leu Val Phe Glu Arg Leu Ala Asp Lys Ser Gly Lys Gln Tyr Val Ser
        370                 375                 380

Val Ser Met Val Tyr Gln Thr Leu Glu Gln Leu Arg Ser Gln Thr Pro
385                 390                 395                 400

Leu Ser Leu Asn Gln Pro Ala Gly Ser Val Gln Leu Lys Ile Pro Gly
                405                 410                 415

Cys Asn Asp Gln Thr Ala Glu Gly Tyr Cys Pro Leu Ser Thr Phe Thr
                420                 425                 430

Arg Val Val Ser Gln Ser Val Glu Pro Gly Cys Gln Leu Gln
            435                 440                 445

<210> SEQ ID NO 33
<211> LENGTH: 446
<212> TYPE: PRT
<213> ORGANISM: Artificial sequence
<220> FEATURE:
<223> OTHER INFORMATION: Synthetic construct

<400> SEQUENCE: 33

Met Thr Ile Ser Ala Phe Asn Arg Lys Lys Leu Thr Leu His Pro Gly
1               5                   10                  15

Leu Phe Val Ala Leu Ser Ala Ile Phe Ser Leu Gly Ser Thr Ala Tyr
                20                  25                  30

Ala Asn Asp Thr Pro Ala Ser Gly Tyr Gln Val Glu Lys Val Val Ile
            35                  40                  45

Leu Ser Arg His Gly Val Arg Ala Pro Thr Lys Met Thr Gln Thr Met
        50                  55                  60

Arg Asp Val Thr Pro Asn Thr Trp Pro Glu Trp Pro Val Lys Leu Gly
65                  70                  75                  80

Tyr Ile Thr Pro Arg Gly Glu His Leu Ile Ser Leu Met Gly Gly Phe
                85                  90                  95
```

```
Tyr Arg Gln Lys Phe Gln Gln Gln Gly Ile Leu Ser Gln Gly Ser Cys
                100                 105                 110

Pro Thr Pro Asn Ser Ile Tyr Val Trp Ala Asp Val Asp Gln Arg Thr
            115                 120                 125

Leu Lys Thr Gly Glu Ala Phe Leu Ala Gly Leu Ala Pro Glu Cys His
        130                 135                 140

Leu Thr Ile His His Gln Gln Asp Ile Lys Lys Ala Asp Pro Leu Phe
145                 150                 155                 160

His Pro Val Lys Ala Gly Thr Cys Ser Met Asp Lys Thr Gln Val Gln
                165                 170                 175

Gln Ala Val Glu Lys Glu Ala Gln Thr Pro Ile Asp Asn Leu Asn Gln
            180                 185                 190

His Tyr Ile Pro Phe Leu Ala Leu Met Asn Thr Thr Leu Asn Phe Ser
        195                 200                 205

Thr Ser Ala Trp Cys Gln Lys His Ser Ala Asp Lys Ser Cys Asp Leu
210                 215                 220

Gly Leu Ser Met Pro Ser Lys Leu Ser Ile Lys Asp Asn Gly Asn Lys
225                 230                 235                 240

Val Ala Leu Cys Gly Ala Ile Gly Leu Ser Ser Thr Leu Ala Glu Ile
                245                 250                 255

Phe Leu Leu Glu Tyr Ala Gln Gly Met Pro Gln Ala Ala Trp Gly Asn
            260                 265                 270

Ile His Ser Glu Gln Glu Trp Ala Ser Leu Leu Lys Leu His Asn Val
        275                 280                 285

Gln Phe Asp Leu Met Ala Arg Thr Pro Tyr Ile Ala Arg His Asn Gly
        290                 295                 300

Thr Pro Leu Leu Gln Ala Ile Ser Asn Ala Leu Asn Pro Asn Ala Thr
305                 310                 315                 320

Glu Ser Lys Leu Pro Asp Ile Ser Pro Asp Asn Lys Ile Leu Phe Ile
                325                 330                 335

Ala Gly His Asp Thr Asn Ile Ala Asn Ile Ala Gly Met Leu Asn Met
            340                 345                 350

Arg Trp Thr Leu Pro Gly Gln Pro Asp Asn Thr Pro Pro Gly Gly Ala
        355                 360                 365

Leu Val Phe Glu Arg Leu Ala Asp Lys Ser Gly Lys Gln Tyr Val Ser
370                 375                 380

Val Ser Met Val Tyr Gln Thr Leu Glu Gln Leu Arg Ser Gln Thr Pro
385                 390                 395                 400

Leu Ser Leu Asn Gln Pro Ala Gly Ser Val Gln Leu Lys Ile Pro Gly
                405                 410                 415

Cys Asn Asp Gln Thr Ala Glu Gly Tyr Cys Pro Leu Ser Thr Phe Thr
            420                 425                 430

Arg Val Val Ser Gln Ser Val Glu Pro Gly Cys Gln Leu Gln
        435                 440                 445
```

<210> SEQ ID NO 34
<211> LENGTH: 446
<212> TYPE: PRT
<213> ORGANISM: Artificial sequence
<220> FEATURE:
<223> OTHER INFORMATION: Synthetic construct

<400> SEQUENCE: 34

```
Met Thr Ile Ser Ala Phe Asn Arg Lys Lys Leu Thr Leu His Pro Gly
1               5                   10                  15
```

```
Leu Phe Val Ala Leu Ser Ala Ile Phe Ser Leu Gly Ser Thr Ala Tyr
             20                  25                  30
Ala Asn Asp Thr Pro Ala Ser Gly Tyr Gln Val Glu Lys Val Val Ile
         35                  40                  45
Leu Ser Arg His Gly Val Arg Ala Pro Thr Lys Met Thr Gln Thr Met
     50                  55                  60
Arg Asp Val Thr Pro Asn Thr Trp Pro Glu Trp Pro Val Lys Leu Gly
 65                  70                  75                  80
Tyr Ile Thr Pro Arg Gly Glu His Leu Ile Ser Leu Met Gly Gly Phe
                 85                  90                  95
Tyr Arg Gln Lys Phe Gln Gln Gln Gly Ile Leu Ser Gln Gly Ser Cys
            100                 105                 110
Pro Thr Pro Asn Ser Ile Tyr Val Trp Ala Asp Val Asp Gln Arg Thr
        115                 120                 125
Leu Lys Thr Gly Glu Ala Phe Leu Ala Gly Leu Ala Pro Glu Cys His
    130                 135                 140
Leu Thr Ile His His Gln Gln Asp Ile Lys Lys Ala Asp Pro Leu Phe
145                 150                 155                 160
His Pro Val Lys Ala Gly Thr Cys Ser Met Asp Lys Thr Gln Val Gln
                165                 170                 175
Gln Ala Val Glu Lys Glu Ala Gln Thr Pro Ile Asp Asn Leu Asn Gln
            180                 185                 190
His Tyr Ile Pro Phe Leu Ala Leu Met Asn Thr Thr Leu Asn Phe Ser
        195                 200                 205
Thr Ser Ala Trp Cys Gln Lys His Ser Ala Asp Lys Ser Cys Asp Leu
    210                 215                 220
Gly Leu Ser Met Pro Ser Lys Leu Ser Ile Lys Asp Asn Gly Asn Lys
225                 230                 235                 240
Val Ala Leu Asp Gly Ala Ile Gly Leu Ser Ser Thr Leu Ala Glu Ile
                245                 250                 255
Phe Leu Leu Glu Tyr Ala Gln Gly Met Pro Gln Ala Ala Trp Gly Asn
            260                 265                 270
Ile His Ser Glu Gln Glu Trp Ala Ser Leu Leu Lys Leu His Asn Val
        275                 280                 285
Tyr Phe Asp Leu Met Ala Arg Thr Pro Tyr Ile Ala Arg His Asn Gly
    290                 295                 300
Thr Pro Leu Leu Gln Ala Ile Ser Asn Ala Leu Asn Pro Asn Ala Thr
305                 310                 315                 320
Glu Ser Lys Leu Pro Asp Ile Ser Pro Asp Asn Lys Ile Leu Phe Ile
                325                 330                 335
Ala Gly His Asp Thr Asn Ile Ala Asn Ile Ala Gly Met Leu Asn Met
            340                 345                 350
Arg Trp Thr Leu Pro Gly Gln Pro Asp Asn Thr Pro Pro Gly Gly Ala
        355                 360                 365
Leu Val Phe Glu Arg Leu Ala Asp Lys Ser Gly Lys Gln Tyr Val Ser
    370                 375                 380
Val Ser Met Val Tyr Gln Thr Leu Glu Gln Leu Arg Ser Gln Thr Pro
385                 390                 395                 400
Leu Ser Leu Asn Gln Pro Ala Gly Ser Val Gln Leu Lys Ile Pro Gly
                405                 410                 415
Cys Asn Asp Gln Thr Ala Glu Gly Tyr Cys Pro Leu Ser Thr Phe Thr
            420                 425                 430
Arg Val Val Ser Gln Ser Val Glu Pro Gly Cys Gln Leu Gln
```

```
                435              440             445

<210> SEQ ID NO 35
<211> LENGTH: 446
<212> TYPE: PRT
<213> ORGANISM: Artificial sequence
<220> FEATURE:
<223> OTHER INFORMATION: Synthetic construct

<400> SEQUENCE: 35

Met Thr Ile Ser Ala Phe Asn Arg Lys Lys Leu Thr Leu His Pro Gly
1               5                   10                  15

Leu Phe Val Ala Leu Ser Ala Ile Phe Ser Leu Gly Ser Thr Ala Tyr
            20                  25                  30

Ala Asn Asp Thr Pro Ala Ser Gly Tyr Gln Val Glu Lys Val Val Ile
        35                  40                  45

Leu Ser Arg His Gly Val Arg Ala Pro Thr Lys Met Thr Gln Thr Met
    50                  55                  60

Arg Asp Val Thr Pro Asn Thr Trp Pro Glu Trp Pro Val Lys Leu Gly
65                  70                  75                  80

Tyr Ile Thr Pro Arg Gly Glu His Leu Ile Ser Leu Met Gly Gly Phe
                85                  90                  95

Tyr Arg Gln Lys Phe Gln Gln Gln Gly Ile Leu Ser Gln Gly Ser Cys
            100                 105                 110

Pro Thr Pro Asn Ser Ile Tyr Val Trp Ala Asp Val Asp Gln Arg Thr
        115                 120                 125

Leu Lys Thr Gly Glu Ala Phe Leu Ala Gly Leu Ala Pro Glu Cys His
    130                 135                 140

Leu Thr Ile His His Gln Gln Asp Ile Lys Lys Ala Asp Pro Leu Phe
145                 150                 155                 160

His Pro Val Lys Ala Gly Thr Cys Ser Met Asp Lys Thr Gln Val Gln
                165                 170                 175

Gln Ala Val Glu Lys Glu Ala Gln Thr Pro Ile Asp Asn Leu Asn Gln
            180                 185                 190

His Tyr Ile Pro Phe Leu Ala Leu Met Asn Thr Thr Leu Asn Phe Ser
        195                 200                 205

Lys Ser Ala Trp Cys Gln Lys His Ser Ala Asp Lys Ser Cys Asp Leu
    210                 215                 220

Gly Leu Ser Met Pro Ser Lys Leu Ser Ile Lys Asp Asn Gly Asn Lys
225                 230                 235                 240

Val Ala Leu Asp Gly Ala Ile Gly Leu Ser Ser Thr Leu Ala Glu Ile
                245                 250                 255

Phe Leu Leu Glu Tyr Ala Gln Gly Met Pro Gln Ala Ala Trp Gly Asn
            260                 265                 270

Ile His Ser Glu Gln Glu Trp Ala Ser Leu Leu Lys Leu His Asn Val
        275                 280                 285

Gln Phe Asp Leu Met Ala Arg Thr Pro Tyr Ile Ala Arg His Asn Gly
    290                 295                 300

Thr Pro Leu Leu Gln Ala Ile Ser Asn Ala Leu Asn Pro Asn Ala Thr
305                 310                 315                 320

Glu Ser Lys Leu Pro Asp Ile Ser Pro Asp Asn Lys Ile Leu Phe Ile
                325                 330                 335

Ala Gly His Asp Thr Asn Ile Ala Asn Ile Ala Gly Met Leu Asn Met
            340                 345                 350

Arg Trp Thr Leu Pro Gly Gln Pro Asp Asn Thr Pro Pro Gly Gly Ala
```

```
            355                 360                 365
Leu Val Phe Glu Arg Leu Ala Asp Lys Ser Gly Lys Gln Tyr Val Ser
            370                 375                 380

Val Ser Met Val Tyr Gln Thr Leu Glu Gln Leu Arg Ser Gln Thr Pro
385                 390                 395                 400

Leu Ser Leu Asn Gln Pro Ala Gly Ser Val Gln Leu Lys Ile Pro Gly
            405                 410                 415

Cys Asn Asp Gln Thr Ala Glu Gly Tyr Cys Pro Leu Ser Thr Phe Thr
            420                 425                 430

Arg Val Val Ser Gln Ser Val Glu Pro Gly Cys Gln Leu Gln
            435                 440                 445

<210> SEQ ID NO 36
<211> LENGTH: 446
<212> TYPE: PRT
<213> ORGANISM: Artificial sequence
<220> FEATURE:
<223> OTHER INFORMATION: Synthetic construct

<400> SEQUENCE: 36

Met Thr Ile Ser Ala Phe Asn Arg Lys Lys Leu Thr Leu His Pro Gly
1               5                   10                  15

Leu Phe Val Ala Leu Ser Ala Ile Phe Ser Leu Gly Ser Thr Ala Tyr
            20                  25                  30

Ala Asn Asp Thr Pro Ala Ser Gly Tyr Gln Val Glu Lys Val Val Ile
            35                  40                  45

Leu Ser Arg His Gly Val Arg Ala Pro Thr Lys Met Thr Gln Thr Met
50                  55                  60

Arg Asp Val Thr Pro Asn Thr Trp Pro Glu Trp Pro Val Lys Leu Gly
65                  70                  75                  80

Tyr Ile Thr Pro Arg Gly Glu His Leu Ile Ser Leu Met Gly Gly Phe
            85                  90                  95

Tyr Arg Gln Lys Phe Gln Gln Gly Ile Leu Ser Gln Gly Ser Cys
            100                 105                 110

Pro Thr Pro Asn Ser Ile Tyr Val Trp Ala Asp Val Asp Gln Arg Thr
            115                 120                 125

Leu Lys Thr Gly Glu Ala Phe Leu Ala Gly Leu Ala Pro Glu Cys His
            130                 135                 140

Leu Thr Ile His His Gln Gln Asp Ile Lys Lys Ala Asp Pro Leu Phe
145                 150                 155                 160

His Pro Val Lys Ala Gly Thr Cys Ser Met Asp Lys Thr Gln Val Gln
                165                 170                 175

Gln Ala Val Glu Lys Glu Ala Gln Thr Pro Ile Asp Asn Leu Asn Gln
            180                 185                 190

His Tyr Ile Pro Ser Leu Ala Leu Met Asn Thr Thr Leu Asn Phe Ser
            195                 200                 205

Thr Ser Ala Trp Cys Gln Lys His Ser Ala Asp Lys Ser Cys Asp Leu
            210                 215                 220

Gly Leu Ser Met Pro Ser Lys Leu Ser Ile Lys Asp Asn Gly Asn Lys
225                 230                 235                 240

Val Ala Leu Asp Gly Ala Ile Gly Leu Ser Ser Thr Leu Ala Glu Ile
                245                 250                 255

Phe Leu Leu Glu Tyr Ala Gln Gly Met Pro Gln Ala Ala Trp Gly Asn
            260                 265                 270

Ile His Ser Glu Gln Glu Trp Ala Ser Leu Leu Lys Leu His Asn Val
```

```
                    275                 280                 285
        Gln Phe Asp Leu Met Ala Arg Thr Pro Tyr Ile Ala Arg His Asn Gly
        290                 295                 300

Thr Pro Leu Leu Gln Ala Ile Ser Asn Ala Leu Asn Pro Asn Ala Thr
        305                 310                 315                 320

Glu Ser Lys Leu Pro Asp Ile Ser Pro Asp Asn Lys Ile Leu Phe Ile
                        325                 330                 335

Ala Gly His Asp Thr Asn Ile Ala Asn Ile Ala Gly Met Leu Asn Met
                        340                 345                 350

Arg Trp Thr Leu Pro Gly Gln Pro Asp Asn Thr Pro Pro Gly Gly Ala
                        355                 360                 365

Leu Val Phe Glu Arg Leu Ala Asp Lys Ser Gly Lys Gln Tyr Val Ser
                        370                 375                 380

Val Ser Met Val Tyr Gln Thr Leu Glu Gln Leu Arg Ser Gln Thr Pro
        385                 390                 395                 400

Leu Ser Leu Asn Gln Pro Ala Gly Ser Val Gln Leu Lys Ile Pro Gly
                        405                 410                 415

Cys Asn Asp Gln Thr Ala Glu Gly Tyr Cys Pro Leu Ser Thr Phe Thr
                        420                 425                 430

Arg Val Val Ser Gln Ser Val Glu Pro Gly Cys Gln Leu Gln
                        435                 440                 445

<210> SEQ ID NO 37
<211> LENGTH: 446
<212> TYPE: PRT
<213> ORGANISM: Artificial sequence
<220> FEATURE:
<223> OTHER INFORMATION: Synthetic construct

<400> SEQUENCE: 37

Met Thr Ile Ser Ala Phe Asn Arg Lys Lys Leu Thr Leu His Pro Gly
1               5                   10                  15

Leu Phe Val Ala Leu Ser Ala Ile Phe Ser Leu Gly Ser Thr Ala Tyr
                20                  25                  30

Ala Asn Asp Thr Pro Ala Ser Gly Tyr Gln Val Glu Lys Val Val Ile
                35                  40                  45

Leu Ser Arg His Gly Val Arg Ala Pro Thr Lys Met Thr Gln Thr Met
        50                  55                  60

Arg Asp Val Thr Pro Asn Thr Trp Pro Glu Trp Pro Val Lys Leu Gly
65                  70                  75                  80

Tyr Ile Thr Pro Arg Gly Glu His Leu Ile Ser Leu Met Gly Gly Phe
                85                  90                  95

Tyr Arg Gln Lys Phe Gln Gln Gln Gly Ile Leu Ser Gln Gly Ser Cys
                100                 105                 110

Pro Thr Pro Asn Ser Ile Tyr Val Trp Ala Asp Val Glu Gln Arg Thr
            115                 120                 125

Leu Lys Thr Gly Glu Ala Phe Leu Ala Gly Leu Ala Pro Glu Cys His
        130                 135                 140

Leu Thr Ile His His Gln Gln Asp Ile Lys Lys Ala Asp Pro Leu Phe
145                 150                 155                 160

His Pro Val Lys Ala Gly Thr Cys Ser Met Asp Lys Thr Gln Val Gln
                165                 170                 175

Gln Ala Val Glu Lys Glu Ala Gln Thr Pro Ile Asp Asn Leu Asn Gln
                180                 185                 190

Arg Tyr Ile Pro Phe Leu Ala Leu Met Asn Thr Thr Leu Asn Phe Ser
```

```
            195                 200                 205
Thr Ser Ala Trp Cys Gln Lys His Ser Ala Asp Lys Ser Cys Asp Leu
        210                 215                 220

Gly Leu Ser Met Pro Ser Lys Leu Ser Ile Lys Asp Asn Gly Asn Lys
225                 230                 235                 240

Val Ala Leu Asp Gly Ala Ile Gly Leu Ser Ser Thr Leu Ala Glu Ile
                245                 250                 255

Phe Leu Leu Glu Tyr Ala Gln Gly Met Pro Gln Ala Ala Trp Gly Asn
                260                 265                 270

Ile His Ser Glu Gln Glu Trp Ala Ser Leu Leu Lys Leu His Asn Val
            275                 280                 285

Gln Phe Asp Leu Met Ala Arg Thr Pro Tyr Ile Ala Arg His Asn Gly
        290                 295                 300

Thr Pro Leu Leu Gln Ala Ile Ser Asn Ala Leu Asn Pro Asn Ala Thr
305                 310                 315                 320

Glu Ser Lys Leu Pro Asp Ile Ser Pro Asp Asn Lys Ile Leu Phe Ile
                325                 330                 335

Ala Gly His Asp Thr Asn Ile Ala Asn Ile Ala Gly Met Leu Asn Met
                340                 345                 350

Arg Trp Thr Leu Pro Gly Gln Pro Asp Asn Thr Pro Pro Gly Gly Ala
            355                 360                 365

Leu Val Phe Glu Arg Leu Ala Asp Lys Ser Gly Lys Gln Tyr Val Ser
        370                 375                 380

Val Ser Met Val Tyr Gln Thr Leu Glu Gln Leu Arg Ser Gln Thr Pro
385                 390                 395                 400

Leu Ser Leu Asn Gln Pro Ala Gly Ser Val Gln Leu Lys Ile Pro Gly
                405                 410                 415

Cys Asn Asp Gln Thr Ala Glu Gly Tyr Cys Pro Leu Ser Thr Phe Thr
                420                 425                 430

Arg Val Val Ser Gln Ser Val Glu Pro Gly Cys Gln Leu Gln
            435                 440                 445

<210> SEQ ID NO 38
<211> LENGTH: 446
<212> TYPE: PRT
<213> ORGANISM: Artificial sequence
<220> FEATURE:
<223> OTHER INFORMATION: Synthetic construct

<400> SEQUENCE: 38

Met Thr Ile Ser Ala Phe Asn Arg Lys Lys Leu Thr Leu His Pro Gly
1               5                   10                  15

Leu Phe Val Ala Leu Ser Ala Ile Phe Ser Leu Gly Ser Thr Ala Tyr
                20                  25                  30

Ala Asn Asp Thr Pro Ala Ser Gly Tyr Gln Val Glu Lys Val Val Ile
            35                  40                  45

Leu Ser Arg His Gly Val Arg Ala Pro Thr Lys Met Thr Gln Thr Met
        50                  55                  60

Arg Asp Val Thr Pro Asn Thr Trp Pro Glu Trp Pro Val Lys Leu Gly
65                  70                  75                  80

Tyr Ile Thr Pro Arg Gly Glu His Leu Ile Ser Leu Met Gly Gly Phe
                85                  90                  95

Tyr Arg Gln Lys Phe Gln Gln Gln Gly Ile Leu Ser Gln Gly Ser Cys
                100                 105                 110

Pro Thr Pro Asn Ser Ile Tyr Val Trp Ala Asp Val Asp Gln Arg Thr
```

```
            115                 120                 125
Leu Lys Thr Gly Glu Ala Phe Leu Ala Gly Leu Ala Pro Glu Cys His
    130                 135                 140

Leu Thr Ile His His Gln Gln Asp Ile Lys Lys Ala Asp Pro Leu Phe
145                 150                 155                 160

His Pro Val Lys Ala Gly Thr Cys Ser Met Asp Lys Thr Gln Val Gln
                165                 170                 175

Gln Ala Val Glu Lys Glu Ala Gln Thr Pro Ile Asp Asn Leu Asn Gln
            180                 185                 190

His Tyr Ile Pro Phe Leu Ala Leu Met Asn Thr Thr Leu Asn Phe Ser
        195                 200                 205

Thr Ser Ala Trp Cys Gln Lys His Ser Ala Asp Lys Ser Cys Asp Leu
210                 215                 220

Gly Leu Ser Met Pro Ser Lys Leu Ser Ile Lys Asp Asn Gly Asn Lys
225                 230                 235                 240

Val Ala Leu Asp Gly Ala Ile Gly Leu Ser Ser Thr Leu Ala Glu Ile
                245                 250                 255

Phe Leu Leu Glu Tyr Ala Gln Gly Met Pro Gln Ala Ala Trp Gly Asn
            260                 265                 270

Ile His Ser Glu Gln Glu Trp Ala Ser Leu Leu Lys Leu His Asn Val
        275                 280                 285

Gln Phe Asp Leu Met Glu Arg Thr Pro Tyr Ile Ala Arg His Lys Gly
    290                 295                 300

Thr Pro Leu Leu Gln Ala Ile Ser Asn Ala Leu Asn Pro Asn Ala Thr
305                 310                 315                 320

Glu Ser Lys Leu Pro Asp Ile Ser Pro Asp Asn Lys Ile Leu Phe Ile
                325                 330                 335

Ala Gly His Asp Thr Asn Ile Ala Asn Ile Ala Gly Met Leu Asn Met
            340                 345                 350

Arg Trp Thr Leu Pro Gly Gln Pro Asp Asn Thr Pro Gly Gly Ala
        355                 360                 365

Leu Val Phe Glu Arg Leu Ala Asp Lys Ser Gly Lys Gln Tyr Val Ser
370                 375                 380

Val Ser Met Val Tyr Gln Thr Leu Glu Gln Leu Arg Ser Gln Thr Pro
385                 390                 395                 400

Leu Ser Leu Asn Gln Pro Ala Gly Ser Val Gln Leu Lys Ile Pro Gly
                405                 410                 415

Cys Asn Asp Gln Thr Ala Glu Gly Tyr Cys Pro Leu Ser Thr Phe Thr
            420                 425                 430

Arg Val Val Ser Gln Ser Val Glu Pro Gly Cys Gln Leu Gln
        435                 440                 445
```

<210> SEQ ID NO 39
<211> LENGTH: 446
<212> TYPE: PRT
<213> ORGANISM: Artificial sequence
<220> FEATURE:
<223> OTHER INFORMATION: Synthetic construct

<400> SEQUENCE: 39

```
Met Thr Ile Ser Ala Phe Asn Arg Lys Lys Leu Thr Leu His Pro Gly
1               5                   10                  15

Leu Phe Val Ala Leu Ser Ala Ile Phe Ser Leu Gly Ser Thr Ala Tyr
                20                  25                  30

Ala Asn Asp Thr Pro Ala Ser Gly Tyr Gln Val Glu Lys Val Val Ile
```

```
            35                  40                  45
Leu Ser Arg His Gly Val Arg Ala Pro Thr Lys Met Thr Gln Thr Met
 50                  55                  60

Arg Asp Val Thr Pro Asn Thr Trp Pro Glu Trp Pro Val Lys Leu Gly
 65                  70                  75                  80

Tyr Ile Thr Pro Arg Gly Glu His Leu Ile Ser Leu Met Gly Gly Phe
                 85                  90                  95

Tyr Arg Gln Lys Phe Gln Gln Gly Ile Leu Ser Gly Ser Cys
            100                 105                 110

Pro Thr Pro Asn Ser Ile Tyr Val Trp Ala Asp Val Asp Gln Arg Thr
            115                 120                 125

Leu Lys Thr Gly Glu Ala Phe Leu Ala Gly Leu Ala Pro Glu Cys His
130                 135                 140

Leu Thr Ile His His Gln Gln Asp Ile Lys Lys Ala Asp Pro Leu Phe
145                 150                 155                 160

His Pro Val Lys Ala Gly Ile Cys Ser Met Asp Lys Thr Gln Val Gln
                165                 170                 175

Gln Ala Val Glu Lys Glu Ala Gln Thr Pro Ile Asp Asn Leu Asn Gln
            180                 185                 190

His Tyr Ile Pro Phe Leu Ala Leu Met Asn Thr Thr Leu Asn Phe Ser
        195                 200                 205

Thr Ser Ala Trp Cys Gln Lys His Ser Ala Asp Lys Ser Cys Asp Leu
210                 215                 220

Gly Leu Ser Met Pro Ser Lys Leu Ser Ile Lys Asp Asn Gly Asn Thr
225                 230                 235                 240

Val Ala Leu Asp Gly Ala Ile Gly Leu Ser Ser Thr Leu Ala Glu Ile
                245                 250                 255

Phe Leu Leu Glu Tyr Ala Gln Gly Met Pro Gln Ala Ala Trp Gly Asn
            260                 265                 270

Ile His Ser Glu Gln Glu Trp Ala Ser Leu Leu Lys Leu His Asn Val
        275                 280                 285

Gln Phe Asp Leu Met Ala Arg Thr Pro Tyr Ile Ala Arg His Asn Gly
290                 295                 300

Thr Pro Leu Leu Gln Ala Ile Ser Asn Ala Leu Asn Pro Asn Ala Thr
305                 310                 315                 320

Glu Ser Lys Leu Pro Asp Ile Ser Pro Asp Asn Lys Ile Leu Phe Ile
                325                 330                 335

Ala Gly His Asp Thr Asn Ile Ala Asn Ile Ala Gly Met Leu Asn Met
            340                 345                 350

Arg Trp Thr Leu Pro Gly Gln Pro Asp Asn Thr Pro Pro Gly Gly Ala
        355                 360                 365

Leu Val Phe Glu Arg Leu Ala Asp Lys Ser Gly Lys Gln Tyr Val Ser
370                 375                 380

Val Ser Met Val Tyr Gln Thr Leu Glu Gln Leu Arg Ser Gln Thr Pro
385                 390                 395                 400

Leu Ser Leu Asn Gln Pro Ala Gly Ser Val Gln Leu Lys Ile Pro Gly
                405                 410                 415

Cys Asn Asp Gln Thr Ala Glu Gly Tyr Cys Pro Leu Ser Thr Phe Thr
            420                 425                 430

Arg Val Val Ser Gln Ser Val Glu Pro Gly Cys Gln Leu Gln
        435                 440                 445

<210> SEQ ID NO 40
```

<211> LENGTH: 446
<212> TYPE: PRT
<213> ORGANISM: Artificial sequence
<220> FEATURE:
<223> OTHER INFORMATION: Synthetic construct

<400> SEQUENCE: 40

| | | | | | | | | | | | | | | |
|---|---|---|---|---|---|---|---|---|---|---|---|---|---|---|
| Met | Thr | Ile | Ser | Ala | Phe | Asn | Arg | Lys | Lys | Leu | Thr | Leu | His | Pro | Gly |
| 1 | | | | 5 | | | | | 10 | | | | | 15 | |
| Leu | Phe | Val | Ala | Leu | Ser | Ala | Ile | Phe | Ser | Leu | Gly | Ser | Thr | Ala | Tyr |
| | | | 20 | | | | | 25 | | | | | 30 | | |
| Ala | Asn | Asp | Thr | Pro | Ala | Ser | Gly | Tyr | Gln | Val | Glu | Lys | Val | Val | Ile |
| | | 35 | | | | | 40 | | | | | 45 | | | |
| Leu | Ser | Arg | His | Gly | Val | Arg | Ala | Pro | Thr | Lys | Met | Thr | Gln | Thr | Met |
| 50 | | | | | 55 | | | | | 60 | | | | | |
| Arg | Asp | Val | Thr | Pro | Asn | Thr | Trp | Pro | Glu | Trp | Pro | Val | Lys | Leu | Gly |
| 65 | | | | | 70 | | | | | 75 | | | | | 80 |
| Tyr | Ile | Thr | Pro | Arg | Gly | Glu | His | Leu | Ile | Ser | Leu | Met | Gly | Gly | Phe |
| | | | | 85 | | | | | 90 | | | | | 95 | |
| Tyr | Arg | Gln | Lys | Phe | Gln | Gln | Gln | Gly | Ile | Leu | Ser | Gln | Gly | Ser | Cys |
| | | | | 100 | | | | | 105 | | | | | 110 | |
| Pro | Thr | Pro | Asn | Ser | Ile | Tyr | Val | Trp | Ala | Asp | Val | Asp | Gln | Arg | Thr |
| | | | 115 | | | | | 120 | | | | | 125 | | |
| Leu | Lys | Thr | Gly | Glu | Ala | Phe | Leu | Ala | Gly | Leu | Ala | Pro | Glu | Cys | His |
| | | 130 | | | | | 135 | | | | | 140 | | | |
| Leu | Thr | Ile | His | His | Gln | Gln | Asp | Ile | Lys | Lys | Ala | Asp | Pro | Leu | Phe |
| 145 | | | | | 150 | | | | | 155 | | | | | 160 |
| His | Pro | Val | Lys | Ala | Gly | Thr | Cys | Ser | Met | Asp | Lys | Thr | Gln | Val | Gln |
| | | | | 165 | | | | | 170 | | | | | 175 | |
| Gln | Ala | Val | Glu | Lys | Glu | Ala | Gln | Thr | Pro | Ile | Asp | Asn | Leu | Asn | Gln |
| | | | | 180 | | | | | 185 | | | | | 190 | |
| His | Tyr | Ile | Pro | Phe | Leu | Ala | Leu | Met | Asn | Thr | Thr | Leu | Asn | Phe | Ser |
| | | | 195 | | | | | 200 | | | | | 205 | | |
| Thr | Ser | Ala | Trp | Cys | Gln | Lys | His | Ser | Ala | Asp | Lys | Ser | Cys | Glu | Leu |
| | | 210 | | | | | 215 | | | | | 220 | | | |
| Gly | Leu | Ser | Met | Pro | Ser | Lys | Leu | Ser | Ile | Lys | Asp | Asn | Gly | Asn | Glu |
| 225 | | | | | 230 | | | | | 235 | | | | | 240 |
| Val | Ala | Leu | Asp | Gly | Ala | Ile | Gly | Leu | Ser | Ser | Thr | Leu | Ala | Glu | Ile |
| | | | | 245 | | | | | 250 | | | | | 255 | |
| Phe | Leu | Leu | Glu | Tyr | Ala | Gln | Gly | Met | Pro | Gln | Ala | Ala | Trp | Gly | Asn |
| | | | | 260 | | | | | 265 | | | | | 270 | |
| Ile | His | Ser | Glu | Gln | Glu | Trp | Ala | Ser | Leu | Leu | Lys | Leu | His | Asn | Val |
| | | | 275 | | | | | 280 | | | | | 285 | | |
| Gln | Phe | Asp | Leu | Met | Ala | Arg | Thr | Pro | Tyr | Ile | Ala | Arg | His | Asn | Gly |
| | | 290 | | | | | 295 | | | | | 300 | | | |
| Thr | Pro | Leu | Leu | Gln | Ala | Ile | Ser | Asn | Ala | Leu | Asn | Pro | Asn | Ala | Thr |
| 305 | | | | | 310 | | | | | 315 | | | | | 320 |
| Glu | Ser | Lys | Leu | Pro | Asp | Ile | Ser | Pro | Asp | Asn | Lys | Ile | Leu | Phe | Ile |
| | | | | 325 | | | | | 330 | | | | | 335 | |
| Ala | Gly | His | Asp | Thr | Asn | Ile | Ala | Asn | Ile | Ala | Gly | Met | Leu | Asp | Met |
| | | | 340 | | | | | 345 | | | | | 350 | | |
| Arg | Trp | Thr | Leu | Pro | Gly | Gln | Pro | Asp | Asn | Thr | Pro | Pro | Gly | Gly | Ala |
| | | 355 | | | | | 360 | | | | | 365 | | | |
| Leu | Val | Phe | Glu | Arg | Leu | Ala | Asp | Lys | Ser | Gly | Lys | Gln | Tyr | Val | Ser |
| | | 370 | | | | | 375 | | | | | 380 | | | |

```
Val Ser Met Val Tyr Gln Thr Leu Glu Gln Leu Arg Ser Gln Thr Pro
385                 390                 395                 400

Leu Ser Leu Asn Gln Pro Ala Gly Ser Val Gln Leu Lys Ile Pro Gly
                405                 410                 415

Cys Asn Asp Gln Thr Ala Glu Gly Tyr Cys Pro Leu Ser Thr Phe Thr
            420                 425                 430

Arg Val Val Ser Gln Ser Val Glu Pro Gly Cys Gln Leu Gln
        435                 440                 445
```

<210> SEQ ID NO 41
<211> LENGTH: 446
<212> TYPE: PRT
<213> ORGANISM: Artificial sequence
<220> FEATURE:
<223> OTHER INFORMATION: Synthetic construct

<400> SEQUENCE: 41

```
Met Thr Ile Ser Ala Phe Asn Arg Lys Lys Leu Thr Leu His Pro Gly
1               5                   10                  15

Leu Phe Val Ala Leu Ser Ala Ile Phe Ser Leu Gly Ser Thr Ala Tyr
                20                  25                  30

Ala Asn Asp Thr Pro Ala Ser Gly Tyr Gln Val Glu Lys Val Val Ile
            35                  40                  45

Leu Ser Arg His Gly Val Arg Ala Pro Thr Lys Met Thr Gln Thr Met
50                  55                  60

Arg Asp Val Thr Pro Asn Thr Trp Pro Glu Trp Pro Val Lys Leu Gly
65                  70                  75                  80

Tyr Ile Thr Pro Arg Gly Glu His Leu Ile Ser Leu Met Gly Gly Phe
                85                  90                  95

Tyr Arg Gln Lys Phe Gln Gln Gly Ile Leu Ser Gln Gly Ser Cys
                100                 105                 110

Pro Thr Pro Asn Ser Ile Tyr Val Trp Ala Asp Val Asp Gln Arg Thr
            115                 120                 125

Leu Lys Thr Gly Glu Ala Phe Leu Ala Gly Leu Ala Pro Glu Cys His
    130                 135                 140

Leu Thr Ile His His Gln Gln Asp Ile Lys Lys Ala Asp Pro Leu Phe
145                 150                 155                 160

His Pro Val Lys Ala Gly Ile Cys Ser Met Asp Lys Thr Gln Val Gln
                165                 170                 175

Gln Ala Val Glu Lys Glu Ala Gln Thr Pro Ile Asp Asn Leu Asn Gln
            180                 185                 190

His Tyr Ile Pro Phe Leu Ala Leu Met Asn Thr Thr Leu Asn Phe Ser
        195                 200                 205

Thr Ser Ala Trp Cys Gln Lys His Ser Ala Asp Lys Ser Cys Asp Leu
    210                 215                 220

Gly Leu Ser Met Pro Ser Lys Leu Ser Ile Lys Asp Asn Gly Asn Thr
225                 230                 235                 240

Val Ala Leu Asp Gly Ala Ile Gly Leu Ser Ser Thr Leu Ala Glu Ile
                245                 250                 255

Phe Leu Leu Glu Tyr Ala Gln Gly Met Pro Gln Ala Ala Trp Gly Asn
            260                 265                 270

Ile His Ser Glu Gln Glu Trp Ala Ser Leu Leu Lys Leu His Asn Val
        275                 280                 285

Gln Phe Asp Leu Met Glu Arg Thr Pro Tyr Ile Ala Arg His Lys Gly
    290                 295                 300
```

```
Thr Pro Leu Leu Gln Ala Ile Ser Asn Ala Leu Asn Pro Asn Ala Thr
305                 310                 315                 320

Glu Ser Lys Leu Pro Asp Ile Ser Pro Asp Asn Lys Ile Leu Phe Ile
            325                 330                 335

Ala Gly His Asp Thr Asn Ile Ala Asn Ile Ala Gly Met Leu Asn Met
            340                 345                 350

Arg Trp Thr Leu Pro Gly Gln Pro Asp Asn Thr Pro Pro Gly Gly Ala
            355                 360                 365

Leu Val Phe Glu Arg Leu Ala Asp Lys Ser Gly Lys Gln Tyr Val Ser
370                 375                 380

Val Ser Met Val Tyr Gln Thr Leu Glu Gln Leu Arg Ser Gln Thr Pro
385                 390                 395                 400

Leu Ser Leu Asn Gln Pro Ala Gly Ser Val Gln Leu Lys Ile Pro Gly
                405                 410                 415

Cys Asn Asp Gln Thr Ala Glu Gly Tyr Cys Pro Leu Ser Thr Phe Thr
            420                 425                 430

Arg Val Val Ser Gln Ser Val Glu Pro Gly Cys Gln Leu Gln
            435                 440                 445

<210> SEQ ID NO 42
<211> LENGTH: 446
<212> TYPE: PRT
<213> ORGANISM: Artificial sequence
<220> FEATURE:
<223> OTHER INFORMATION: Synthetic construct

<400> SEQUENCE: 42

Met Thr Ile Ser Ala Phe Asn Arg Lys Lys Leu Thr Leu His Pro Gly
1               5                   10                  15

Leu Phe Val Ala Leu Ser Ala Ile Phe Ser Leu Gly Ser Thr Ala Tyr
            20                  25                  30

Ala Asn Asp Thr Pro Ala Ser Gly Tyr Gln Val Glu Lys Val Val Ile
        35                  40                  45

Leu Ser Arg His Gly Val Arg Ala Pro Thr Lys Met Thr Gln Thr Met
50                  55                  60

Arg Asp Val Thr Pro Asn Thr Trp Pro Glu Trp Pro Val Lys Leu Gly
65                  70                  75                  80

Tyr Ile Thr Pro Arg Gly Glu His Leu Ile Ser Leu Met Gly Gly Phe
                85                  90                  95

Tyr Arg Gln Lys Phe Gln Gln Gln Gly Ile Leu Ser Gln Gly Ser Cys
            100                 105                 110

Pro Thr Pro Asn Ser Ile Tyr Val Trp Ala Asp Val Asp Gln Arg Thr
        115                 120                 125

Leu Lys Thr Gly Glu Ala Phe Leu Ala Gly Leu Ala Pro Glu Cys His
130                 135                 140

Leu Thr Ile His His Gln Gln Asp Ile Lys Lys Ala Asp Pro Leu Phe
145                 150                 155                 160

His Pro Val Lys Ala Gly Ile Cys Ser Met Asp Lys Thr Gln Val Gln
                165                 170                 175

Gln Ala Val Glu Lys Glu Ala Gln Thr Pro Ile Asp Asn Leu Asn Gln
            180                 185                 190

His Tyr Ile Pro Phe Leu Ala Leu Met Asn Thr Thr Leu Asn Phe Ser
        195                 200                 205

Thr Ser Ala Trp Cys Gln Lys His Ser Ala Asp Lys Ser Cys Asp Leu
210                 215                 220
```

Gly Leu Ser Met Pro Ser Lys Leu Ser Ile Lys Asp Asn Gly Asn Glu
225                 230                 235                 240

Val Ser Leu Asp Gly Ala Ile Gly Leu Ser Ser Thr Leu Ala Glu Ile
            245                 250                 255

Phe Leu Leu Glu Tyr Ala Gln Gly Met Pro Gln Ala Ala Trp Gly Asn
        260                 265                 270

Ile His Ser Glu Gln Glu Trp Ala Ser Leu Leu Lys Leu His Asn Val
        275                 280                 285

Gln Phe Asp Leu Met Glu Arg Thr Pro Tyr Ile Ala Arg His Lys Gly
        290                 295                 300

Thr Pro Leu Leu Gln Ala Ile Ser Asn Ala Leu Asn Pro Asn Ala Thr
305                 310                 315                 320

Glu Ser Lys Leu Pro Asp Ile Ser Pro Asp Asn Lys Ile Leu Phe Ile
                325                 330                 335

Ala Gly His Asp Thr Asn Ile Ala Asn Ile Ala Gly Met Leu Asn Met
                340                 345                 350

Arg Trp Thr Leu Pro Gly Gln Pro Asp Asn Thr Pro Gly Gly Ala
        355                 360                 365

Leu Val Phe Glu Arg Leu Ala Asp Lys Ser Gly Lys Gln Tyr Val Ser
    370                 375                 380

Val Ser Met Val Tyr Gln Thr Leu Glu Gln Leu Arg Ser Gln Thr Pro
385                 390                 395                 400

Leu Ser Leu Asn Gln Pro Ala Gly Ser Val Gln Leu Lys Ile Pro Gly
                405                 410                 415

Cys Asn Asp Gln Thr Ala Glu Gly Tyr Cys Pro Leu Ser Thr Phe Thr
                420                 425                 430

Arg Val Val Ser Gln Ser Val Glu Pro Gly Cys Gln Leu Gln
                435                 440                 445

<210> SEQ ID NO 43
<211> LENGTH: 446
<212> TYPE: PRT
<213> ORGANISM: Artificial sequence
<220> FEATURE:
<223> OTHER INFORMATION: Synthetic construct

<400> SEQUENCE: 43

Met Thr Ile Ser Ala Phe Asn Arg Lys Lys Leu Thr Leu His Pro Gly
1               5                   10                  15

Leu Phe Val Ala Leu Ser Ala Ile Phe Ser Leu Gly Ser Thr Ala Tyr
            20                  25                  30

Ala Asn Asp Thr Pro Ala Ser Gly Tyr Gln Val Glu Lys Val Val Ile
        35                  40                  45

Leu Ser Arg His Gly Val Arg Ala Pro Thr Lys Met Thr Gln Thr Met
    50                  55                  60

Arg Asp Val Thr Pro Asn Thr Trp Pro Glu Trp Pro Val Lys Leu Gly
65                  70                  75                  80

Tyr Ile Thr Pro Arg Gly Glu His Leu Ile Ser Leu Met Gly Gly Phe
                85                  90                  95

Tyr Arg Gln Lys Phe Gln Gln Gln Gly Ile Leu Ser Gln Gly Ser Cys
            100                 105                 110

Pro Thr Pro Asn Ser Ile Tyr Val Trp Thr Asp Val Asp Gln Arg Thr
        115                 120                 125

Leu Lys Thr Gly Glu Ala Phe Leu Ala Gly Leu Ala Pro Glu Cys His
    130                 135                 140

```
Leu Thr Ile His His Gln Gln Asp Ile Lys Lys Ala Asp Pro Leu Phe
145                 150                 155                 160

His Pro Val Lys Ala Gly Ile Cys Ser Met Asp Lys Thr Gln Val Gln
            165                 170                 175

Gln Ala Val Glu Lys Glu Ala Gln Thr Pro Ile Asp Asn Leu Asn Gln
        180                 185                 190

His Tyr Ile Pro Ser Leu Ala Leu Met Asn Thr Thr Leu Asn Phe Ser
    195                 200                 205

Lys Ser Pro Trp Cys Gln Lys His Ser Ala Asp Lys Ser Cys Asp Leu
210                 215                 220

Gly Leu Ser Met Pro Ser Lys Leu Ser Ile Lys Asp Asn Gly Asn Glu
225                 230                 235                 240

Val Ala Leu Asp Gly Ala Ile Gly Leu Ser Ser Thr Leu Ala Glu Ile
            245                 250                 255

Phe Leu Leu Glu Tyr Ala Gln Gly Met Pro Gln Ala Ala Trp Gly Asn
        260                 265                 270

Ile His Ser Glu Gln Glu Trp Ala Ser Leu Leu Lys Leu His Asn Val
    275                 280                 285

Gln Phe Asp Leu Met Glu Arg Thr Pro Tyr Ile Ala Arg His Lys Gly
290                 295                 300

Thr Pro Leu Leu Gln Ala Ile Ser Asn Ala Leu Asn Pro Asn Ala Thr
305                 310                 315                 320

Glu Ser Lys Leu Pro Asp Ile Ser Pro Asp Asn Lys Ile Leu Phe Ile
            325                 330                 335

Ala Gly His Asp Thr Asn Ile Ala Asn Ile Ala Gly Met Leu Asn Met
        340                 345                 350

Arg Trp Thr Leu Pro Gly Gln Pro Asp Asn Thr Pro Gly Gly Ala
    355                 360                 365

Leu Val Phe Glu Arg Leu Ala Asp Lys Ser Gly Lys Gln Tyr Val Ser
370                 375                 380

Val Ser Met Val Tyr Gln Thr Leu Glu Gln Leu Arg Ser Gln Thr Pro
385                 390                 395                 400

Leu Ser Leu Asn Gln Pro Ala Gly Ser Val Gln Leu Lys Ile Pro Gly
            405                 410                 415

Cys Asn Asp Gln Thr Ala Glu Gly Tyr Cys Pro Leu Ser Thr Phe Thr
        420                 425                 430

Arg Val Val Ser Gln Ser Val Glu Pro Gly Cys Gln Leu Gln
    435                 440                 445

<210> SEQ ID NO 44
<211> LENGTH: 446
<212> TYPE: PRT
<213> ORGANISM: Artificial sequence
<220> FEATURE:
<223> OTHER INFORMATION: Synthetic construct

<400> SEQUENCE: 44

Met Thr Ile Ser Ala Phe Asn Arg Lys Lys Leu Thr Leu His Pro Gly
1               5                   10                  15

Leu Phe Val Ala Leu Ser Ala Ile Phe Ser Leu Gly Ser Thr Ala Tyr
            20                  25                  30

Ala Asn Asp Thr Pro Ala Ser Gly Tyr Gln Val Glu Lys Val Val Ile
        35                  40                  45

Leu Ser Arg His Gly Val Arg Ala Pro Thr Lys Met Thr Gln Thr Met
    50                  55                  60
```

Arg Asp Val Thr Pro Asn Thr Trp Pro Glu Trp Pro Val Lys Leu Gly
65                  70                  75                  80

Tyr Ile Thr Pro Arg Gly Glu His Leu Ile Ser Leu Met Gly Gly Phe
            85                  90                  95

Tyr Arg Gln Lys Phe Gln Gln Gln Gly Ile Leu Ser Gln Gly Ser Cys
        100                 105                 110

Pro Thr Pro Asn Ser Ile Tyr Val Trp Thr Asp Val Asp Gln Arg Thr
    115                 120                 125

Leu Lys Thr Gly Glu Ala Phe Leu Ala Gly Leu Ala Pro Glu Cys His
130                 135                 140

Leu Thr Ile His His Gln Gln Asp Ile Lys Lys Ala Asp Pro Leu Phe
145                 150                 155                 160

His Pro Val Lys Ala Gly Ile Cys Ser Met Asp Lys Thr Gln Val Gln
                165                 170                 175

Gln Ala Val Glu Lys Glu Ala Gln Thr Pro Ile Asp Asn Leu Asn Gln
            180                 185                 190

His Tyr Ile Pro Ser Leu Ala Leu Met Asn Thr Thr Leu Asn Phe Ser
        195                 200                 205

Lys Ser Pro Trp Cys Gln Lys His Ser Ala Asp Lys Ser Cys Asp Leu
    210                 215                 220

Gly Leu Ser Met Pro Ser Lys Leu Ser Ile Lys Asp Asn Gly Asn Glu
225                 230                 235                 240

Val Ser Leu Asp Gly Ala Ile Gly Leu Ser Ser Thr Leu Ala Glu Ile
                245                 250                 255

Phe Leu Leu Glu Tyr Ala Gln Gly Met Pro Gln Ala Ala Trp Gly Asn
            260                 265                 270

Ile His Ser Glu Gln Glu Trp Ala Leu Leu Leu Lys Leu His Asn Val
        275                 280                 285

Tyr Phe Asp Leu Met Glu Arg Thr Pro Tyr Ile Ala Arg His Lys Gly
    290                 295                 300

Thr Pro Leu Leu Gln Ala Ile Ser Asn Ala Leu Asn Pro Asn Ala Thr
305                 310                 315                 320

Glu Ser Lys Leu Pro Asp Ile Ser Pro Asp Asn Lys Ile Leu Phe Ile
                325                 330                 335

Ala Gly His Asp Thr Asn Ile Ala Asn Ile Ala Gly Met Leu Asn Met
            340                 345                 350

Arg Trp Thr Leu Pro Gly Gln Pro Asp Asn Thr Pro Pro Gly Gly Ala
        355                 360                 365

Leu Val Phe Glu Arg Leu Ala Asp Lys Ser Gly Lys Gln Tyr Val Ser
    370                 375                 380

Val Ser Met Val Tyr Gln Thr Leu Glu Gln Leu Arg Ser Gln Thr Pro
385                 390                 395                 400

Leu Ser Leu Asn Gln Pro Ala Gly Ser Val Gln Leu Lys Ile Pro Gly
                405                 410                 415

Cys Asn Asp Gln Thr Ala Glu Gly Tyr Cys Pro Leu Ser Thr Phe Thr
            420                 425                 430

Arg Val Val Ser Gln Ser Val Glu Pro Gly Cys Gln Leu Gln
        435                 440                 445

<210> SEQ ID NO 45
<211> LENGTH: 446
<212> TYPE: PRT
<213> ORGANISM: Artificial sequence
<220> FEATURE:

<223> OTHER INFORMATION: Synthetic construct

<400> SEQUENCE: 45

```
Met Thr Ile Ser Ala Phe Asn Arg Lys Lys Leu Thr Leu His Pro Gly
1               5                   10                  15
Leu Phe Val Ala Leu Ser Ala Ile Phe Ser Leu Gly Ser Thr Ala Tyr
            20                  25                  30
Ala Asn Asp Thr Pro Ala Ser Gly Tyr Gln Val Glu Lys Val Val Ile
        35                  40                  45
Leu Ser Arg His Gly Val Arg Ala Pro Thr Lys Met Thr Gln Thr Met
    50                  55                  60
Arg Asp Val Thr Pro Asn Thr Trp Pro Glu Trp Pro Val Lys Leu Gly
65                  70                  75                  80
Tyr Ile Thr Pro Arg Gly Glu His Leu Ile Ser Leu Met Gly Gly Phe
                85                  90                  95
Tyr Arg Gln Lys Phe Gln Gln Gln Gly Ile Leu Ser Gln Gly Ser Cys
            100                 105                 110
Pro Thr Pro Asn Ser Ile Tyr Val Trp Thr Asp Val Glu Gln Arg Thr
        115                 120                 125
Leu Lys Thr Gly Glu Ala Phe Leu Ala Gly Leu Ala Pro Glu Cys His
    130                 135                 140
Leu Thr Ile His His Gln Gln Asp Ile Lys Lys Ala Asp Pro Leu Phe
145                 150                 155                 160
His Pro Val Lys Ala Gly Thr Cys Ser Met Asp Lys Thr Gln Val Gln
                165                 170                 175
Gln Ala Val Glu Lys Glu Ala Gln Thr Pro Ile Asp Asn Leu Asn Gln
            180                 185                 190
Arg Tyr Ile Pro Ser Leu Ala Leu Met Asn Thr Thr Leu Asn Phe Ser
        195                 200                 205
Lys Ser Pro Trp Cys Gln Lys His Ser Ala Asp Lys Asn Cys Asp Leu
    210                 215                 220
Ala Leu Ser Met Pro Ser Lys Leu Ser Ile Lys Asp Asn Gly Asn Glu
225                 230                 235                 240
Val Ala Leu Asp Gly Ala Ile Gly Leu Ser Ser Thr Leu Ala Glu Ile
                245                 250                 255
Phe Leu Leu Glu Tyr Ala Gln Gly Met Pro Gln Ala Ala Trp Gly Asn
            260                 265                 270
Ile His Ser Glu Gln Glu Trp Ala Ser Leu Leu Lys Leu His Asn Val
        275                 280                 285
Gln Phe Asp Leu Met Glu Arg Thr Pro Tyr Ile Ala Arg His Lys Gly
    290                 295                 300
Thr Pro Leu Leu Gln Ala Ile Ser Asn Ala Leu Asn Pro Asn Ala Thr
305                 310                 315                 320
Glu Ser Lys Leu Pro Asp Ile Ser Pro Asp Asn Lys Ile Leu Phe Ile
                325                 330                 335
Ala Gly His Asp Thr Asn Ile Ala Asn Ile Ala Gly Met Leu Asn Met
            340                 345                 350
Arg Trp Thr Leu Pro Gly Gln Pro Asp Asn Thr Pro Pro Gly Gly Ala
        355                 360                 365
Leu Val Phe Glu Arg Leu Ala Asp Lys Ser Gly Lys Gln Tyr Val Ser
    370                 375                 380
Val Ser Met Val Tyr Gln Thr Leu Glu Gln Leu Arg Ser Gln Thr Pro
385                 390                 395                 400
```

Leu Ser Leu Asn Gln Pro Ala Gly Ser Val Gln Leu Lys Ile Pro Gly
                405                 410                 415

Cys Asn Asp Gln Thr Ala Glu Gly Tyr Cys Pro Leu Ser Thr Phe Thr
            420                 425                 430

Arg Val Val Ser Gln Ser Val Glu Pro Gly Cys Gln Leu Gln
        435                 440                 445

<210> SEQ ID NO 46
<211> LENGTH: 446
<212> TYPE: PRT
<213> ORGANISM: Artificial sequence
<220> FEATURE:
<223> OTHER INFORMATION: Synthetic construct

<400> SEQUENCE: 46

Met Thr Ile Ser Ala Phe Asn Arg Lys Lys Leu Thr Leu His Pro Gly
1               5                   10                  15

Leu Phe Val Ala Leu Ser Ala Ile Phe Ser Leu Gly Ser Thr Ala Tyr
            20                  25                  30

Ala Asn Asp Thr Pro Ala Ser Gly Tyr Gln Val Glu Lys Val Val Ile
        35                  40                  45

Leu Ser Arg His Gly Val Arg Ala Pro Thr Lys Met Thr Gln Thr Met
    50                  55                  60

Arg Asp Val Thr Pro Asn Thr Trp Pro Glu Trp Pro Val Lys Leu Gly
65                  70                  75                  80

Tyr Ile Thr Pro Arg Gly Glu His Leu Ile Ser Leu Met Gly Gly Phe
                85                  90                  95

Tyr Arg Gln Lys Phe Gln Gln Gly Ile Leu Ser Gln Gly Ser Cys
            100                 105                 110

Pro Thr Pro Asn Ser Ile Tyr Val Trp Ala Asp Val Glu Gln Arg Thr
        115                 120                 125

Leu Lys Thr Gly Glu Ala Phe Leu Ala Gly Leu Ala Pro Glu Cys His
    130                 135                 140

Leu Thr Ile His His Gln Gln Asp Ile Lys Lys Ala Asp Pro Leu Phe
145                 150                 155                 160

His Pro Val Lys Ala Gly Ile Cys Ser Met Asp Lys Thr Gln Val Gln
                165                 170                 175

Gln Ala Val Glu Lys Glu Ala Gln Thr Pro Ile Asp Asn Leu Asn Gln
            180                 185                 190

Arg Tyr Ile Pro Ser Leu Ala Leu Met Asn Thr Ile Leu Asn Phe Ser
        195                 200                 205

Lys Ser Pro Trp Cys Gln Lys His Ser Ala Asp Lys Ser Cys Asp Leu
    210                 215                 220

Gly Leu Ser Met Pro Ser Lys Leu Ser Ile Lys Asp Asn Gly Asn Glu
225                 230                 235                 240

Val Ala Leu Asp Gly Ala Ile Gly Leu Ser Ser Thr Leu Ala Glu Ile
                245                 250                 255

Phe Leu Leu Glu Tyr Ala Gln Gly Met Pro Gln Val Ala Trp Gly Asn
            260                 265                 270

Ile His Ser Glu Gln Glu Trp Ala Ser Leu Leu Lys Leu His Asn Val
        275                 280                 285

His Phe Asp Leu Met Glu Arg Thr Pro Tyr Ile Ala Arg His Lys Gly
    290                 295                 300

Thr Pro Leu Leu Gln Ala Ile Ser Asn Ala Leu Asn Pro Asn Ala Thr
305                 310                 315                 320

-continued

Glu Ser Lys Leu Pro Asp Ile Ser Pro Asp Asn Lys Ile Leu Phe Ile
            325                 330                 335

Ala Gly His Asp Thr Asn Ile Ala Asn Ile Ala Gly Met Leu Asn Met
            340                 345                 350

Arg Trp Thr Leu Pro Gly Gln Pro Asp Asn Thr Pro Pro Gly Gly Ala
            355                 360                 365

Leu Val Phe Glu Arg Leu Ala Asp Lys Ser Gly Lys Gln Tyr Val Ser
            370                 375                 380

Val Ser Met Val Tyr Gln Thr Leu Glu Gln Leu Arg Ser Gln Thr Pro
385                 390                 395                 400

Leu Ser Leu Asn Gln Pro Ala Gly Ser Val Gln Leu Lys Ile Pro Gly
            405                 410                 415

Cys Asn Asp Gln Thr Ala Glu Gly Tyr Cys Pro Leu Ser Thr Phe Thr
            420                 425                 430

Arg Val Val Ser Gln Ser Val Glu Pro Gly Cys Gln Leu Gln
            435                 440                 445

<210> SEQ ID NO 47
<211> LENGTH: 446
<212> TYPE: PRT
<213> ORGANISM: Artificial sequence
<220> FEATURE:
<223> OTHER INFORMATION: Synthetic construct

<400> SEQUENCE: 47

Met Thr Ile Ser Ala Phe Asn Arg Lys Lys Leu Thr Leu His Pro Gly
1               5                   10                  15

Leu Phe Val Ala Leu Ser Ala Ile Phe Ser Leu Gly Ser Thr Ala Tyr
            20                  25                  30

Ala Asn Asp Thr Pro Ala Ser Gly Tyr Gln Val Glu Lys Val Val Ile
            35                  40                  45

Leu Ser Arg His Gly Val Arg Ala Pro Thr Lys Met Thr Gln Thr Met
50                  55                  60

Arg Asp Val Thr Pro Asn Thr Trp Pro Glu Trp Pro Val Lys Leu Gly
65                  70                  75                  80

Tyr Ile Thr Pro Arg Gly Glu His Leu Ile Ser Leu Met Gly Gly Phe
            85                  90                  95

Tyr Arg Gln Lys Phe Gln Gln Gln Gly Ile Leu Ser Gln Gly Ser Cys
            100                 105                 110

Pro Thr Pro Asn Ser Ile Tyr Val Trp Thr Asp Val Asp Gln Arg Thr
            115                 120                 125

Leu Lys Thr Gly Glu Ala Phe Leu Ala Gly Leu Ala Pro Glu Cys His
            130                 135                 140

Leu Thr Ile His His Gln Gln Asp Ile Lys Lys Ala Asp Pro Leu Phe
145                 150                 155                 160

His Pro Val Lys Ala Gly Ile Cys Ser Met Asp Lys Thr Gln Val Gln
            165                 170                 175

Gln Ala Val Glu Lys Glu Ala Gln Thr Pro Ile Asp Asn Leu Asn Gln
            180                 185                 190

Arg Tyr Ile Pro Ser Leu Ala Leu Met Asn Thr Ile Leu Asn Phe Ser
            195                 200                 205

Lys Ser Pro Trp Cys Gln Lys His Ser Ala Asp Lys Ser Cys Asp Leu
            210                 215                 220

Gly Leu Ser Met Pro Ser Lys Leu Ser Ile Lys Asp Asn Gly Asn Glu
225                 230                 235                 240

Val Ala Leu Asp Gly Ala Ile Gly Leu Ser Ser Thr Leu Ala Glu Ile
                245                 250                 255

Phe Leu Leu Glu Tyr Ala Gln Gly Met Pro Gln Val Ala Trp Gly Asn
            260                 265                 270

Ile His Ser Glu Gln Glu Trp Ala Ser Leu Leu Lys Leu His Asn Val
        275                 280                 285

His Phe Asp Leu Met Glu Arg Thr Pro Tyr Ile Ala Arg His Lys Gly
    290                 295                 300

Thr Pro Leu Leu Gln Ala Ile Ser Asn Ala Leu Asn Pro Asn Ala Thr
305                 310                 315                 320

Glu Ser Lys Leu Pro Asp Ile Ser Pro Asp Asn Lys Ile Leu Phe Phe
                325                 330                 335

Ala Gly His Asp Thr Asn Ile Ala Asn Ile Ala Gly Met Leu Asn Met
            340                 345                 350

Arg Trp Thr Leu Pro Gly Gln Pro Asp Asn Thr Pro Pro Gly Gly Ala
        355                 360                 365

Leu Val Phe Glu Arg Leu Ala Asp Lys Ser Gly Lys Gln Tyr Val Ser
    370                 375                 380

Val Ser Met Val Tyr Gln Thr Leu Glu Gln Leu Arg Ser Gln Thr Pro
385                 390                 395                 400

Leu Ser Leu Asn Gln Pro Ala Gly Ser Val Gln Leu Lys Ile Pro Gly
                405                 410                 415

Cys Asn Asp Gln Thr Ala Glu Gly Tyr Cys Pro Leu Ser Thr Phe Thr
            420                 425                 430

Arg Val Val Ser Gln Ser Val Glu Pro Gly Cys Gln Leu Gln
        435                 440                 445

<210> SEQ ID NO 48
<211> LENGTH: 446
<212> TYPE: PRT
<213> ORGANISM: Artificial sequence
<220> FEATURE:
<223> OTHER INFORMATION: Synthetic construct

<400> SEQUENCE: 48

Met Thr Ile Ser Ala Phe Asn Arg Lys Lys Leu Thr Leu His Pro Gly
1               5                   10                  15

Leu Phe Val Ala Leu Ser Ala Ile Phe Ser Leu Gly Ser Thr Ala Tyr
            20                  25                  30

Ala Asn Asp Thr Pro Ala Ser Gly Tyr Gln Val Glu Lys Val Val Ile
        35                  40                  45

Leu Ser Arg His Gly Val Arg Ala Pro Thr Lys Met Thr Gln Thr Met
    50                  55                  60

Arg Asp Val Thr Pro Tyr Thr Trp Pro Glu Trp Pro Val Lys Leu Gly
65                  70                  75                  80

Tyr Ile Thr Pro Arg Gly Glu His Leu Ile Ser Leu Met Gly Gly Phe
                85                  90                  95

Tyr Arg Gln Lys Phe Gln Gln Gly Ile Leu Ser Gly Ser Cys
            100                 105                 110

Pro Thr Pro Asn Ser Ile Tyr Val Trp Ala Asp Val Glu Gln Arg Thr
        115                 120                 125

Leu Lys Thr Gly Glu Ala Phe Leu Ala Gly Leu Ala Pro Glu Cys His
    130                 135                 140

Leu Thr Ile His His Gln Gln Asp Ile Lys Lys Ala Asp Pro Leu Phe
145                 150                 155                 160

```
His Pro Val Lys Ala Gly Ile Cys Ser Met Asp Lys Thr Gln Val Gln
            165                 170                 175

Gln Ala Val Glu Lys Glu Ala Gln Thr Pro Ile Asp Asn Leu Asn Gln
        180                 185                 190

Arg Tyr Ile Pro Ser Leu Ala Leu Met Asn Thr Ile Leu Asn Phe Ser
    195                 200                 205

Lys Ser Pro Trp Cys Gln Lys His Ser Ala Asp Lys Ser Cys Asp Leu
210                 215                 220

Gly Leu Ser Met Pro Ser Lys Leu Ser Ile Lys Asp Asn Gly Asn Glu
225                 230                 235                 240

Val Ala Leu Asp Gly Ala Ile Gly Leu Ser Ser Thr Leu Ala Glu Ile
                245                 250                 255

Phe Leu Leu Glu Tyr Ala Gln Gly Met Pro Gln Val Ala Trp Gly Asn
            260                 265                 270

Ile His Ser Glu Gln Glu Trp Ala Ser Leu Leu Lys Leu His Asn Val
        275                 280                 285

His Phe Asp Leu Met Glu Arg Thr Pro Tyr Ile Ala Arg His Lys Gly
    290                 295                 300

Thr Pro Leu Leu Gln Ala Ile Ser Asn Ala Leu Asn Pro Asn Ala Thr
305                 310                 315                 320

Glu Ser Lys Leu Pro Asp Ile Ser Pro Asp Asn Lys Ile Leu Phe Ile
                325                 330                 335

Ala Gly His Asp Thr Asn Ile Ala Asn Ile Ala Gly Met Leu Asn Met
            340                 345                 350

Arg Trp Thr Leu Pro Gly Gln Pro Asp Asn Thr Pro Pro Gly Gly Ala
        355                 360                 365

Leu Val Phe Glu Arg Leu Ala Asp Lys Ser Gly Lys Gln Tyr Val Ser
    370                 375                 380

Val Ser Met Val Tyr Gln Thr Leu Glu Gln Leu Arg Ser Gln Thr Pro
385                 390                 395                 400

Leu Ser Leu Asn Gln Pro Ala Gly Ser Val Leu Lys Ile Pro Gly
                405                 410                 415

Cys Asn Asp Gln Thr Ala Glu Gly Tyr Cys Pro Leu Ser Thr Phe Thr
            420                 425                 430

Arg Val Val Ser Gln Ser Val Glu Pro Gly Cys Gln Leu Gln
        435                 440                 445

<210> SEQ ID NO 49
<211> LENGTH: 444
<212> TYPE: PRT
<213> ORGANISM: Artificial sequence
<220> FEATURE:
<223> OTHER INFORMATION: Synthetic construct

<400> SEQUENCE: 49

Met Thr Ile Ser Leu Phe Thr His Ser Pro Thr Arg Leu Leu Lys Cys
1               5                   10                  15

Met Pro Leu Ala Phe Ile Ala Ala Ser Met Leu Thr Thr Ala Ser Tyr
            20                  25                  30

Ala Ser Glu Thr Glu Pro Ser Gly Tyr Gln Leu Glu Lys Val Val Ile
        35                  40                  45

Leu Ser Arg His Gly Val Arg Ala Pro Thr Lys Met Thr Gln Thr Met
    50                  55                  60

Arg Asp Val Thr Pro Asn Ala Trp Pro Glu Trp Pro Val Lys Leu Gly
65                  70                  75                  80
```

Tyr Ile Thr Pro Arg Gly Glu His Leu Val Ser Leu Met Gly Gly Phe
            85                  90                  95

Tyr Arg Gln Lys Phe Gln Gln Leu Gly Ile Leu Ser Lys Gly Arg Cys
       100                 105                 110

Pro Thr Ala Asn Asp Val Tyr Val Trp Ala Asp Val Asp Gln Arg Thr
            115                 120                 125

Arg Lys Thr Gly Glu Ala Phe Leu Ala Gly Leu Ala Pro Glu Cys His
       130                 135                 140

Leu Ser Ile His His Gln Gln Asp Ile Lys Gln Ala Asp Pro Leu Phe
145                 150                 155                 160

His Pro Val Lys Ala Gly Val Cys Thr Met Glu Lys Thr Gln Val Gln
                165                 170                 175

Gln Ala Val Glu Gln Gln Ala Gly Met Pro Ile Asp Gln Leu Asn Gln
            180                 185                 190

His Tyr Arg Pro Ala Leu Ala Leu Met Ser Ser Val Leu Asn Phe Pro
       195                 200                 205

Lys Ser Thr Tyr Cys Gln Gln His Ser Ala Asp Gln Thr Cys Asp Leu
       210                 215                 220

Ala Gln Ala Met Pro Ser Lys Leu Ser Ile Lys Asp Asn Gly Asn Lys
225                 230                 235                 240

Val Ala Leu Asp Gly Ala Val Gly Leu Ser Ser Thr Leu Ala Glu Ile
                245                 250                 255

Phe Leu Leu Glu Tyr Ala Gln Gly Met Pro Asp Ala Ala Trp Gly Lys
            260                 265                 270

Ile His Ser Glu Gln Asp Trp Asn Ala Leu Leu Thr Leu His Asn Ala
       275                 280                 285

Gln Phe Asp Leu Met Ser Arg Thr Pro Tyr Ile Ala Lys His Asn Gly
       290                 295                 300

Thr Pro Leu Leu Gln Thr Ile Val Ser Ala Ile Asn Ser Gln Pro Ser
305                 310                 315                 320

Ser Arg Glu Leu Pro Glu Leu Ser Ala Asp Asn Lys Ile Leu Phe Pro
            325                 330                 335

Ala Gly His Asp Thr Asn Ile Ala Asn Ile Ala Gly Met Phe Gly Met
       340                 345                 350

Ser Trp Ala Leu Pro Gly Gln Pro Asp Asn Thr Pro Pro Gly Gly Ala
       355                 360                 365

Leu Val Phe Glu Arg Trp Ser Asp Lys Thr Gly Lys Lys Tyr Val Ser
       370                 375                 380

Val Gln Met Met Tyr Gln Thr Leu Ala Gln Leu Arg Asn Gln Thr Pro
385                 390                 395                 400

Leu Thr Leu Asp Lys Pro Ala Gly Ser Val Ala Leu Lys Ile Pro Gly
                405                 410                 415

Cys Asp Asp Gln Thr Ala Glu Gly Tyr Cys Pro Leu Asp Thr Phe Thr
            420                 425                 430

Arg Leu Ala Lys Gln Asn Glu Leu Val Glu Cys Gln
       435                 440

<210> SEQ ID NO 50
<211> LENGTH: 12
<212> TYPE: PRT
<213> ORGANISM: Artificial Sequence
<220> FEATURE:
<223> OTHER INFORMATION: Synthetic

<400> SEQUENCE: 50

```
Ala Cys Met Ser His Thr Trp Gly Glu Arg Asn Leu
1               5                   10
```

<210> SEQ ID NO 51
<211> LENGTH: 14
<212> TYPE: PRT
<213> ORGANISM: Artificial Sequence
<220> FEATURE:
<223> OTHER INFORMATION: Synthetic

<400> SEQUENCE: 51

```
His Gly Trp Gly Glu Asp Ala Asn Leu Ala Met Asn Pro Ser
1               5                   10
```

<210> SEQ ID NO 52
<211> LENGTH: 30
<212> TYPE: PRT
<213> ORGANISM: Artificial Sequence
<220> FEATURE:
<223> OTHER INFORMATION: Synthetic

<400> SEQUENCE: 52

```
Ala Ala Leu Asn Asn Ser Ile Gly Val Leu Gly Val Ala Pro Ser Ala
1               5                   10                  15

Glu Leu Tyr Ala Val Lys Val Leu Gly Ala Ser Gly Ser Gly
            20                  25                  30
```

<210> SEQ ID NO 53
<211> LENGTH: 30
<212> TYPE: PRT
<213> ORGANISM: Artificial Sequence
<220> FEATURE:
<223> OTHER INFORMATION: Synthetic

<400> SEQUENCE: 53

```
Ala Ala Leu Asn Asn Ser Ile Ala Val Leu Gly Val Ala Pro Ser Ala
1               5                   10                  15

Glu Leu Tyr Ala Val Lys Val Leu Gly Ala Ser Gly Ser Gly
            20                  25                  30
```

<210> SEQ ID NO 54
<211> LENGTH: 28
<212> TYPE: PRT
<213> ORGANISM: Artificial Sequence
<220> FEATURE:
<223> OTHER INFORMATION: Synthetic

<400> SEQUENCE: 54

```
Ala Ala Leu Asn Asn Ser Ile Gly Val Leu Gly Val Ala Pro Ser Ala
1               5                   10                  15

Glu Leu Tyr Ala Val Lys Val Leu Gly Ala Ser Gly
            20                  25
```

<210> SEQ ID NO 55
<211> LENGTH: 29
<212> TYPE: PRT
<213> ORGANISM: Artificial Sequence
<220> FEATURE:
<223> OTHER INFORMATION: Synthetic

<400> SEQUENCE: 55

```
Ala Ala Leu Asn Asn Ser Ile Gly Leu Gly Val Ala Pro Ser Ala Glu
1               5                   10                  15

Leu Tyr Ala Val Lys Val Leu Gly Ala Ser Gly Ser Gly
            20                  25
```

-continued

```
<210> SEQ ID NO 56
<211> LENGTH: 12
<212> TYPE: PRT
<213> ORGANISM: Artificial Sequence
<220> FEATURE:
<223> OTHER INFORMATION: Synthetic

<400> SEQUENCE: 56

Ala Gln Ser Val Pro Trp Gly Ile Ser Arg Val Gln
1               5                   10

<210> SEQ ID NO 57
<211> LENGTH: 15
<212> TYPE: PRT
<213> ORGANISM: Artificial Sequence
<220> FEATURE:
<223> OTHER INFORMATION: Synthetic

<400> SEQUENCE: 57

Ala Thr Gly Ala Gln Ser Val Pro Trp Gly Ile Ser Arg Val Gln
1               5                   10                  15

<210> SEQ ID NO 58
<211> LENGTH: 22
<212> TYPE: PRT
<213> ORGANISM: Artificial Sequence
<220> FEATURE:
<223> OTHER INFORMATION: Synthetic

<400> SEQUENCE: 58

Ala Thr Ser Leu Gly Ser Thr Asn Leu Tyr Gly Ser Gly Leu Val Asn
1               5                   10                  15

Ala Glu Ala Ala Thr Arg
            20

<210> SEQ ID NO 59
<211> LENGTH: 24
<212> TYPE: PRT
<213> ORGANISM: Artificial Sequence
<220> FEATURE:
<223> OTHER INFORMATION: Synthetic

<400> SEQUENCE: 59

Ala Thr Ser Leu Gly Ser Thr Asn Leu Tyr Gly Ser Gly Leu Val Asn
1               5                   10                  15

Ala Glu Ala Ala Thr Arg Ser Thr
            20
```